(12) United States Patent
Vail, III et al.

(10) Patent No.: US 7,048,953 B2
(45) Date of Patent: May 23, 2006

(54) METHODS AND APPARATUS TO PREVENT, TREAT AND CURE INFECTIONS OF THE HUMAN RESPIRATORY SYSTEM BY PATHOGENS CAUSING SEVERE ACUTE RESPIRATORY SYNDROME (SARS)

(75) Inventors: William Banning Vail, III, Bothell, WA (US); Marilyn L. Vail, Bothell, WA (US)

(73) Assignee: Inhalation, Inc., Woodinville, WA (US)

( * ) Notice: Subject to any disclaimer, the term of this patent is extended or adjusted under 35 U.S.C. 154(b) by 0 days.

(21) Appl. No.: 10/429,077

(22) Filed: May 2, 2003

(65) Prior Publication Data

US 2004/0009245 A1    Jan. 15, 2004

Related U.S. Application Data

(63) Continuation-in-part of application No. 10/269,891, filed on Oct. 12, 2002, which is a continuation-in-part of application No. 10/241,441, filed on Sep. 9, 2002, which is a continuation-in-part of application No. 09/542,703, filed on Apr. 3, 2000, now Pat. No. 6,447,816.

(60) Provisional application No. 60/328,912, filed on Oct. 12, 2001, provisional application No. 60/377,177, filed on May 5, 2002, provisional application No. 60/449,379, filed on Feb. 21, 2003, provisional application No. 60/457,085, filed on Mar. 24, 2003, provisional application No. 60/457,849, filed on Mar. 26, 2003, provisional application No. 60/460,985, filed on Apr. 7, 2003.

(51) Int. Cl.
*A61K 35/78* (2006.01)
*A61K 51/00* (2006.01)
*A01N 25/00* (2006.01)

(52) U.S. Cl. ............... 424/742; 514/888; 424/1.13; 424/404

(58) Field of Classification Search ........... 424/725, 424/742, 404, 1.13; 514/957, 888
See application file for complete search history.

(56) References Cited

U.S. PATENT DOCUMENTS

| | | | |
|---|---|---|---|
| 4,523,589 | A | 6/1985 | Krauser |
| 4,955,945 | A | 9/1990 | Weick |
| 5,175,152 | A | 12/1992 | Singh |
| 5,511,726 | A | 4/1996 | Greenspan et al. |
| 5,578,338 | A | 11/1996 | Shimabukuro |
| 5,666,946 | A | 9/1997 | Langenback |
| 6,207,703 | B1 | 3/2001 | Ponikau |
| 6,291,500 | B1 | 9/2001 | Ponikau |
| 6,416,955 | B1 | 7/2002 | Sherris et al. |
| 6,447,816 | B1 | 9/2002 | Vail, III et al. |
| 6,550,474 | B1 | 4/2003 | Anderson et al. |
| 6,555,566 | B1 | 4/2003 | Ponikau |
| 2001/0002400 | A1 | 5/2001 | Ponikau |
| 2001/0006944 | A1 | 7/2001 | Ponikau |
| 2001/0031779 | A1 | 10/2001 | Ponikau |
| 2002/0052390 | A1 | 5/2002 | Ponikau |
| 2002/0189608 | A1 | 12/2002 | Raudenbush |
| 2003/0086991 | A1 | 5/2003 | Hughes et al. ............ 424/769 |
| 2003/0087848 | A1 | 5/2003 | Bratzler et al. |
| 2003/0098022 | A1 | 5/2003 | Nakao et al. |

FOREIGN PATENT DOCUMENTS

| | | |
|---|---|---|
| DE | 296 20 182 U1 | 5/1997 |
| JP | 11-209265 | 8/1999 |
| RU | 1820509 C  * | 12/1995 |
| SU | 1214103 A  * | 2/1986 |
| SU | 1782591 A1 * | 12/1992 |
| WO | WO 00/65341 | 11/2000 |
| WO | WO 01/60395 A2 | 8/2001 |
| WO | WO 03/037412 A2 | 5/2003 |

OTHER PUBLICATIONS

Maruzella et al., J.C. J. Am. Pharm. Ass., 1960, vol. 49, No. 11, pp. 692-694. Antibacterial Activity of Essential Oil Vapors.*

Mann et al., C.M. Letters in Applied Microbiology, 2000, 30: 294-297. Outer Membrane of Pseudomonas aeruginosa NCTC 6749 Contributes to its Tolerance to the Essential Oil of Melaleuca alternifolia (tea tree oil).*

Audesirk et al., "Biology, Life on Earth", Fourth Edition, pp. 427-429, and 522-523, Prentice Hall, Upper Saddle River, NJ, 1996.

Balch et al., "Prescription for Nutritional Healing", Second Edition, pp. 69, 77, 167-169, 209-211, 277, 346-348, and 428-430, Avery Publishing Group, Garden City Park, NY, 1997.

Fugh-Berman, "Alternative Medicine, What Works", pp. 3-16, and 192-194, Williams & Wilkins, Baltimore, MD, 1997.

(Continued)

*Primary Examiner*—Michele Flood

(57) ABSTRACT

Concentrated vapors from botanical essential oils are inhaled to prevent, treat and cure infections of the respiratory pathogens causing Severe Acute Respiratory Syndrome ("SARS"). These vapors are inhaled as a practical method to reduce the risks of infection by the pathogens causing SARS in crowded public places. These vapors are also inhaled as a practical method to reduce the risks of infection by unknown, and unpredictable, respiratory pathogens that may be present in public places. The essential oils have antiseptic properties, are safe to inhale, and include, but are not limited to, the essential oils from *Eucalyptus globulus, Melaleuca alternifolia, Eucalyptus citriodora,* and *Eucalyptus radiata.* Convenient hand-held inhaler apparatus are provided for the inhalation of concentrated vapors from the antiseptic essential oils and other substances. The antiseptic essential oils have selected antiviral, antibacterial, and antifungal properties.

7 Claims, 11 Drawing Sheets

OTHER PUBLICATIONS

Hans Dieter Knoch, "Tea Tree Export—Typical Analysis", pp. 1-3, ttexport@nrg.com.au, Mar. 9, 2000.

Hawken, "Natural Cold and Flu Defense", pp. 5-30, Woodland Publishing, Pleasant Grove, UT, 1997.

Hodges et al., "Component Analysis of Eucalyptus Oil by Gas Chromatography-Fouier Transform-Infrared Spectrometry-Mass Spectrometry", Journal of Chromatographic Science, pp. 345-350, vol. 29(8), Aug. 1991.

Hoffman, "The Herbal Handbook", p. 95, Healing Arts Press, Rochester, VT, 1998.

Hoffmann, "The Complete Illustrated Holistic Herbal", pp. 184-187, Element Books, Inc., 1996.

Igram, "Killed on Contact, The Tea Tree Oil Story: Nature's Finest Antiseptic", pp. 1-18, and 51-61, Literary Visions Publishing, Inc., Cedar Rapids, IA, 1992.

Kohn et al., "To Err is, Human Building a Safer Health System, Advance Copy", pp. 1-14, Institute for Medicine, National Academy Press, Washington D.C., 1999.

Lawless, "Tea Tree Oil", pp. 3-29 and 111-114, Harper Collins Publishers, Hammersmith, London, U.K., 1994.

Lawless, "The Illustrated Encyclopedia of Essential Oils", pp. 139-141, Barnes & Noble Books, New York, NY, 1999.

Luckmann, "Saunders, Manual of Nursing Care", pp. 921-929, W.B. Saunders Company, Philadelphia, PA, 1997.

Martin et al., "A Dictionary of Biology", Third Edition, p. 31, Oxford University Press, New York, NY, 1996.

Miller et al., "Ayurveda & Aromatherapy, The Earth Essential Guide to Ancient Wisdom and Modern Healing", pp. 251-252, Lotus Press, Twin Lakes, WI, 1995.

Murray et al., "An Encyclopedia of Natural Medicine", pp. 227-231, Prima Publishing, Rocklin, CA, 1991.

Olsen, "Australian Tea Tree Oil Guide", pp. 14-16, Kali Press, Pagosa Springs, CO, 1991.

Olsen, "Australian Tea Tree Oil Guide", Third Edition, pp. 10-13, and 82-84, Kali Press, Pagosa Springs, CO, 1997.

Roberts et al., "Asthma: An Alternative Approach", pp. 133-137, Keats Publishing, Inc., New Canaan, CT, 1997.

Rose, "375 Essential Oils and Hydrosols", pp. 77-78, Frog Limited, Berkeley, CA, 1999.

Schnaubelt, "Advanced Aromatherapy, The Science of Essential Oil Therapy", pp. 31-41, and 96-124, Healing Arts Press, Rochester VT, 1998.

Swords et al., "Composition of Australian Tea tree Oil (Melaleuca altemifolia)", pp. 734-737, Journal of Agricultural Food Chemistry, vol. 26, No. 3, 1978.

Tenney, "Aromatherapy, Essential Oils for Essential Health", pp. 5-26, Woodland Publishing, Pleasant Grove, UT, 1997.

The Seattle Times, "Medical Digest—Protein could beat cholesterol as indicator of heart risk", Friday, Mar. 24, 2000.

Weinstein, "Asthma, The Complete Guide to Self-Management of Asthma and Allergies for Patients and Their Families", pp. 1-357, A Fawcett Crest Book, The Ballantine Publishing Group, New York, NY, 1988.

Williams, "New Uses for An Age-Old Therapy", pp. 25-27, Alternatives For the Health Conscious Individual, vol. 8, No. 4, Oct. 1999.

Anderson, "Mosby's Medical Dictionary", Fourth Edition, pp. 1476-1477, Mosby-Year Book, Inc., St. Louis, MO, 1994.

McGuffin et al., "American Herbal Products Association's Botanical Safety Handbook", pp. 155-157, CRC Press, New York, NY, 1997.

Paterson et al., "Reduced susceptibility of *Staphylococcus aureus* to vancomycin—a review of current knowledge" pp. 1-6, Communicable Disease Intelligence, vol. 23 No. 3, Apr. 20, 1999.

Sherry et. al., "Alternative for MRSA and Tuberculosis (TB): Eucalyptus and Tea-Tree Oils as New Topical Antibacterials", 2002 Annual Meeting of the American Academy of Orthopaedic Surgeons, Feb. 13-17, 2002, Dallas, TX, Poster Board No. P376.

Blumenthal et al., The Complete German Commission E Monographs: Therapeutic Guide to Herbal Medicines, p 267, "Fixed combinations of eucalyptus oil and pine needle oil, published Jul. 14, 1993", American Botanical Council, USA, 1998.

Carson et al., J. of Applied Bacteriology (1995), 78:264-269, "Antimicrobial activity of the major components of the essential oil of *Melaleuca alternifolia*".

Carson et al., J. Antimicrobial Chemotherapy (1995), 35:421-424, "Susceptibilty of methicillin-resistant *Staphyloccus aureus* to the essential oil of *Melaleuca alternifolia*".

Balch et al., Prescription for Nutritional Healing, Second Edition, p. 144, pp. 167-168, Avery Publishing Group, Garden City Park, NY, 1997.

Hoffmann, The Complete Illustrated Herbal, pp. 184-185, Barnes & Noble Books, 1999.

Grant, "Prolific Botheil inventor tackles common cold with latest creation", pp. D1 and D6, Eastside Journal, Sep. 14, 2002.

Dietrich, "Vapor Inhaler gives inventor a mist opportunity", p. 16, Puget Sound Business Journal, Feb. 21-27, 2003.

Berkow et al., "The Merck Manual of Medical Information, Home Edition", pp. 1015-1017, Pocket Books, a division of Simon & Schuster, Inc., New York, NY, 1997.

Beers et al., "The Merck Manual of Diagnosis and Therapy", Seventeenth Edition, Centennial Edition, Home, Section 7, Chapter 86, "Sinusitis", 1999.

Allergy, Asthma, and Sinus Resource Center,"Allergy & Sinus Relief Without Drugs", www.allergy-asthma-sinus.com, Apr. 30, 2002.

Medical College of Wisconsin Physicians & Clinics, "Sinusitis (Sinus Infection)", Health Link, Apr. 30, 2002.

"Sinusitis", Medical Encyclopedia, drkoop.com, Apr. 30, 2002.

Beers et al., "The Merck Manual of Diagnosis and Therapy" Seventeenth Edition, Centennial Edition, Home, Section 13, Chapter 157, "Caused By Mycobacteria—Tuberculosis", 1999.

Balch et al., "Prescription for Nutritional Healing", Third Edition, pp. 311-313, Avery Publishing Group, Garden City Park, NY, 2000.

Beers et al., "The Merck Manual of Diagnosis and Therapy" Seventeenth Edition, Centennial Edition, Home, Section 19, Chapter 267, "Cystic Fibrosis", 1999.

Balch et al., "Prescription for Nutritional Healing", Third Edition, pp. 567-569, Avery Publishing Group, Garden City Park, NY, 2000.

Beers et al., "The Merck Manual of Diagnosis and Therapy" Seventeenth Edition, Centennial Edition, Home, Section 6, Chapter 73, "Pneumonia", 1999.

Balch et al., "Prescription for Nutritional Healing", Third Edition, pp. 297-300, 468-470, Avery Publishing Group, Garden City Park, NY, 2000.

Beers et al., "The Merck Manual of Diagnosis and Therapy" Seventeenth Edition, Centennial Edition, Home, Section 13, Chapter 162, "Respiratory Viral Diseases", 1999.

"Common Infections", www.cohis.org, Apr. 30, 2002.

Beers et al., "The Merck Manual of Diagnosis and Therapy" Seventeenth Edition, Centennial Edition, Home, Section 7, Chapter 86, "Rhinitis", 1999.

Balch et al., "Prescription for Nutritional Healing", Third Edition, pp. 195-200, Avery Publishing Group, Garden City Park, NY, 2000.

Berkow et al., "The Merck Manual of Medical Information, Home Edition", pp. 173-180, Pocket Books, a division of Simon & Schuster, Inc., New York, NY, 1997.

Beers et al., "The Merck Manual of Diagnosis and Therapy" Seventeenth Edition, Centennial Edition, Home, Section 6, Chapter 68, "Chronic Obstructive Airway Disorders", 1999.

Price et al., "Aromatherapy for Health Professionals", pp. 59-87, Churchill Livingstone, New York, NY, 2000.

Inouye et al., "Antibacterial activity of essential oils and their major constituents against respiratory tract pathogens by gaseous contact", Journal of Antimicrobial Chemotherapy, vol. 47, 565-573, 2001.

Zakarya et al., "Chemical Composition-Antimicrobial Activity Relationships of *Eucalyptus* Essential Oils", Plantes médicinales et phytothérapie, vol. XXVI, No. 4, pp. 319-331.

Maruzzella et al., "The Action of Perfume Oil Vapors on Fungi", American Perfurmer and Aromatics, vol. 73, Jan.-Jun. 1959, pp. 21-22.

Maruzzella et al., "Antibacterial Activity of Essential Oil Vapors", Journal of the American Pharmaceutical Association, vol. 49, No. 11, Nov. 1960, pp, 692-694.

Boyd et al., "Nutmeg Oil and Camphene as Inhaled Expectorants", Archives of Otolaryngology, vol. 92, No. 4, Oct. 1970, pp. 372-378.

Megalla et al., "A Study of Antimicrobial Action of Some Essential Oil Constituents", Herba Polonica, vol. XXVI No. 3, 1980, pp. 181-186.

Pandey et al., "Fungitoxic and phytotoxic properties of the essential oil Hyptis suaveolens", Journal of Plant Diseases and Protection, vol. 89 No. 6, 1982, pp. 344-349.

Burrow et al., "The Effects of Camphor, Eucalyptus and Menthol Vapour on Nasal Resistance to Airflow and Nasal Sensation", Acta Oto-Laryngologica, vol. 96, No. 1-2, Jul.-Aug. 1983, pp. 157-161.

Inouye et al., "Inhibitory Effect of Volatile Constituents of Plants on the Proliferation of Bacteria—Antibacterial Activity of Plant Volatiles—", Journal of Antibacterial Antifungal Agents, vol. 11, No. 11, 1983, pp. 609-615.

Goi et al., "Antifungal Activity of Powdery Black Mustard, Powdery Wasabi (Japanese Horseradish), and Allyl Isothiocyanate by Gaseous Contact—Antifungal Activity of Plant Volatiles—", Journal of Antibacterial Antifungal Agents, vol. 13, No. 5, 1985, pp. 199-204.

Onawunrmi et al., "Effects of lemon grass oil on the cells and spheroplasts of *Escherichia coli* NCTC 9001", Microbios Letters, vol. 28 No. 110, 1985, pp. 63-68.

Moleyar et al., "Antifungal activity of some essential oil components", Food Microbiology, vol. 3 No. 4, Oct. 1986, pp. 331-336.

Knobloch et al., "Antibacterial and Antifungal Properties of Essential Oil Components", Journal of Essential Oil Research, vol. 1 No. 3, May/Jun. 1989, pp. 119-128.

Farag et al., ,"Antimicrobial Activity of Some Egyptian Spice Essential Oils", Journal of Food Protection, vol. 52 No. 9, Sep. 1989, pp. 665-667.

Gocho, "Antibacterial Action of Aroma Compounds in Vapor State", Journal of Antibacterial Antifungal Agents, vol. 19, No. 7, 1991, pp. 329-334.

Grosjean et al., "Atmospheric Oxidation of Selected Terpenes and Related Carbonyls: Gas-Phase Carbonyl Products", ES&T, vol. 26 No. 8, Aug. 1992, pp. 1526-1533.

Orafidiya, "The Effect of Autoxidation of Lemon-grass Oil on its Antibacterial Activity", Phytotherapy Research, vol. 7, 1993, pp. 269-271.

Laude et al., "The Antitussive Effects of Menthol, Camphor and Cineole in Conscious Guinea-pigs", Pulmonary Pharmacology, vol. 7, 1994, pp. 179-184.

Tassou et al., "Antimicrobial Activity of the Essential Oil of Mastic Gum (*Pistacia lentiscus* var. *chia*) on Gram Positive and Gram Negative Bacteria in Broth and in Model Food System", International Biodeterioration & Biodegradation, vol. 36, 1995, pp. 411-420.

Singh et al., "Cinnamon bark oil, a potent fungitoxicant against fungi causing respiratory tract mycoses", Allergy, vol. 50 No. 12, Dec. 1995, pp. 995-999.

Smith-Palmer et al., "Antimicrobial properties of plant essential oils and essences against five important food-borne pathogens", Letters in Applied Microbiology, vol. 26 No. 2, Feb. 1998, pp. 118-122.

Mann et al., "The outer membrane of *Pseudomonas aeruginosa* NCTC 6749 contributes to its tolerance to the essential oil of *Melaleuca alternifolia* (tea tree oil)", Letters in Applied Microbiology, vol. 30 No. 4, Apr. 2000, pp. 294-297.

Janssen et al., "Antimicrobial Activity of Essential Oils: A 1976-1986 Literature Review. Aspects of the Test Methods", Planta Medica, Journal of Medicinal Plant Research, 1987, pp. 395-398.

Boyd et al., "The Effect of Steam Inhalation of Volatile Oils on the Output and Composition of Respiratory Tract Fluid", The Journal of Pharmacology and Experimental Therapeutics, vol. 163, No. 1, 1968, pp. 250-256.

Inouye et al., "Effect of Sealing and Tween 80 on the Antifungal Susceptibility Testing of Essential Oils", Microbiology and Immunology, vol. 45 No. 3, 2001, pp. 201-208.

Inouye et al., "Screening of the Antibacterial effects of a variety of essential oils on respiratory tract pathogens, using a modified dilution assay method", Journal of Infection and Chemotherapy, vol. 7, No. 4, Dec. 2001, pp. 251-254.

Sherry et al., "Percutaneous treatment of chronic MRSA osteomyelitis with a novel plant-derived antiseptic", BMC Surgery, vol. 1, No. 1 2001, pp. 1-4—Aug. 26, 2003 printout.

Beers et al., "The Merck Manual of Diagnosis and Therapy" Seventeenth Edition, Centennial Edition, Home, Section 6, Chapter 73, "Viral Pneumonia", 1999.

Beers et al., "The Merck Manual of Diagnosis and Therapy" Seventeenth Edition, Centennial Edition, Home, Section 6, Chapter 73, "Pneumonia Caused by Gram-Negative Bacilli", 1999.

Beers et al., "The Merck Manual of Diagnosis and Therapy" Seventeenth Edition, Centennial Edition, Home, Section 6, Chapter 73, "Fungal Pneumonia", 1999.

Alibek, et al., "Biohazard", Dell Publishing, New York, NY, 1999, pp. 1-319.

Ellison, "Handbook of Chemical and Biological Warfare Agents", CRC Press, LLC, New York, NY 2000, pp. 1-507.

Falkenrath, et al., "America's Achilles' Heel", MIT Press, Cambridge, MA, 2001, pp. 1-354.

Institute of Medicine, et al., "Chemical and Biological Terrorism, Research and Development to Improve Civilian Medical Response", National Academy Press, Washington, D.C., 1999, pp. 1-279.

Mangold, et al., "Plague Wars", St. Martin's Griffin, New York, NY, 2001, pp. 1-477.

Miller, et al., "Germs", Simon & Schuster, New York, NY, 2002, pp. 1-407.

Osterholm, et al., "Living Terrors", Delacorte Press, a division of Ramdom House, New York, NY 2000, pp. 1-232.

Regis, "The Biology of Doom", Henry Holt and Company, LLC, New York, NY,1999, pp. 1-259.

Tucker, "Toxic Terror, Assessing Terrorist Use of Chemical and Biological Weapons", MIT Press, Cambridge, MA, 2001, pp. 1-303.

U.S. Appl. No. 10/241,441, filed Sep. 9, 2002, Vail, III et al.

U.S. Appl. No. 60/328,912, filed Oct. 12, 2001, Vail, III et al.

U.S. Appl. No. 60/377,177, filed May 2, 2002, Vail, III et al.

Anderson, "Mosby's Medical Dictionary", Fourth Edition, pp. 1029-1030, Mosby-Year Book, Inc., St. Louis MO, 1994.

Anderson, "Mosby's Medical Dictionary", Fourth Edition, p. 199, Mosby-Year Book, Inc., St. Louis MO, 1994.

Schnaubelt, "Advanced Aromatherapy, The Science of Essential Oil Therapy", p. 14, Healing Arts Press, Rochester VT, 1998.

Vermilye, "Essential Oils, Antibiotic Resistant Bacteria and the SARS Virion?", Paper to be presented at 6th Scientific Wholistic Aromatherapy Conference (Essential Oils: Antiviral Agents), San Francisco, CA, Apr. 8-10, 2005.

* cited by examiner

METHODS AND APPARATUS TO PREVENT, TREAT AND CURE INFECTIONS OF THE HUMAN RESPIRATORY SYSTEM BY PATHOGENS CAUSING SEVERE ACUTE RESPIRATORY SYNDROME (SARS)

CROSS-REFERENCES TO RELATED APPLICATIONS

This application is a Continuation-in-Part Application of co-pending application Ser. No. 10/269,891, having the Filing Date of Oct. 12, 2002, that is entitled "Methods and Apparatus to Prevent, Treat and Cure Infections of the Human Respiratory System from Inhaled Anthrax, Smallpox, Botulism, Plague, Tularemia, Hemorrhagic Fever Viruses, Tuberculosis and Other Inhaled Bioterrorism Pathogens", an entire copy of which is incorporated herein by reference.

Ser. No. 10/269,891 is a Continuation-in-Part Application of co-pending application Ser. No. 10/241,441, having the Filing Date of Sep. 9, 2002, that is entitled "Methods and Apparatus to Prevent Colds, Flus, Tuberculosis and Opportunistic Infections of the Human Respiratory System of Individuals Having Cystic Fibrosis", an entire copy of which is incorporated herein by reference.

Ser. No. 10/241,441 is a Continuation-in-Part application of Ser. No. 09/542,703, having the Filing Date of Apr. 3, 2000 that is entitled "Methods and Apparatus to Prevent Colds, Flus, and Infections of the Human Respiratory System", that issued as U.S. Pat. No. 6,447,816 on the date of Sep. 10, 2002, an entire copy of which is incorporated herein by reference.

This application relates to Provisional Patent Application No. 60/328,912 filed on Oct. 12, 2001 that is entitled "Methods and Apparatus to Prevent Infections of the Human Respiratory System from Inhaled Anthrax, Smallpox, Botulism, Plague, Tularemia, Tuberculosis and Other Inhaled Bioterrorism Pathogens". An entire copy of Provisional Patent Application No. 60/328,912 is incorporated herein by reference.

This application also relates to Provisional Patent Application No. 60/377,177 filed on May 2, 2002 that is entitled "Methods and Apparatus to Prevent, Treat, and Cure Infections of the Human Respiratory System Including the Sinus Cavities, the Nasal Cavities, and the Throat". An entire copy of Provisional Patent Application No. 60/377,177 is incorporated herein by reference.

This application further relates to Provisional Patent Application No. 60/449,379 filed on Feb. 21, 2003 that is entitled "Hand Held Inhalers". An entire copy of Provisional Patent Application No. 60/449,379 is incorporated herein by reference.

This application also relates to Provisional Patent Application No. 60/457,085 filed on Mar. 24, 2003 that is entitled 'Methods and Apparatus to Prevent, Treat, and Cure Infections of Severe Acute Respiratory Syndrome ("SARS")'. An entire copy of Provisional Patent Application No. 60/457,085 is incorporated herein by reference.

This application further relates to Provisional Patent Application No. 60/457,849 filed on Mar. 26, 2003 that is entitled 'Methods and Apparatus to Prevent, Treat, and Cure Severe Acute Respiratory Syndrome ("SARS") Caused by the Infection of One or More Coronaviruses in the Human Respiratory System'. An entire copy of Provisional Patent Application No. 60/457,849 is incorporated herein by reference.

And finally, this application also relates to Provisional Patent Application No. 60/460,985 filed on Apr. 7, 2003 that is entitled 'Methods and Apparatus to Prevent, Treat, and Cure Severe Acute Respiratory Syndrome ("SARS") Caused by the Infection of Two or More Associated Viruses, Bacteria and Fungi. An entire copy of Provisional Patent Application No. 60/460,985 is incorporated herein by reference.

Applicant claims priority from the above U.S. patent application Ser. No. 10/269,891 having the Filing Date of Oct. 12, 2002. Applicant also claims priority from the above U.S. patent application Ser. No. 10/241,441, having the Filing Date of Sep. 9, 2002. Applicant also claims priority from U.S. patent application Ser. No. 09/542,703 having the Filing Date of Apr. 3, 2000.

Applicant also claims any priority from Provisional Patent Application No. 60/328,912 (now expired). Applicant further claims priority from Provisional Patent Application No. 60/377,177. Applicant also claims priority from Provisional Patent Application No. 60/449,379. Applicant further claims priority from Provisional Patent Application No. 60/457,085. Applicant also claims priority from Provisional Patent Application No. 60/457,849. Applicant further claims priority from Provisional Patent Application No. 60/460,985.

This application is related to U.S. Disclosure Document No. 528,070 that has the Filing Date of Mar. 17, 2003 that is entitled 'Methods and Apparatus to Prevent, Treat, and Cure Infections of Severe Acute Respiratory Syndrome ("SARS")', an entire copy of which is incorporated herein by reference.

BACKGROUND OF THE INVENTION

One of the inventors has poor respiratory health, has had repeated bouts with pneumonia, colds, flu, asthma, and has been recently diagnosed with the initial stages of emphysema—despite all that modern medicine has had to offer. This first inventor also comes from a family known for a long history of respiratory problems. Therefore, the inventors decided to look beyond conventional "modern medicine" to help the first inventor, and as a result, have conceived methods to substantially prevent colds, flus, and infections of the human respiratory system. These methods include the inhalation of the vapors from *eucalyptus* oil and/or tea tree oil that are theorized to form a protective, and infection-preventing, thin layer within the entire respiratory system, including the lungs, bronchial tubes, and the nasal cavities. This thin layer maintains its anti-pathogenic properties for a period of time following the inhalation of the vapors for at least one-half hour, and perhaps longer. This thin anti-pathogenic layer substantially prevents the initial infection of colds, flus, and other pathogens for a period of time following inhalation. The inventors also propose the prophylactic use of inhaled *eucalyptus* oil and/or tea tree oil to prevent additional tuberculosis, which is becoming a major health problem in the United States. The inventors further propose the prophylactic use of inhaled *eucalyptus* oil and/or tea tree oil to prevent opportunistic infections of the human respiratory system of individuals having cystic fibrosis.

1. Field of the Invention

The field of invention relates to the prevention of colds, flus, and other pathogens within the respiratory system of human beings by the inhalation of vapors from highly volatile essential oils such as *eucalyptus* oil and/or tea tree oil. Following the inhalation of the vapors, a thin antipathogenic layer is formed in the respiratory system that protects against infection for a certain duration of time following inhalation.

2. Description of the Prior Art

While certain medical uses for *eucalyptus* oil and tea tree oil have been previously disclosed, to the inventor's best knowledge, none of those previously disclosed methods have suggested, or proposed, that the periodic inhalation of vapors from *eucalyptus* oil and/or tea tree oil may be used as prophylactic agents to substantially prevent infection of colds, flus, and other pathogens within the respiratory system of human beings for a duration of time following that inhalation. AFTER the infection of human beings with certain pathogens, previous inhalation therapies have suggested using *eucalyptus* oil and or tea tree oil to aid in the recovery from certain respiratory diseases. However, none of these previous methods have suggested using *eucalyptus* oil and/or tea tree oil vapors as prophylactic agents to routinely and substantially PREVENT the initial infection of pathogens for a duration of time following their inhalation as a primary method of preventing disease.

SUMMARY OF THE INVENTION

An object of the invention is to provide methods to prevent the initial infection of pathogens within the human respiratory system by the inhalation of vapors from *eucalyptus* oil or from any of its constituents.

Another object of the invention is to provide methods to prevent the initial infection of pathogens within the human respiratory system by the inhalation of vapors from tea tree oil or from any of its constituents.

Yet another object of the invention is to prevent respiratory infections from pathogens including bacteria, viruses, and fungi.

And yet another object of the invention is provide methods to substantially prevent diseases such as colds and flus.

Yet another object of the invention is to provide methods to substantially prevent all varieties of pneumonia.

Yet further, another object of the invention is to provide methods to substantially prevent the spread of tuberculosis.

Yet another object of the invention is to provide methods to substantially prevent opportunistic infections of the human respiratory system of individuals having cystic fibrosis.

Another object of the invention is to provide an convenient hand-held inhaler apparatus to provide vapors from essential oils such as *eucalyptus* oil and/or tea tree oil for inhalation into the human respiratory system.

And yet another object of the invention is to provide methods to prevent, treat and cure infections of bioterrorism pathogens including inhalation anthrax, inhalation smallpox, inhalation botulism, inhalation plague, inhalation tularemia, inhalation hemorrhagic fever viruses, and inhalation tuberculosis.

Yet further, it is yet another object of the invention to provide methods to inhale concentrated vapors from different mixtures of essential oils having antiseptic properties to prevent, treat and cure a wide variety of respiratory diseases including infections from bioterrorism pathogens.

Still further, it is yet another object of the invention to provide methods to reduce the risks of infection of the human respiratory system by pathogens causing Severe Acute Respiratory Syndrome (SARS).

It is yet another object of the invention to provide methods and apparatus to prevent, treat, and cure infections by pathogens that cause Severe Acute Respiratory Syndrome (SARS).

And finally, it is yet another object of the invention to provide methods and apparatus to reduce the probability of infection by unknown, and unpredictable, respiratory pathogens in public places.

DESCRIPTION OF THE PREFERRED EMBODIMENTS

Figure 1:
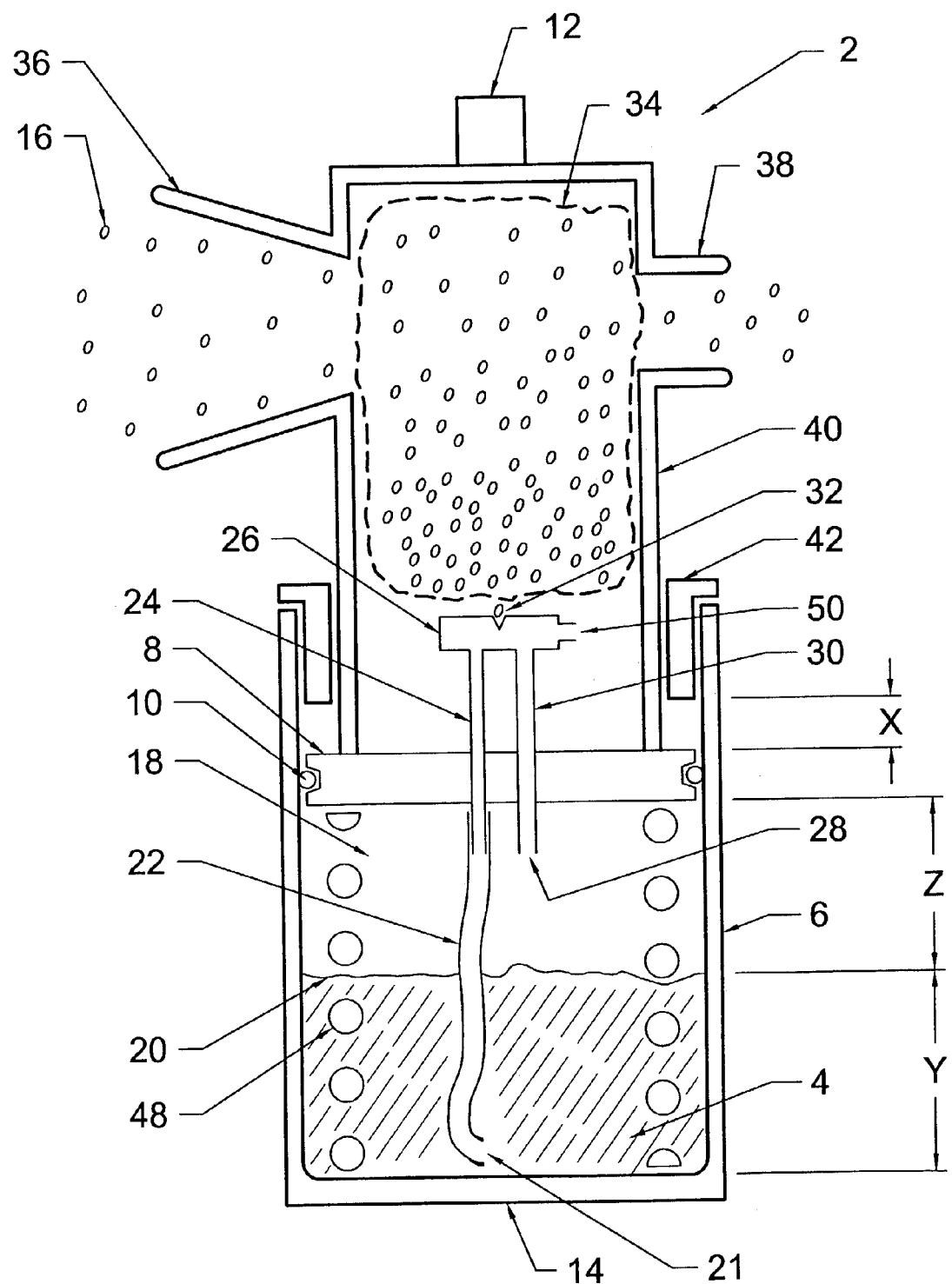
FIG. 1 shows a section view of a hand-held atomizer apparatus to produce vapors from *eucalyptus* oil and/or tea tree oil or from other mixtures of essential oils for inhalation.

Following a business trip to Houston during April of 1998, the first inventor, W. Banning Vail, Ph.D., returned to Seattle and caught a dreadful form of flu. During this severe illness, the first inventor spent several weeks gasping for breath and nearly died. After several trips to a pulmonary specialist, it was found that about ⅓ of the first inventor's lung capacity had been "eaten up" by some sort of infectious agent. Therefore, the first inventor was diagnosed with a form of emphysema.

The physician further informed the first inventor that if one more such infectious episode should occur, and should that episode result in another ⅙ or more of the first inventor's lung capacity being "eaten up" by an infectious agent, then the first inventor would thereafter become a good candidate for use of oxygen tanks. Further, the first inventor was also diagnosed with asthma. The physician provided additional warnings of potential disaster in light of the first inventor's many childhood bouts with pneumonia that left scars on the lungs. Such warnings were also compounded by the first inventor's stupid habit of smoking, which he quite some 20 years ago.

The first inventor's father, William Banning Vail, Jr., had emphysema, and had used oxygen tanks for perhaps five years. Accordingly, the first inventor feared emphysema and the use of oxygen tanks. The terms such as "emphysema", "asthma", and related diseases are defined and described in Weinstein, 1988, an entire copy of which is incorporated herein by reference. The clinical manifestations of emphysema, asthma, and other respiratory infections are defined and described in Luckmann, 1997, an entire copy of which is incorporated herein by reference.

For many years, it seems almost every time that the first inventor had taken an airplane flight, or had otherwise gone into a public place with a large number of people, he had often caught a cold, a flu, or some other "bug". The terms such as "cold", "flu", "infectious disease", "pathogen" "pathogens", "pathogenesis", "pathologic microorganisms", etc., are defined in Anderson, et al., 1994, an entire copy of which is incorporated herein by reference. Here, colds include diseases caused by any strain of a rhinovirus. Here, flus include diseases caused by any type of influenza, including those of the respiratory system. Therefore, the first inventor came to fear airplane flights, being in places with many people, etc. because of fear of being infected again with pathogens that could possible result in death by terminal emphysema.

In Anderson, et. al, 1994, on page 808, the term "risk for infection" is defined as "a state in which an individual is at increased risk for being invaded by pathogenic organisms". Anderson, et. al, 1994, page 808, further states: "Risk factors include inadequate primary defenses, such as broken skin, traumatized tissue, decrease in ciliary action, . . . , tissue destruction, . . . ".

Luckmann, 1997, page 868, also states under the topic of "Nonspecific Body Defenses Against Infection", and under "1. Physical barriers" the following:

"a. Physical, or anatomic, barriers are the 1st line of defense against infection." and "b. Physical barriers include intact skin and mucous membranes lining the respiratory, gastrointestinal and genitourinary tracts."

Therefore, Luckmann, 1997 specifically refers to the mucous membranes lining the respiratory system as being important to prevent infection, and any less than optimum condition of these membranes would provide another "risk factor" favoring infection by some pathogen.

The first inventor has set forth an hypothesis that his respiratory system and lungs are subject to such "risk factors", and that the first inventor had to invent a new method to prevent invasion by such pathogenic organisms. Consequently, the first inventor has concluded that to minimize the possibility of ending up on oxygen tanks, that it is necessary to prevent the infection of his respiratory system by common pathogens such as pathologic bacteria, viruses, and fungi. It is clear that any one of these pathogens may cause disease. However, the first inventor has the additional hypothesis, that in analogy with many biological systems, it is likely that human diseases can also be caused by a combination of such pathogens that form symbiotic relationships, or associated relationships, similar to well-documented mycorrhizal relationships or the like, which may also change in time. For a description of such mechanisms in biology, for example see Audesirk and Audesirk, 1996 on these and related subjects. Therefore, from the first inventor's point of view, it is possible that any one disease may involve bacteria, viruses, and fungi all at one time, and the mix of these may change vs. time as the disease progresses through various stages.

From the first inventor's point of view, many of his illnesses had begun with either cold-like symptoms or flu-like symptoms. If he got very sick, this often progressed into symptoms mimicking those of pneumonia. So, an initial predominant viral-like infection may evolve into a predominantly bacterial-like infection as time progresses. So, the first inventor views the development of some diseases as progression of various stages, where any one stage may have a peculiar mix of pathogens. The progression of colonies of pathogens vs. time may in fact involve viral, bacterial, and fungal elements called for the purposes herein "symbiotic pathogens" that may make "symbiotic pathogenic colonies". Typically, the composition of those "symbiotic pathogenic colonies" vary with time. As has often been the case in the past, when the first inventor had problems with his respiratory system, standard antibiotics rarely helped. In the first inventor's view, this is because the antibiotics only addressed part of the problem in a typically complex case when "symbiotic pathogens" are causing disease that has at least two components among the three that are viral, bacterial, and fungal components. The view that a given disease is often caused by a time varying mix of bacterial, viral, and fungal pathogens provides the precise reason why the first inventor rarely found commercial antibiotics to be of effective help in overcoming his various lung diseases. Accordingly, the first inventor has theorized that to be able to routinely prevent colds, flus, etc., it is necessary to locate substances that have antiviral and antibacterial and antifungal elements that may be applied to the respiratory system simultaneously.

The first inventor further hypothesized that microscopic portions of his respiratory system at any one time are subject to increased risk of invasion by such pathogens. Any such increased risk site for the purposes herein is defined as a "likely pathogenic invasion site". Once a pathogen "invades" such a "likely pathogenic invasion site", for example within tissue within the lungs, then the pathogens may multiply, causing an infection that may "eat away", or destroy, portions of the lungs of the first inventor. The first inventor has concluded that he needs new methods and apparatus to prevent or block the invasion of pathogens into a likely pathogenic invasion site within his respiratory system. Put another way, the first inventor sought to find a practical method to reduce the risk of infection of the respiratory system by infectious agents.

This is a tall order. The first inventor had theorized about using certain face masks, filtering the air inhaled by the lungs, and passing inhaled air through U.V. light (with the energy of the U.V. below the threshold to produce ozone). Then, the first inventor decided to investigate inhaled chemicals to prevent the invasion by pathogens of a likely pathogenic invasion site. Such chemicals need to be highly volatile, non-toxic, and capable of killing bacteria, viruses, and fungi. The second inventor, Marilyn L. Vail, suggested using *eucalyptus* oil and/or tea tree oil as potential candidates because of her prior research on these substances in her attempts to control internal infections of *Candida albicans*.

The inventors identified a class of chemical compounds that may be used to prevent the invasion of pathogens into the respiratory system. They include *eucalyptus* oil and tea tree oil. Here *eucalyptus* oil includes the essential oil from *Eucalyptus globulus,* and here, tea tree oil is the essential oil from *Melaleuca alternifolia*. The first inventor has found that routinely inhaling these substances has prevented him from getting any colds, flus, or pneumonia in his respiratory system through the date of Apr. 28, 2003—several days before the filing date of this application. The first inventor has been practicing the invention every day commencing on, or before, the first day of September of 1999. As a result of using the invention, the first inventor has had no respiratory infections for over 3½ years as of the filing of this application. This is despite the fact that the first inventor has had extensive business travels during this time. This is truly remarkable, because the first inventor has often been sick every several months or so before he began practicing the invention.

There is one fine point here of considerable interest. It is stated above that at this point in time, the first inventor has had no respiratory infections for over 3½ years. This is true. Prior to this period when the first inventor caught the flu, it often eventually attacked the lungs in one way or another. When the flu ended up attacking his respiratory system, the first inventor often became very sick and it would often take three weeks or a month for him to recover. When the first inventor returned home from a backpacking trip during December of 1999, the first inventor's wife had a very bad case of the flu. After several weeks, the first inventor actually caught the flu—but it never attacked the respiratory system of the first inventor. In this situation, when the first inventor caught the flu, he became sick very rapidly, had a fever, sometimes a high fever, and he became sore, and typically his joints ached. However, in this particular case, the flu never attacked his respiratory system. In this case, all symptoms disappeared within 48 hours. This was not a life-threatening situation to the first inventor. The first inventor has actually caught similar flus several times during the last 3½ years, but in all cases, the flus never attacked his respiratory system while practicing the invention. In retrospect, the first inventor views catching mild cases of the flu to be medically positive, because he is then able to develop suitable antibodies to new strains of influenza without the risk of a catastrophic and life-threatening lung infection. So, when using the phase "the first inventor has not caught the flu since practicing the invention" should rigorously read "the first inventor has not caught the flu in his respiratory system since practicing the invention", which correction applies to any such statements herein, or to any other statements in any other applications by the first inventor on this subject.

Soon after conceiving the invention, the first inventor performed experiments on himself with very crude apparatus. A small bottle of "*eucalyptus* rectified essential oil" made by "aroma-vera" was purchased. It had a blockage near the top of the bottle. Typically, the first inventor shook the bottle with the blockage "down" which caused *eucalyptus* oil to catch in the blockage near the top of the bottle. Then, with the bottle held with the blockage "up", and while holding one nostril closed, the first inventor would inhale very deeply through the other nostril thereby inhaling concentrated vapors of *eucalyptus* oil. Then the process was repeated with the other nostril. The first inventor estimates that the amount inhaled ranged between 0.001 milligrams to 100 milligrams, depending upon the circumstances, and the number of repetitions. The first inventor performed this inhalation immediately before he went "into public", such as into an enclosed public area having one or more human beings within that enclosed area. If there were sick people present that were coughing, or otherwise admitted that they had a cold, the flu, or pneumonia, the first inventor would thereafter similarly inhale concentrated vapors of *eucalyptus* oil every 30 minutes or so. By following this process, as further explained in other preferred embodiments below, the first inventor has not had a cold, the flu, or pneumonia attack his respiratory system for the last 3½ years.

The first inventor alternatively used tea tree oil in the above experiments and had similar results. The tea tree oil was in a small bottle marked with the legend "100% PURE AUSTRALIAN TEA TREE OIL" made by Desert Essence.

It is important to note that very strong vapors of either *eucalyptus* oil or tea tree oil were inhaled each time. This happened because of the close proximity of the nose to a pool of highly volatile fluids. However, there were several drawbacks to this method. As a first drawback, on occasion the fluids themselves got sucked up into the nose causing a very unpleasant situation. As a second drawback, if the fluids got on the hands, and then into the eyes, this was also an extraordinarily unpleasant, and perhaps, a dangerous situation. As a third drawback, inhalation through the mouth seemed relatively ineffective from vapors emanating from a simple bottle. As a fourth drawback, inhaling from a pool of highly volatile fluids on airplanes, in elevators, and in crowded places resulted in others being subjected to the strong vapors of essential oils. Having open bottles of flammable fluids on an aircraft is not reasonable today. Accordingly, the inventors have designed an apparatus that provides very strong vapors that may be inhaled, but which also overcomes the above first, second and third drawbacks.

FIG. 1 shows a section view of an apparatus to conveniently generate vapors from *eucalyptus* oil that may be inhaled without suffering the above three drawbacks. *Eucalyptus* oil is chosen for this preferred embodiment, but the use of other suitable essential oils, such as tea tree oil, are discussed below. The apparatus in FIG. 1 is described as a hand-held "atomizer" that is generally designated with element 2. *Eucalyptus* oil 4 is shown in container 6. A piston 8 having O-ring 10 seals against the interior of the container wall. The atomizer has top element 12 that acts as a "button" (hereinafter "top button 12"), and the container has bottom 14. With one hand, placing the middle finger on the button 12 and the thumb on the bottom 14, and squeezing, produces the vaporized droplets of *eucalyptus* oil. One such droplet of *eucalyptus* oil is designated by numeral 16 that is shown in the location to be inhaled by the user.

The vapors of *eucalyptus* oil may be inhaled through the mouth, or through the nose, or through both. Holding one nostril closed at a time allows selective inhalation through one nostril, and then the other, so that the entire respiratory system may be entirely coated with the thin anti-pathogenic film of *eucalyptus* oil.

In FIG. 1, the atomizer is to be operated "substantially vertically" a term that will be defined below. Pressing down on button 12 increases the air pressure in air pocket 18 above the surface of the *eucalyptus* oil 20. This increasing pressure causes *eucalyptus* oil to flow through first entrance 21 of flexible tube 22 and then to first tube 24 that is in turn connected to the atomizer assembly 26. The first entrance 21 of the flexible tube is reinforced and constructed so that it does not collapse under use, and does not make a positive seal against the interior of the container walls that would interfere with functionality. Pressurized air flows thorough second entrance 28 of the second tube 30 that is in turn also connected to the atomizer assembly 26. Using typical designs for atomizers, and the like, the flow of *eucalyptus* oil and pressurized air into the atomizer assembly 26 generates particles of *eucalyptus* oil in the form of a vapor that pass through the exit passage 32 of the atomizer assembly. The atomizer assembly 26 may have any number of suitable valves, one-way valves, spring actuated valves, spring return valves, ball valves, spring loaded ball valves, breather orifices, etc., which are used in the art to make atomizers, and the like, for the purposes herein, however, those elements are not shown in FIG. 1 solely for the purposes of brevity. Any suitable "atomizer means" may be used for atomizer assembly 26.

In FIG. 1, the vaporized *eucalyptus* oil is injected from the exit passage 32 of the atomizer assembly into a cotton ball 34 whose edges are delineated with dashed lines in FIG. 1.

Therefore, pushing down on button 12 causes vapors of *eucalyptus* oil to be injected into the cotton ball. Then, the vapors diffuse through the cotton ball for subsequent inhalation.

The tapered mouth orifice 36 is used to inhale vaporized *eucalyptus* oil by mouth. As vaporized *eucalyptus* oil and air is inhaled, any additional air required is provided through nostril orifice 38.

Alternatively, nostril orifice 38 is used to inhale vaporized *eucalyptus* oil by one nostril at a time. One nostril is held shut, and the other one is placed against nostril orifice 38 to inhale through a chosen nostril. One after another, both nostrils may be used to suitably inhale vapors of *eucalyptus* oil.

Other details are shown in FIG. 1. The upper body of the hand-held atomizer 40 is a one-piece unit having tapered mouth orifice 36 and nostril orifice 38. The upper body is attached to the piston 8 using typical fabrication techniques. The spacer 42 is designed to guide the main body 40 during its motion, and it serves as a retainer to prevent the piston 8 from inadvertently coming out of the container 6. The spacer 42 may also have one or more check-valves to function as "breathers" when the unit is initially filled with *eucalyptus* oil, respectively enumerated as 44 and 46, however these elements are not shown in FIG. 1 solely for the purpose of brevity. Spacer 42 has suitably close tolerances, or threads as necessary, to positively engage it to container 6.

FIG. 1 shows the position of piston 8 wherein the top portion of that piston is a distance designated by the legend "X" below the lower portion of the spacer 42. As the top button 12 is pushed downward, the piston 8 is also pushed downward thereby compressing spring 48, and the vaporized droplets of *eucalyptus* oil are formed. The "down stroke" causes the top of the piston to move through a maximum, and extreme value, of X. After completing the "down stroke", and upon removing finger pressure from the button, then compression spring 48 returns the top portion of the piston so as to make contact with the lower portion of the spacer 42, which is the "resting position" of the piston. Typical breather holes, one-way valves, such as ball valves, etc., are used to allow air to flow back into air pocket 18, thus preparing for the next "down stroke". Such a breather hole for the purposes herein is shown as element 50 that is located within a portion of atomizer assembly 26. In the "up stroke", and in this embodiment, air can flow into breather hole 50, and thereafter flow through second tube 30 to air pocket 18 thereby allowing the piston to return to its "resting position". Without such a breather hole, or the like, the piston might permanently stay in the "down stroke" position, or might stay in that position until other air leakages allowed the top of the piston to again contact the bottom portion of spacer 42. To achieve this functionality, various different preferred embodiments contemplate using any number of suitable valves, one-way valves, spring actuated valves, spring return valves, ball valves, spring loaded ball valves, breather orifices, etc., which are used in the art to make atomizers, and the like.

In FIG. 1, refilling the atomizer involves removing the spacer 42, removing the piston 8 from the container 6, and refilling the container. The piston 8 is then inserted into the container 6, and the spacer is reinstalled. Yet one or more ball valves in the piston (not shown) may be used to bleed off extra pressure in the event that is necessary during installation of the piston. Any such pressure relief valves shall have the numerals 52 and 54 respectively, but they are not shown in FIG. 1 solely for the purposes of brevity.

The hand-held atomizer overcomes several of the problems cited earlier. In relation to the above defined "first drawback", by using the cotton ball and the apparatus described, no fluids can get sucked up into a nostril. In relation to the above defined "second drawback", no liquids are generated exterior to the hand-held atomizer, so there is minimal chance of getting *eucalyptus* oil into the eyes. Further, the cotton ball also prevents liquids from being squirted directly into the eyes. In relation to the third drawback, the hand-held atomizer provides proper vaporized *eucalyptus* oil for inhalation by mouth. Therefore, the inventors have designed an apparatus and provided methods of operation that provide very strong vapors that may be inhaled, but which also overcome the previously defined first, second and third drawbacks.

There are many variations on the above preferred embodiment. The container 6 may be fabricated from any suitable material, including any type of plastic, or any type of transparent or translucent plastic of any coloration. Transparent or translucent plastics are convenient so that the presence or absence of the *eucalyptus* oil, and the surface of the *eucalyptus* oil 20, may be easily determined by visual inspection. The upper body of the hand-held atomizer 40 having tapered mouth orifice 36 and nostril orifice 38 may be made of any suitable material, including any type of plastic, or any type of transparent or translucent plastic of any coloration. Transparent or translucent plastics are convenient to determine the condition and extent of the cotton ball 34.

For proper operation, the cotton ball 34 should substantially fill and make contact with the interior walls of the upper body of the hand-held atomizer 40. The cotton ball 34 is convenient, but any material may be used as a substitute that has "cotton-ball like qualities" for the purposes of the invention herein that otherwise also avoids the above defined first, second, and third drawbacks. No toxic materials may be used to replace the cotton-ball. Spacer 42 may be fabricated from any material and may be disposed in its location in FIG. 1 using any suitable attachment methods including friction fitting, matching threads, retainer notches, and the like. Any suitable "retainer means" may replace spacer 42.

The dimensions of the nostril orifice 38 are chosen so that it conveniently extends beyond the radial extent of the container 6 and into the nostril for use when held in place by the fingers. The exterior of the container 6 has a first radius R1 (not shown in FIG. 1) that is typically ½ inches, and a first vertical length, or extent, L1 (not shown in FIG. 1) that is typically 1¾ inches tall. Here, the radius is defined as the radial distance away from the vertical axis of the container 6. For the record, FIG. 1 is not to scale. The nostril orifice 38 has a second radial extent R2, (not shown in FIG. 1) that is typically 1¼ inches and a nostril orifice diameter NOD (not shown in FIG. 1) that typically ranges between 3/16 inches O.D. to ¼ inches O.D. for convenient insertion into the nose, but many other dimensions are possible. The diameter NOD is chosen so that the nostril orifice can go into the interior of a typical nostril.

The tapered mouth orifice 36 has a third radial extent R3 (not shown in FIG. 1) that is typically 1½ inches, and an mouth inhalation diameter MID (not shown in FIG. 1) that is typically 1½ inches OD. The tapered mouth orifice may not be circular, and may be any suitably chosen shape to conveniently fit into the mouth. The overall maximum vertical dimension of the hand-held "atomizer", which is the distance between the button 12 and the bottom 14, is typically 3 inches.

In the above, it was stated that the atomizer is to be operated "substantially vertically". The atomizer is to be held in a "substantially vertical orientation" for proper operation. The definition of these terms are as follows. For proper operation, the first entrance 21 of the flexible tube must be immersed in the fluid 4, and must be located below the fluid level 20 so that fluid may be properly atomized ("first condition"). In the above embodiment, the second entrance 28 of the second tube is used to provide air under pressure to the atomizer assembly 26, so that the second entrance 28 must also be located above the fluid level 20 so for proper atomization of the fluid ("second condition"). Lastly, various means, including breather holes and suitable valves, have been described which allow the piston to return from the "down stroke" to its "resting position", and consequently, the orientation of the atomizer in FIG. 1 should be sufficiently vertical so as not to interfere with such means ("third condition"). Any hand-held "atomizer" that is generally designated with element 2 in FIG. 1 that is an orientation such that the first, second, and third conditions are satisfied in this paragraph is in a position that is "substantially vertical". Accordingly, the atomizer is operated "substantially vertically" which is in a "substantially vertical orientation". In general, when the atomizer is held in the hand, its longitudinal axis along its length is at an angle θ with respect to true vertical (which angle is not shown in FIG. 1 for brevity). This longitudinal axis is parallel to the vertical sides of the container 6. The maximum "tilt angle" at which the atomizer fails to meet the first, second, and third conditions depends upon the particular distance from the interior of the bottom of the container to the top of the fluid level 20, when the atomizer is held in the true vertical position, and that particular distance is identified by the legend Y in FIG. 1. Accordingly, there is reason to maintain a reasonable distance between the top of the fluid and the bottom of the piston, and that reasonable distanced is defined by the legend Z in FIG. 1. When X achieves its maximum value in the "down stroke" (XMAX) then Z maintains its minimum value at that position (ZMIN) for any given level of fluid in the container Y for θ=0 degrees. The variables XMAX, ZMIN and θ are not shown in FIG. 1 for the purposes of simplicity. The above comments may be suitably reformulated in terms of the volume of the fluid 4 inside the container 6. For future reference, the inside diameter of the container 6 is the parameter IDC, that is not shown in FIG. 1 for the purposes of brevity.

In earlier disclosure, element 16 was identified as a droplet of *eucalyptus* oil. There are two additional comments here. First, as is typical with most atomizer devices, there is a statistical distribution of droplet sizes and volumes produced depending upon a number of factors including the fluid, its viscosity, the design of the atomizer system, and the force applied to the button 12. The inventors include herein by reference all art in the field related to the production and measurements of such statistical distributions of droplet sizes. Second, any droplet 16 in FIG. 1 may also stand for any other droplet of any other fluid described to this point or hereafter in this application.

There are other variations of the apparatus. The functional elements in FIG. 1 may be reconfigured to fit onto a screw-on cap that in turn screws onto a bottle having *eucalyptus* oil. The bottle may in fact be the original bottle of *eucalyptus* oil that arrived from a manufacturer, so that the refilling process becomes easier. However, this is a minor variation of the invention, and in the interests of brevity, shall not be described in detail.

Tea tree oil may be substituted in the above for *eucalyptus* oil. Put another way, element 4 in FIG. 1 may be chosen to be tea tree oil instead. The use of tea tree oil in the apparatus is similar, except that it is possible that the atomizer assembly 26 may be changed because of the different properties that tea tree oil may have, including different viscosity, density, vapor pressure, etc. Each atomizer assembly may be specifically designed for the oil to be atomized. Each atomizer, or "atomizer means", may in fact be specific to different suppliers of tea tree oil or *eucalyptus* oil in that different suppliers may produce oils having different characteristics as they affect vaporization by the atomizer.

Yet further, element 4 may be chosen to be pure *eucalyptus* oil; pure tea tree oil; any mixture of eucalyptus oil and tea tree oil; any mixture of one or more components from *eucalyptus* oil and one or more components from tea tree oil (which components are defined below); any mixture of *eucalyptus* oil and distilled water; any mixture of tea tree oil and distilled water; and any mixture of *eucalyptus* oil, tea tree oil, and distilled water; and any mixture of the following—(a) one or more components from *eucalyptus* oil and (b) one or more components from tea tree oil and (c) any percentage of distilled water. Therefore, element 4 may be chosen to be any of the above defined fluids in FIG. 1. Element 4 may be chosen to be any essential oil, or any mixture of essential oils, from those listed in the below defined "List of Essential Oils".

In FIG. 1, the cotton ball 34 may be replaced with other substances. For example, the cotton in preferred embodiments can be replaced with plastic material having uniform sized holes. In such a case, the size of the droplet 16 in FIG. 1 may be adjusted in size. Alternatively, the cotton may be removed entirely provided the atomizer assembly 26 in FIG. 1 produces relatively small droplet sizes. Alternatively baffles with holes may be placed across the interior of orifices 36 and 38 to control droplet size. Yet alternatively, if the cotton is removed, the vapor droplets from orifice 38 may be injected into an expansion chamber, where the droplets diffuse, which are in turn inhaled through yet another orifice attached to that injection chamber (not shown in FIG. 1). These are all examples of means to control the droplet size from the hand-held atomizer apparatus. Such means can be used to provide a concentrated stream of essential oil vapors from the hand-held inhaler apparatus. Such means can be used to provide a fine spray of droplets. The size of the droplets can range from the size of molecules to droplets up to 0.050 inches OD.

The device shown in FIG. 1 may also be used to generate an aerosol. According to the Webster's New World™ Dictionary of American English, Third College Edition, edited by Victoria Neufeldt and David Guralnik, Simon & Schuster, Inc., New York, N.Y., 1988 ("Neufeldt and Guralnik, 1988), an entire copy of which is incorporated herein by reference, an "aerosol" is "a suspension of colloidal particles in a gas". If small particles of solid materials are made into a colloidal suspension within the fluid 4 present in FIG. 1, then the hand-held atomizer apparatus in FIG. 1 would produce an aerosol. The small solid materials would be surrounded by fluid as the solid materials would emerge from hand-held atomizer apparatus in the form of droplets. The solid materials dispersed within the fluid within the hand-held atomizer apparatus could be antibacterial drugs, antiviral drugs, or antifungal drugs to be used for specific treatment of diseases in the human respiratory system.

FIGS. 2–6 show another preferred embodiment of the invention.

Figure 2:
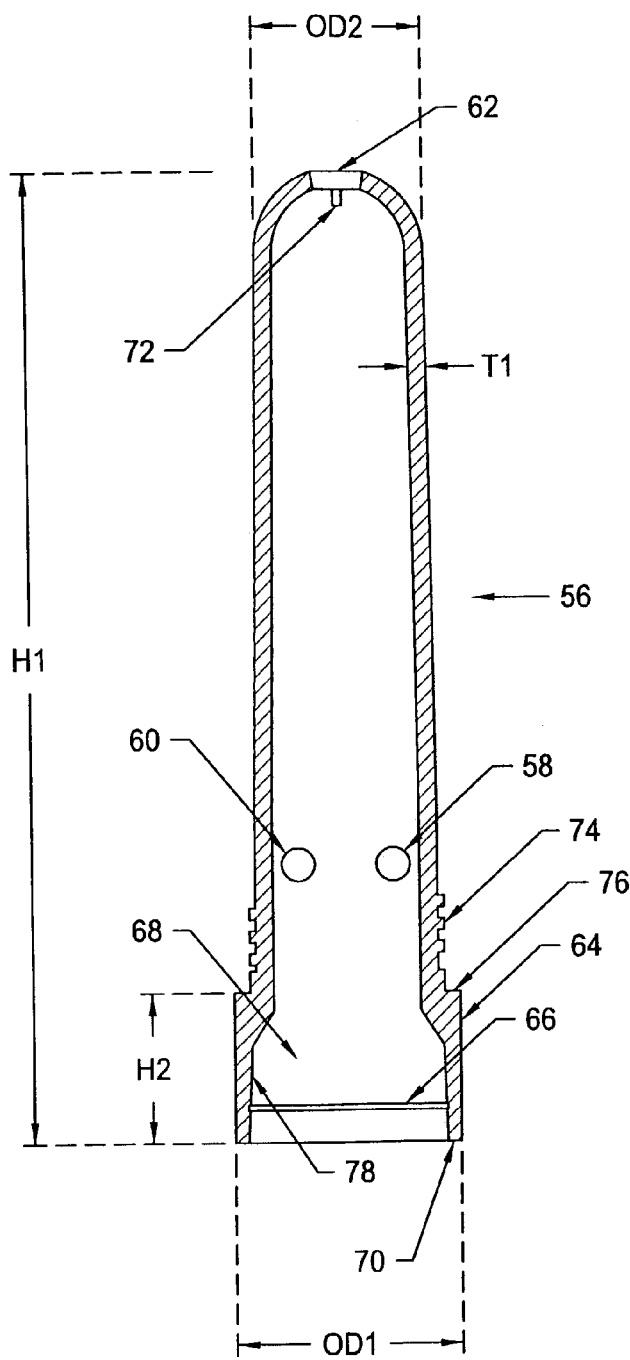
FIG. 2 shows a cross section view of an Inhaler Body.

FIG. 2 shows a cross section view of the Inhaler Body generally designated as element 56. Air inlet holes 58 and 60 allow air to enter the Inhaler Body when it is assembled (see FIG. 5). Vapor outlet orifice 62 allows vapor from the interior of the Inhaler Body to be inhaled into the nose or into the mouth. The Inhaler Body is comprised of a plastic made in an injection mold. The plastic is resistant to essential oils that has a wall thickness shown by the legend T1 in FIG. 2. In one preferred embodiment, the wall thickness T is approximately 0.050 inches. The overall height of the Inhaler Body is shown by the legend H1. In one preferred embodiment, the height H1 is approximately 2.73 inches. The Inhaler Body has hand-held grip 64. In one preferred embodiment, the hand-held grip has fine groves to aid in holding the device, but those fine groves are not shown in FIG. 2 for the purposes of simplicity. The hand-held grip 64 on the Inhaler Body is held by the fingers when inserting the vapor outlet orifice 62 into the nose (or mouth). The outside diameter of the Inhaler Body in the vicinity of the hand-held grip is shown as legend OD1. In one preferred embodiment, OD1 is approximately 0.635 inches. The height of the hand-held grip is shown by the legend H2. In one preferred embodiment, H2 is approximately 0.423 inches. The outside diameter of the upper portion of the Inhaler Body is shown as the legend OD2 in FIG. 2. In one preferred embodiment, OD2 is approximately 0.490 inches as shown in FIG. 2. The upper portion of the Inhaler Body is tapered through a small angle θ so that it can be removed from the injection mold, although that angle is not shown in FIG. 2 for simplicity. Inhaler Plug recession 66 is used to latch the Inhaler Plug into place as further explained in relation to FIG. 3. The Inhaler Plug (shown in FIG. 3) fits within region 68 within the Inhaler Body. The Inhaler Body has lower end 70. The Inhaler Body has internal cross bar 72 for purposes to be described later, and possesses threads 74. The Inhaler Body also has positive sealing surface 76 so that the Inhaler Cap seats in place (see FIG. 6). The Inhaler Body also has positive sealing surface 78 that allows the mating surface of the Inhaler Plug to seat in place (see FIG. 5).

Figure 3:
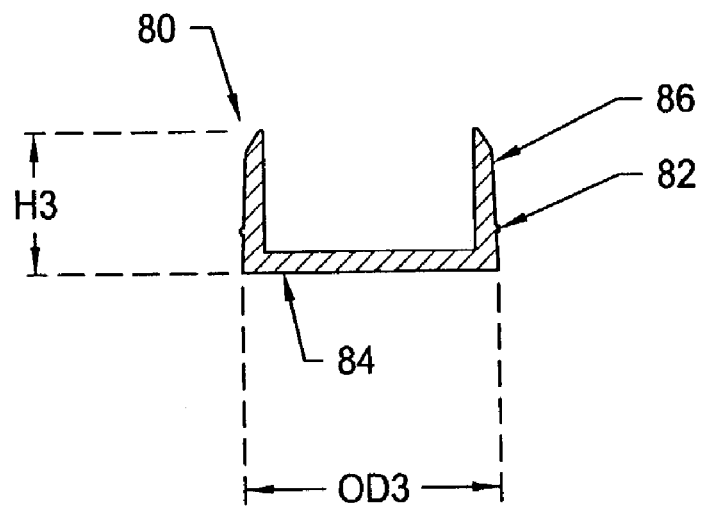
FIG. 3 shows a cross section view of an Inhaler Plug.

FIG. 3 shows a cross section view of Inhaler Plug 80 that possesses extruded ridge 82. The Inhaler Plug 80 is made of plastic in a plastic injection mold that is resistant to essential oils. The Inhaler Plug 80 is forced into the lower end of the Inhaler Body, and fits within region 68 of the Inhaler Body shown in FIG. 2. When pressed into place, the bottom surface 84 of the Inhaler Plug does not protrude below lower end 70 of the Inhaler Body. When pressed into place, the extruded ridge 82 positively "snaps" into place within the Inhaler Plug recession 66 so that it will not fall out of the Inhaler Body. In one preferred embodiment, it takes a minimum force of 20 lbs and a maximum force of 25 lbs to force the Inhaler Plug into place within region 68 of the Inhaler Body. The Inhaler Plug has the height shown by the legend H3 in FIG. 3. In one preferred embodiment, H2 is 0.264 inches. The outside diameter of the Inhaler Plug at the location of its bottom surface 84 is shown by the legend OD3 in FIG. 3. In one preferred embodiment, OD3 is 0.559 inches OD. The dimensions H2 and OD3 are such that the entire Inhaler Plug fits within region 68 of the Inhaler Body in FIG. 2 and does not protrude below the lower end 70 of the Inhaler Body. The Inhaler Plug has positive sealing surface 86 that is used to seat against sealing surface 78 within the Inhaler Body. See FIGS. 5 and 6 for assembly of the Inhaler Plug within the Inhaler Body.

Figure 4:
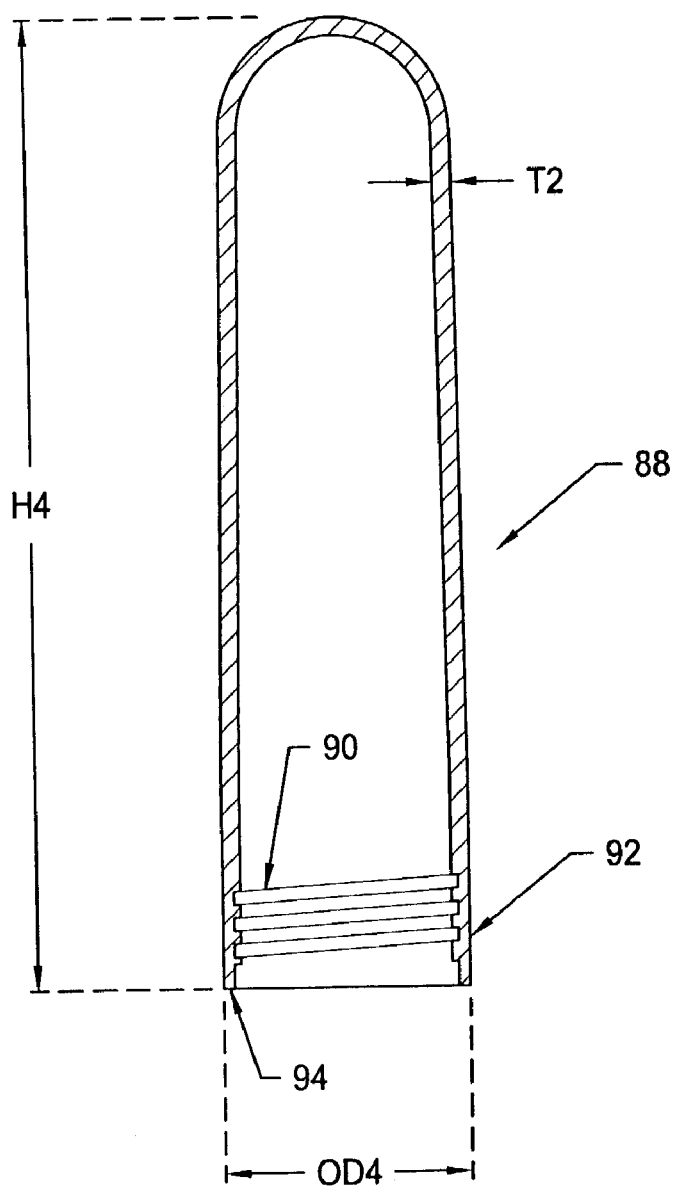
FIG. 4 shows a cross section view of an Inhaler Cap.

FIG. 4 shows a cross section view of the Inhaler Cap 88. The Inhaler Cap is made from plastic in a plastic injection mold that is resistant to essential oils. The Inhaler Cap possesses interior threads 90 that screw onto threads 74 of the Inhaler Body. The wall thickness of the Inhaler Cap is shown by the legend T2 in FIG. 2. In a preferred embodiment, T2 is 0.050 inches. The vertical height of the Inhaler Cap is shown by the legend H4 in FIG. 4. In one preferred embodiment, H4 is 2.43 inches. The Inhaler Cap has lower end 92. At the lower end of the Inhaler Cap, the outside diameter of the Inhaler Cap is shown by the legend OD4 in FIG. 4. In one preferred embodiment, OD4 is 0.642 inches OD. The Inhaler Cap has lower sealing surface 94 that seals against positive sealing surface 76 of the Inhaler Body. A positive seal is necessary to retain the highly volatile essential oils as explained in relation to FIG. 6.

Figure 5:
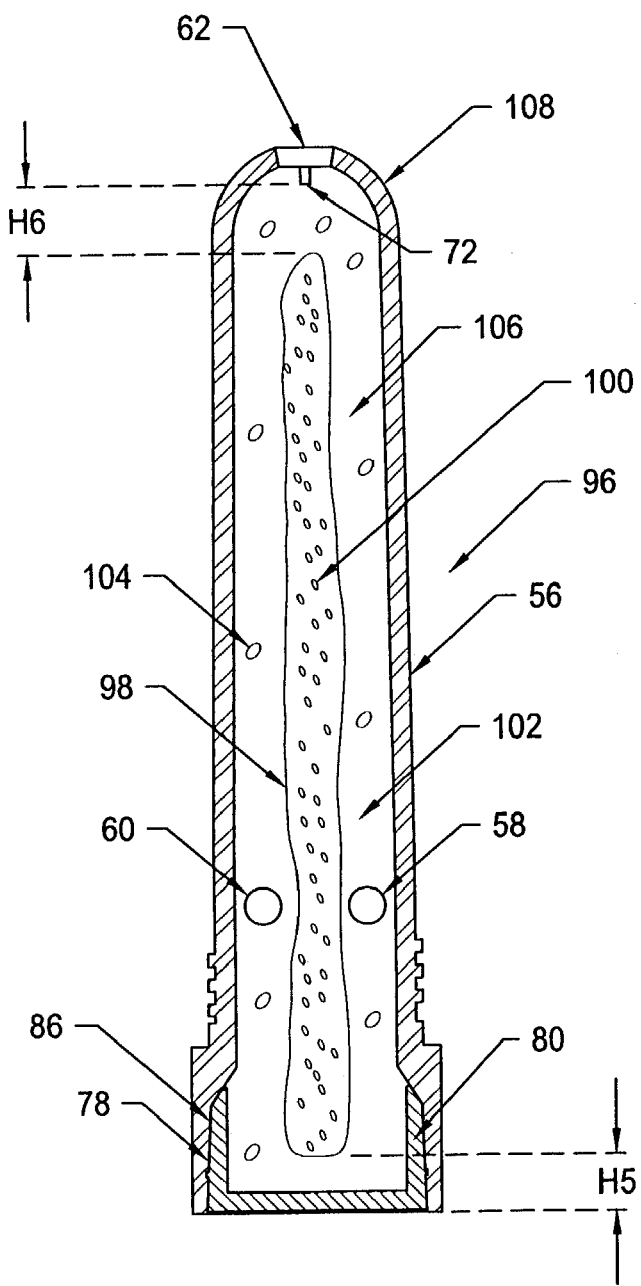
FIG. 5 shows a cross section view of an assembled Inhaler ready to be inserted into the nose.

The cross section of an assembled Inhaler ready to be inserted into the nose or mouth is generally shown as element 96 in FIG. 5. In one preferred embodiment, a pure cotton insert 98 has been soaked in an essential oil shown by element 100. The pure cotton insert is preferably of the type of cotton that is sterile and is free from any chlorine or other chemicals that are sometimes used to bleach cotton white. Examples of the essential oil includes Eucalyptus Oil, Tea Tree Oil, a mix of these oils, or any other essential oil, or mix of those oils, shown in the List of Essential Oils. After the pure cotton insert 98 has been soaked in an essential oil, then it is inserted within the interior of the Inhaler in position 102 that is shown in FIG. 5. Thereafter, the Inhaler Plug 80 is assembled into the Inhaler Body 56. When assembled, the Inhaler Plug has sealing surface 86 that is used to positively seat against sealing surface 78 within the Inhaler Body. These mating surfaces 78 and 86 produce a vapor-tight seal. The vapor-tight seal is necessary to prevent the vapors from the essential oils from escaping through the bottom of the Inhaler. The essential oil 100 has relatively high vapor pressures and evaporate forming an essential oil vapor 104 within the interior chamber 106 of the assembled Inhaler 96.

When inhaling vapors from the Inhaler shown in FIG. 5, the tip of the assembled Inhaler 108 is generally placed near to, or inside, a nostril of the nose. Typically holding the other nostril closed with a finger, the essential oil vapor 104 is inhaled through vapor outlet orifice 62 into the nose, and thereafter into the sinuses, the lungs, and other portions of the human respiratory system. When inhaling from the Inhaler, fresh air is sucked into air inlet holes 58 and 60 which allows the essential oil vapor 104 to travel towards the vapor outlet orifice 62 and into the nose.

The hand-held apparatus in FIG. 5 is a novel device that is used to inhale essential oil vapors. Many devices have been heretofore used to produce vapors from essential oils including placing the oils into boiling water; using aroma lamps (both candle and electric powered); using so-called passive "diffusers" that are often hung around the neck, or hung in cars, which contain essential oils dissolved in other media such as rock salt, clays, sands, fibrous materials, etc.; using aromatherapy discs; using steam vaporizers where essential oils are put into the water of the vaporizer (both "cold" mechanical types and electric heater types); using humidifiers having essential oils; using the direct inhalation of essential oil vapors from bottles; using the inhalation of vapors from essential oils placed on tissue papers; and the inhalation of essential oils into the nose that are rubbed on the hands. When humans inhale vapors from such sources, the dose of the inhaled vapor is extremely variable. However, the Inhaler shown in FIG. 5 provides a much more controlled dose of essential oil vapors. Further, the lung capacity of humans are on the average monotonically related to the size and weight of the individual. Therefore, if a small size person inhales deeply, he or she will obtain a lesser dose of the vapor from the essential oils than will a larger person. Therefore, this embodiment of the Inhaler has the virtue that is provides a dose that is related to the weight of the individual, other factors being held constant. Further, with the preferred embodiment shown in FIG. 5, for any one individual, he or she can determine how to replicate the effective amount of vapor to inhale. Such replication is not possible with other means of inhaling essential oil vapors. Accordingly, a virtue of the Inhaler shown in FIG. 5 is that any one individual may consistently, from one day to the next, obtain a controlled amount of vapor from the essential oils. In the field of aromatherapy, the lack of devices to administer relatively controlled doses has been a significant problem. Therefore, the preferred embodiment of the Inhaler shown in FIG. 5 is able to provide relatively controlled doses of vapors from essential oils, and this is a major innovation and a major improvement in the field of aromatherapy.

After extended usage, the amount of vapor within the Inhaler decreases. Accordingly, using techniques described below in relation to FIG. 6, the position of the cotton insert may be adjusted towards the tip of the assembled Inhaler 108 or towards the Plug 80 in the Inhaler. Legends H5 and H6 define the relevant distances in FIG. 5. If H5 is 0 inches, then the vapor inhaled through vapor outlet orifice 62 is minimized. If H6 is 0 inches, then the vapor inhaled through vapor outlet orifice 62 is maximized.

In FIG. 5, it is also worth point out that the internal cross bar 72 has an important purpose. If H6 is 0, then the upper portion of the cotton insert 98 rests against the cross bar 72. In this position, if a baby inadvertently sucks on the vapor outlet orifice 62, then the baby cannot suck out the cotton insert 98. This is important because although essential oil vapors might not harm a child, if a child instead were to inadvertently ingest the essential oil 100 within the cotton insert 98, then it could cause potential poisoning of the infant. If the cross bar 72 were not in the position shown, then it might be possible for a baby to suck the cotton insert out through the vapor outlet orifice 62.

As the temperature of the cotton insert 98 having essential oil 100 increases, then the vapor pressure of the volatile essential oils increase, and stronger vapors may be inhaled through the vapor outlet orifice. Individuals may learn to obtain consistent doses at room temperature. Then again, if the individual carries the Inhaler in his or her pocket, he or she may learn to adjust the dosage for the higher temperature.

Figure 6:
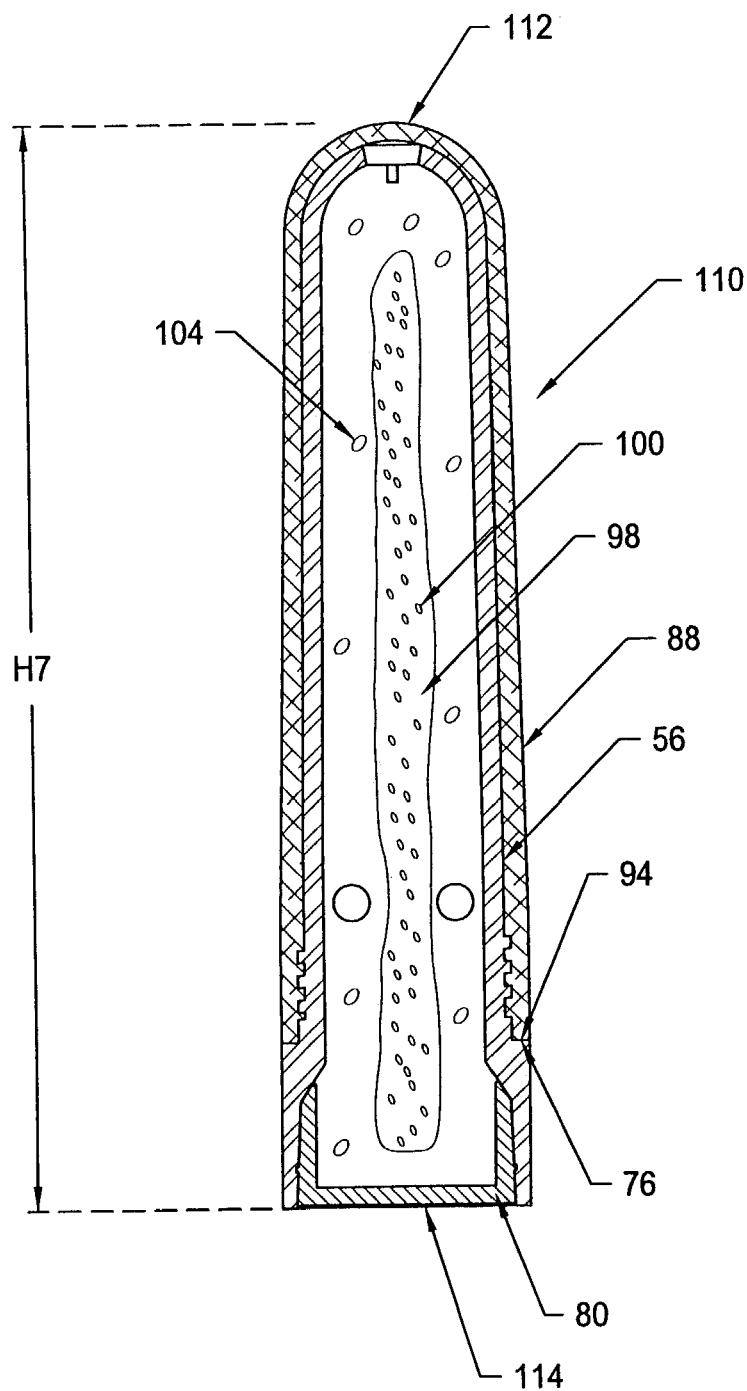
FIG. 6 shows a cross section view of an Inhaler with its cap assembled in place.

FIG. 6 shows the cross section of an Inhaler with its cap assembled in place that is generally designated by element 110. If the Inhaler in FIG. 5 is left out in the air, the vapors will eventually evaporate out of the Inhaler through its vapor outlet orifice 62. So, for storage of the Inhaler, the Inhaler Cap must be installed. FIG. 6 shows the Inhaler Body 56, the Inhaler Plug 80, the Inhaler Cap 88, the cotton insert 98 that has been soaked in an essential oil 100, and the essential oil vapor 104. The overall height of the Inhaler with its cap installed is defined to be the legend H7. In the preferred embodiment herein H7 is approximately 2.85 inches. It is now evident why the positive sealing surface 76 of the Inhaler Body must make a good seal against the lower sealing surface 94 of the Inhaler Cap when the Cap is "torqued down" by finger tightening. If this seal fails, then the highly volatile essential oil vapors can leak out of the Inhaler with the Inhaler Cap installed.

In FIG. 6, the top portion of the Inhaler Cap is identified with element 112. If this top portion is "tapped" onto the surface of a table, then H6 identified in FIG. 5 will go to 0 inches, and after removal of the Inhaler Cap, the inhaled vapor will be more concentrated. In FIG. 6, the bottom portion 114 of the Inhaler is identified with element 114. If this bottom portion is "tapped" onto the surface of a table, then H5 will go to 0 inches, and after removal of the Inhaler Cap, the inhaled vapor will be less concentrated.

In FIGS. 5–6, the pure cotton insert 98 may be replaced by any suitable material. The essential oil 100 is held within the cotton insert under its own surface tension. So, any porous material of any type that is sterile, and which will hold the essential oil under its own surface tension can be used to substitute for pure cotton insert 98 in FIGS. 5–6. There are many possibilities. Many different fibrous mediums which are sterile may be used. For example, hollow fibrous tubes may be used. In yet another embodiment, a small atomizer assembly may be suitably attached to the an insert that replaces insert 98 in FIGS. 5–6. These improvements provide means to control the droplet size of the essential oil vapor (that shown as element 104 in FIG. 5) that is produced from the hand-held inhaler apparatus. Such means may be used to provide a more potent, or concentrated, steam of essential oil vapors from the hand-held inhaler apparatus.

Figure 7:
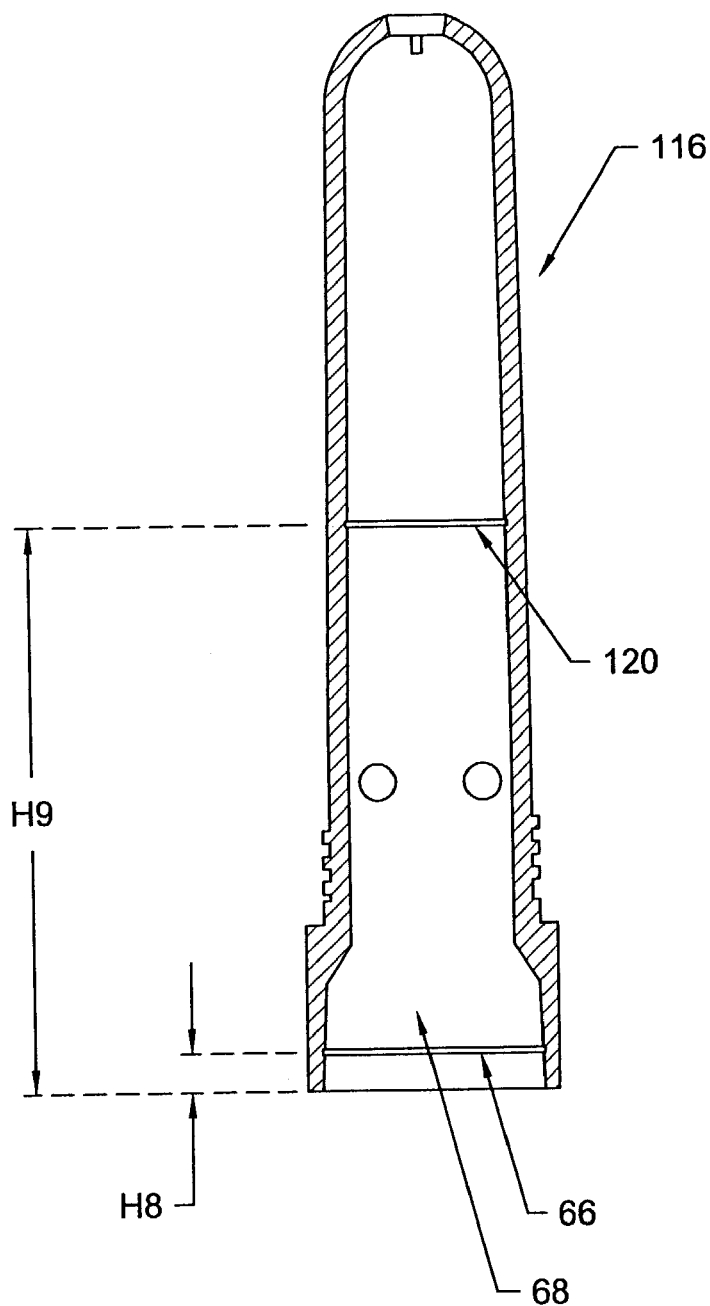
FIG. 7 shows another cross section view of an Inhaler Body with provision for the installation of a Separator.

FIG. 7 shows the cross section of another preferred embodiment of an Inhaler Body generally designated by element 116. This Inhaler Body 116 is identical to the Inhaler Body 56 in FIG. 2 except Inhaler Body 116 has an additional recession in the interior wall of the Inhaler Body called the Separator recession. FIG. 7 shows the Inhaler Plug recession 66 at the position designated by legend H8 that is identical to that of Inhaler Body 56 shown in FIG. 2. FIG. 7 shows the Separator recession 120 at the vertical position designated by legend H9. This Separator recession 120 is the new additional recession. The Inhaler Plug 80 of FIG. 3 fits within region 68 of Inhaler Body 116.

Figure 8:
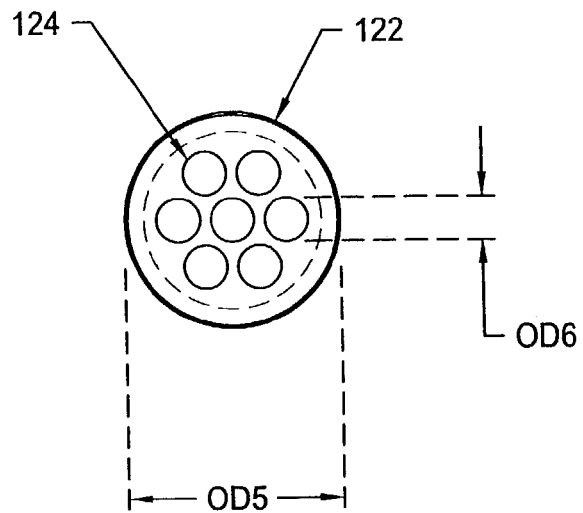
FIG. 8 shows the top view of a Separator.

FIG. 8 shows the top view of Separator 122. It has an approximate outside diameter shown by the legend of OD5 in FIG. 8. In the preferred embodiment shown in FIG. 8, the Separator has a total of 7 breather holes. One such breather hole is labeled with element 124. Each such breather hole has an outside diameter of OD6.

Figure 9:
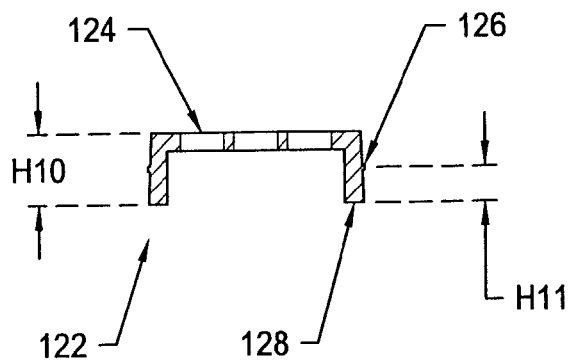
FIG. 9 shows a cross section view of a Separator.

FIG. 9 shows the cross section view of Separator 122. A side view of breather hole 124 is also shown in FIG. 9. The height of the Separator is shown by the legend H10 in FIG. 9. The Separator possesses extruded ridge 126. The extruded ridge 126 is a distance defined by the legend H11 above the lower edge 128 of the Separator.

Figure 10:
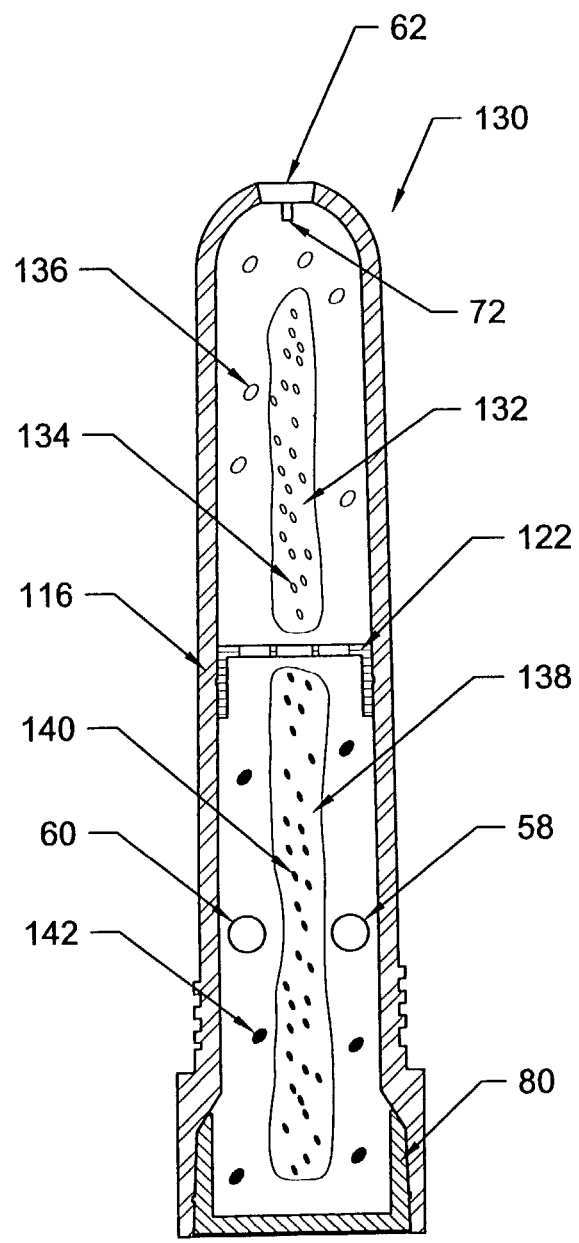
FIG. 10 shows a cross section view of an assembled Inhaler with an installed Separator.

FIG. 10 shows the cross section view of an assembled Inhaler with Separator installed that is generally shown as element 130. The Inhaler shown in FIG. 10 is assembled as follows. Upper cotton insert 132 is soaked in first essential oil 134 which is then installed within Inhaler Body 116 that produces first essential oil vapor 136. Then the Separator 122 is installed within Inhaler Body 116. During this installation, the extruded ridge 126 of the Separator (in FIG. 9) is snapped into place into the Separator recession 120 (in FIG. 7) within the Inhaler Body 116. Then lower cotton insert 138 is soaked in second essential oil 140 that is then installed within the Inhaler Body 116 that produces second essential oil vapor 142. Then Inhaler Plug 80 is installed within Inhaler Body 116.

For use, the vapor outlet orifice 62 is typically inserted into one nostril, with the other nostril held closed with a finger. As an individual inhales, a mixture of vapors from first essential oil vapor 136 and second essential oil vapor 142 are inhaled into the lungs. Air flows into the Inhaler Body 116 through air inlet holes 58 and 60 and through the breather holes in the Separator. This design is particularly useful if first essential oil 134 is chemically or physically reactive with second essential oil 140. The separated chambers allow the combination of vapors to be inhaled from essential oils that may be otherwise chemically or physically reactive. First essential oil 134 may be any pure essential oil or any mixture of those essential oils found in the List of Essential Oils. Second essential oil 140 may be any pure essential oil or any mixture of those essential oils found in the List of Essential Oils.

Figure 11:
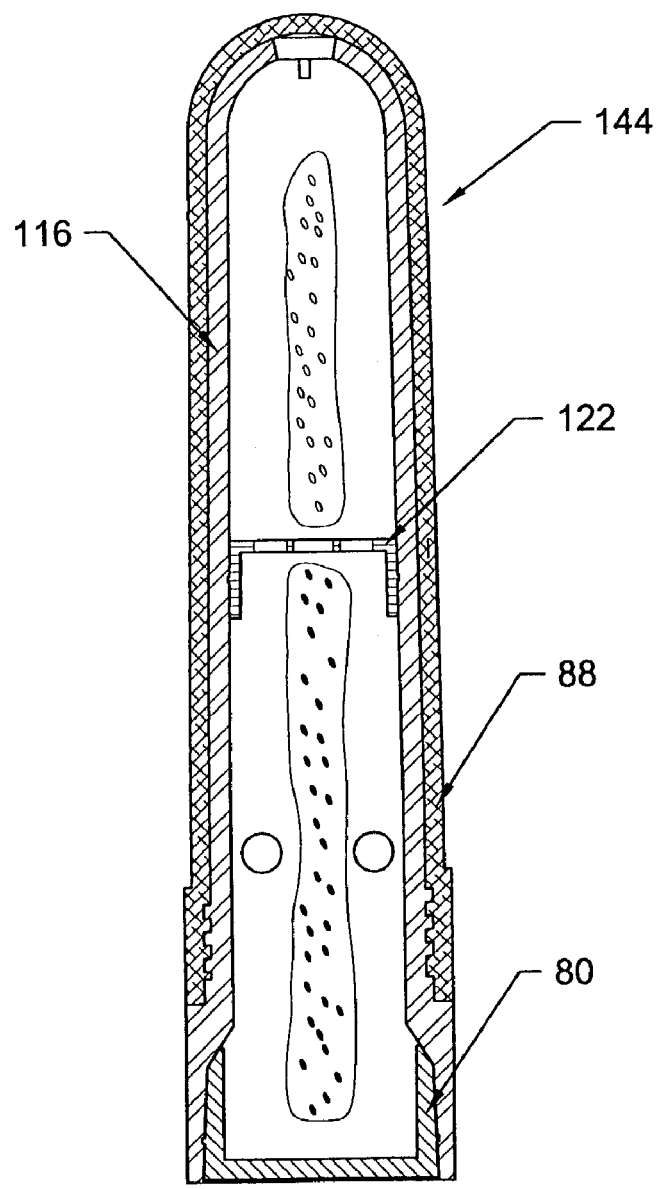
FIG. 11 shows a cross section view of an assembled Inhaler with a Separator installed and with the Inhaler Cap installed.

FIG. 11 shows the cross section view of the Inhaler in FIG. 10 with Inhaler Cap 88 properly installed for long term storage that is generally designated with element 144. The other elements shown in FIG. 11 have been previously defined in relation to FIG. 10.

From the above description, it is evident that two or more Separators may be used in Inhalers. Therefore, Inhalers may be fabricated having three or more separate cotton inserts in different portions of the Inhaler. Each such cotton insert can be soaked in a different essential oil, or combination of essential oils. Therefore, Inhalers have been described that have two or more cotton inserts within different chambers separated by two or more Separators. Further, different separators can be designed that are "Longitudinal Separators", which separate cotton inserts longitudinally. In such a case, different portions of the Inhaler are divided into different azimuthal sections. However, these are minor variations of the preferred embodiment of the invention.

The apparatus described in FIGS. 1, and FIGS. 2–11, are all embodiments of hand-held inhalers, hand-held inhaler apparatus, hand-held inhaler devices, hand-held atomizer apparatus, and hand-held inhaler means. So, the apparatus in FIG. 5 can be called a hand-held inhaler, a hand-held inhaler apparatus, a hand-held inhaler device, a hand-held atomizer apparatus, or a hand-held inhaler means. Examples of "at least one orifice attached to a hand-held atomizer apparatus" are either element 36, or element 38, in FIG. 1. Another example of "at least one orifice attached to a hand-held atomizer apparatus" is the vapor outlet orifice 62 in FIG. 2. Similarly, these elements 36, 38, and 62 may also be described as "at least one orifice attached to a hand-held inhaler".

In several preferred embodiments, *eucalyptus* oil is the essential oil from *Eucalyptus globulus*. In other embodiments, *eucalyptus* oil may mean any oil in the eucalyptus family including *Eucalyptus globulus*, *Eucalyptus smithii*, etc.

List of Subsections

Several additional topics are discussed below in individual subsections as they relate to the invention respectively entitled as follows:
"Baseline Activities";
"Composition of *Eucalyptus* Oil";
"Comments About *Eucalyptus* Oil";
"Composition of Tea Tree Oil";
"Comments About Tea Tree Oil";
"Essential Oils";
"List of Essential Oils"
"*Eucalyptus* Oil, Tea Tree Oil, and Prevention of Infections of Circulatory System and Prevention of Heart Attacks";
"Methods to Reduce Infections Following Operations";
'The Phrase "To Prevent"';
"Test Chamber";
"List of Pathogens";
"Tuberculosis";
"Opportunistic Infections by Pathogens in Lungs of Patients Having with Cystic Fibrosis";
"Inhaled Anthrax, Smallpox, Botulism, Plague, Tularemia, Hemorrhagic Fever Viruses, Tuberculosis and Other Inhaled Bioterrorism Pathogens";
"Sinusitis";
"Rhinitis";
"Asthma";
"Pneumonia";
"Respiratory Viral Infections";
"Reference on Essential Oil Vapors and Respiratory System Pathogens";
"Severe Acute Respiratory Syndrome (SARS)";
"Advantages of Inhaled Antiseptics to Prevent, Treat and Cure Respiratory Diseases Including SARS";
"Inhalation, Inc.";
"Use of Essential Oils in Nebulizers";
"Measurements of Interest";
"Unknown Respiratory Pathogens"
"Applicable Portions of the Anatomy and Related Maladies"
"Summary of Preferred Embodiments"; and
"References".

Baseline Activities

During the initial experiments lasting some six months commencing in September of 1999, the first inventor also did some other "baseline activities" that were important to maintain good lung health. To control his asthma, he inhaled twice a day Alupent® and Flovent® for the typical medical reasons. Further, the first inventor raised the head of his bed by about 4 inches to prevent gastric juices and related gasses from entering the respiratory system while sleeping. It may turn out that these "baseline activities" are important to the methods set forth in preferred embodiments of this invention. Usual experimental techniques will be used to determine their importance if necessary. As another statement of fact, the first inventor most often inhaled *eucalyptus* oil, but also often inhaled tea tree oil during this trial period. Another aspect of the invention includes the method of using *eucalyptus* oil and/or tea tree oil in combination with the use of Alupent® and Flovent® to prevent colds, flus, and pneumonia in individuals having asthma.

Prior to the inventor's routinely using the invention, the first inventor often inhaled Alupent® about 6 times a day and Flovent® about 6 times a day. If the first inventor stopped the use of these inhalers, he could hardly breathe about 3 days later. During a series of experiments, the first inventor actually gave up the use of both of these asthma inhalers for a duration of 4 months. However, thereafter, the first inventor began to notice that his breathing was gradually becoming shallow. So, the first inventor began a regimen where he simply inhales Alupent® one time in the morning each day, and Flovent® one time in the morning every day. Those inhalers are left at home during the remainder of the day, and the first inventor instead uses the invention herein. This regimen has worked for the first inventor for over 3½ years as of the filing of this application herein. This approach has helped the first inventor to substantially avoid the well known side effects of asthma inhalers that are described in the book by Michael T. Murray, N. D., entitled "Natural Alternatives to Over-the-Counter and Prescription Drugs", William Morrow and Company, Inc., New York, N.Y., 1994, (Murray, 1994) an entire copy of which is incorporated herein by reference. In particular, please refer to Chapter 7 entitled "Asthma, Hay Fever, and Antihistamine Medications" in Murray, 1994.

Composition of Eucalyptus Oil

The chemical composition of *eucalyptus* oil is complicated and is known. There are various varieties, including oil from *Eucalyptus australiana*. See Hedges and Wilkens, 1991, an entire copy of which is incorporated herein by reference describes oil from that species. Page 345 of this reference states in part:

"Analysis of *Eucalyptus* oil, like that of any complex mixture, presents difficult problems not only in the separation but also in identification of components. Terpenes and terpene derivatives constitute the bulk of the oil (1,2) and, due to the inherent flexibility of the isoprene units which comprise the compounds, the oil contains many closely related isomers and homologs. Further characterization reveals that 40–80% of the oil is composed of one compound, 1,8-cineole, thus presenting the choromatographer with a large sample dynamic range problem."

Hedges and Wilkens, 1991, on page 345, further state: "A *Eucalyptus australiana* oil sample was obtained . . . ".

Hedges and Wilkens, 1991, on page 346, further state: "Fifty-eight peaks were counted in the chromatogram of *E. Australiana.*"

Hedges and Wilkens, 1991, on page 347, in "Table 1. Component identification by CG-IR-MS*" list the following compounds as being present, or likely present, in Eucalyptus oil: α-pinene; 1,8-cineole; limonene; α-terpinene; 2,3-dimethylcyclohexanol; cis-linalool oxide; terpinolene; ρ-cymenene; α-pinene oxide; linalool; isopentyl isovalerate; fenchyl alcohol; α-campholenal; 3,3,6,6-tetramethyltricyclo [3.1.0.02.4]hexane; trans-verbenol; 2,5-dimethyl benzaldehyde; borneol; 4-terpineol; 1-methyl phenyl ethanone; α-terpineol; α-hexyl cinnamaldehyde; 4-isopropenyl-1-methy cyclohexenel; para-mentha-1(7),8,10-dien-9-ol; ρ-carvone; 1-methylethyl-2-methylene cyclohexanone; geraniol; isoborneol acetate; α-terpinenyl acetate; β-patchoulene; geranyl η-propionate; β-gurjunene; aromadendrene; and allo-aromadendrene. Different preferred embodiments of this invention contemplate using one or more of the above components in any proportion to achieve the desired results. Further, all routine techniques used in the medical and biological sciences are incorporated herein by reference, and these standard techniques may be used to identify one or more of the above compounds as being the active ingredients to obtain the desired results. Once so identified, the individual compound or mixture of compounds are merely different preferred embodiments of the invention disclosed herein.

Further information concerning the detailed chemical analysis of *eucalyptus* oil are provided in references 1–25 on page 350, of Hedges and Wilkens, 1991, and entire copies of all such 25 references are incorporated herein by reference.

An earlier reference, Gunther, 1948, provided an older list of ingredients of *eucalyptus* oil. An entire copy of Gunther, 1948, is incorporated herein by reference. In particular, see pages 437–525, of Volume IV of this reference. For different varieties of *eucalyptus* oils, and sources for those oils, please also see Schnaubelt, 1998; Lawless, 1999; and Rose, 1999; entire copies of which are incorporated herein by reference.

Comments about Eucalyptus Oil

Balch and Balch, 1997, page 69, state under "Action and Uses" for *eucalyptus* oil the following: "Clears congestion, has a mild antiseptic action, and reduces swelling by helping to increase blood flow. Relaxes tired and sore muscles. Good for colds, coughs, and other respiratory disorders." This reference on page 69, also states under "Comments" concerning *eucalyptus* oil: "Recommended for external use only. It should not be used on broken skin or open cuts or wounds."

Miller and Miller, 1995, state on page 251, the following: "*Eucalyptus* is one of the most commonly used essential oils. You could write a book on all its uses. There are over 700 varieties of eucalyptus, some growing to 500 feet, and they all possess similar properties. It is currently used in many allopathic medical preparations. It is one of the three best oils for use with any respiratory tract problems because the component eucalyptol is mucolytic (it relaxes the flow of mucous) and it excretes the eucalyptol out though the lung surface. Even if you take it internally in tea form, eucalyptus will very quickly pass out of the body through the lungs, having its relaxing effect to the mucous membranes. As it is inhaled it gives an immediate effect; then again as it circulates out of the body." This reference further recites certain additional formulas "including rosemary and camphor". This reference further states with regards to "Actions": "diaphoretic, decongestant, stimulant, antiseptic, antispasmodic, alternative, diuretic, expectorant, antipyretic, regenerative, lowers blood sugar, disinfects the air, increases concentration, deodorant, germicidal".

Fugh-Berman, 1997, on page 194, states the following warnings about potential toxicity: "Essential oils should only be taken orally under the supervision of a practitioner experienced in their use. Tea Tree oil and *eucalyptus* oil have been associated with childhood poisonings, [Jacobs, Webb] and ingestion of pennyroyal oil has killed at least two adults. [Sullivan, Vallance] Essential oils are safe to use topically if diluted (and a few are safe full-strength)." These references are listed below under "References" so that the interested reader can further investigate the toxicity of *eucalyptus* oil and other essential oils.

Only AFTER the inventors had conceived the inventions herein, and only AFTER the personal trials conducted by the first inventor had been completed, the inventors found a hard-to-locate newsletter entitled "Alternatives For the Health Conscious Individual", written by Dr. David G. Williams. In particular in the October, 1999 issue of Williams, 1999, on page 25, Dr. Williams states in part: "The essential oil extracted from the leaves has long been used in cough drops and cold medications, mouthwashes, toothpaste, detergents, and liniments for arthritis pain." This reference further states on page 25: "In fact, millions of people take advantage of eucalyptus' antimicrobial properties each day by swishing with that old medicine chest staple, Listerine." That reference on page 25, also states: "Thanks in large part to the eucalyptus, Listerine is a very potent germ-killer . . . " This article further states that Listerine® "can kill 60 percent of the HIV virus it touches within 30 seconds. In this same time period, Listerine killed 100 percent of the bacteria *Staphylococcus aureus* present."

Williams, 1999, page 26, then recounts several anecdotal stories. In one, and during a trip to Australia when "the winter flu season was in full swing", he noticed that almost everyone he "encountered had succumbed to this flu with the notable exception of two cleaning ladies" each of which "carried a small rag that had been doused with the oil of eucalyptus". In their presence, the "fumes were very strong . . . ".

Williams, 1999, page 26, then recounts a discussion with the above cleaning ladies: "When I questioned the ladies, they told me that one of their grandfathers had used *eucalyptus* oil to ward of flu since World War I. At that time, a military base had apparently experienced a flu epidemic so sever the soldiers were dying from it. To stop the problem, authorities sealed off one of the barracks and sprayed down the interior with *eucalyptus* oil. Then they placed all the solders in that building for a day. That action reportedly stopped the epidemic in 24 hours."

Williams, 1999, page 26, further states: "*Eucalyptus* oil can be toxic if taken internally, but breathing the oil's fumes will likely allow its bactericidal components to knock out infections in the nasal passages, sinuses, bronchial tubes, and lungs." Williams, 1999, page 26, then suggests by analogy to carrying around rags soaked with *eucalyptus* oil that it "can actually prevent the flu", but he gives no mechanism for doing so, and provides no methods of doing so— except carrying around rags soaked with *eucalyptus* oil or soaking a room like the barracks with the oil. Williams, 1999, page 26, further states: "I'am currently investigating a very unusual eucalyptus variety that is non-toxic when taken orally. If it checks out, this development will open up all kinds of fantastic medicinal possibilities." Apparently, Dr. Williams is primarily concerned with orally taken medication.

Therefore, Williams, 1999, states or implies that *eucalyptus* oil may be effective against certain viruses and against certain bacteria. However, the methods set forth in Williams, 1999, of providing such vapors to human beings are not practical in their normal lives. Normal human beings cannot carry around rags soaked with *eucalyptus* oil that would produce odors offensive to others. Nor is it practical to lock people up in a barracks or other rooms washed down with *eucalyptus* oil. Several preferred embodiments of this invention are provided to overcome these problems.

Williams, 1999, does NOT describe the methods or apparatus disclosed in the preferred embodiments herein. Williams, 1999, does not describe directly inhaling the fumes periodically from an inhalant device as a method to prevent infection. Williams, 1999, does not describe any type of thin anti-pathogenic layer or barrier that substantially prevents the initial infection of colds flus, and other pathogens for a period of time following the inhalation of *eucalyptus* oil. Williams, 1999, does not describe the proposed use of *eucalyptus* oil as a prophylactic agent to prevent the initial infection of tuberculosis. Williams, 1999, does not describe methods of infection proposed by the inventor involving a "likely pathogenic invasion site", and the use of inhaled vapors of *eucalyptus* oil to decrease the risk of invasions or infections of such sites by pathogens. Nor does Williams, 1999, describe the possibility that infectious diseases may involve the progression of colonies of pathogens vs. time that may involve viral, bacterial, and fungal elements defined earlier as "symbiotic pathogens", and that the initial infection of these pathogens may be prevented by the periodic inhalation of strong vapors from *eucalyptus* oil.

Further, Williams, 1999, does not describe any method to reduce the risks of infection of the human respiratory system by pathogens that includes at least the step of the inhalation of concentrated vapors from *eucalyptus* oil immediately before entering an enclosed public area having one or more human beings within the enclosed area.

Still further, Williams, 1999, does not describe the method to prevent the initial infection of the human respiratory system by pathogens causing diseases such as colds, flus and pneumonia, that includes at least the step of inhaling concentrated vapors of *eucalyptus* oil to form an anti-pathogenic barrier inside the human respiratory system that is effective for a period of time of at least 30 minutes following the inhalation. Nor does Williams, 1999, describe periodic inhalations of vapors from *eucalyptus* oil to maintain the anti-pathogenic barrier inside the human respiratory system.

Another reference, Igram, 1992, page 18, states the following:
"*Eucalyptus* oil is used for the purpose of healing the respiratory passages, and the amount that actually entered the tissues is minimal."

Schnaubelt, 1998, describes in on pages 31–40, and elsewhere, the antibacterial, antiviral, and antifungal effects of certain essential oils. For example, Schnaubelt, 1998, page 33, refers to another study which showed that various essential oils had varying effectiveness against different pathogens including "*Pneumococcus* spec., *Klebsiella pneumoniae, Staphylococcus aureus haemolyticus, Neisseria catarrahalis, Streptococcus haemolyticus, Proteus vulgaris, Haemophilus influenzae, Haemophilus pertusis*" and "*Candida albicans,* and *Escherichia coli*—Aerobacter group, various *Cornybacteria, Listeria*".

Composition of Tea Tree Oil

The chemical composition of tea tree oil is complicated and is known. See Swords and Hunter, 1978, an entire copy of which is incorporated herein by reference. Page 734 of this reference states in part:
"Australian tea tree oil (*Melaleuca alternifolia*) was fractionated by column chromatography and analyzed by combined gas chromatograhy-mass spectrometry. Preparative GLC of selected fractions yielded pure compounds for analysis by infrared and nuclear magnetic resonance spectroscopy. Forty compounds were identified, including viridiflorene which has not previously reported as occurring in nature."

Swords and Hunter, 1978, on page 734–735, further state:
"The chemical composition of tea tree oil has been previously investigated by the Instrumental Laboratories of Fritzsche Brothers, Inc.; New York, and the following components were reported (Gunther, 1968): $\alpha$-pinene, 2.2%; $\alpha$-terpinene, 7.5%; limonene, 1.0%; 1,8-cineole, 5.6%; $\gamma$-terpinene, 17.5%; $\rho$-cymene, 3.0%; terpinolene, 3.1%; 1-terpinen-4-ol, 44.9%, $\alpha$-terpineol, 5.2%; aromadendrene, 21.7%; two unknown sesquiterpenes, 1.6% each."

Swords and Hunter, 1978, on page 737, show "Table I" which presents the list of compounds present, or suspected to be present, in tea tree oil as follows: 1. $\alpha$-Pinene; 2. Camphene; 3. $\beta$-Pinene; 4. Sabinene; 5. Myrcene; 6. $\alpha$-Phellandrene; 7. 1,4-Cineole; 8. $\alpha$-Terpinene; 9. Limonene; 10. 1,8-Cineole; 11. $\gamma$-Terpinene; 12. p-Cymene; 13. Terpinolene; 14. Hexanol; 15. Allyl hexanoate; 16. $\rho,\alpha$-Dimethylstyrene; 17. a Sesquiterpene; 18. $\alpha$-Cubebene; 19. a Sesquiterpene; 20. $\alpha$-Copaene; 21. Camphor; 22. $\alpha$-Gurjunene; 23. Linalool; 24. a Sesquiterpene; 25. Unidentified; 26. 1-Terpineol; 27. 1-Terpinen-4-ol; 28. $\beta$-Elemene; 29. Caryophyllene; 30. a Sesquiterpene; 31. Aromadendrene; 32. $\beta$-Terpineol; 33. Alloaromadendrene; 34. Unidentified; 35. Humulene; 36. Unidentified; 37. $\gamma$-Muurolene; 38. $\alpha$-Terpineol; 39. Viridiflorene; 40. Piperitone; 41. $\alpha$-Muurolene; 42. Piperitol; 43. Unidentified; 44. $\sigma$-Cadinene; 45. 4,10-Dimethyl-7-isopropyl [4.4.0]-1,4-decadiene; 46. Nerol; 47. 8-$\rho$-Cymenol; and 48. Calamenene. Capital letters were used here for various compounds because they were so listed in Table 1 in Swords and Hunter, 1978.

Lawless, 1994, pages 22–23, states the following:
"The Australian standard for *Melaleuca alternifolia* oil now requires that the terpinen-4-ol content of the oil should be greater than 30 percent, and the cineole content less than 15 percent. A top quality tea tree oil should, however, have a maximum cineole content of 5 percent and a minimum terpinen-4-ol content of 35–40 percent. As the demand for tea tree has increased, the essential oil has also been increasingly subjected to adulteration, usually with cineole—the main constituent of *eucalyptus* oil which gives *eucalyptus* oil its characteristic camphor-like scent." This reference further goes on to state: "The balance of the main constituents in a fresh, high quality tea tree oil should be approximately as follows: Alpha-pinene 2.5 percent; Alpha-terpinene 9.1 percent; Para-cymene 3.9 percent; 1,8-cineole 4.3 percent; Gamma-terpinene 24.6 percent; Alpha-terpineol 2.3 percent; Terpinen-4-ol 42.1 percent; (and) Terpinolene 4.1 percent."

In the above quotation from Lawless, 1994, pages 22–23, the ';' and the word 'and' were added to the previous quote to make it readable solely for the purposes of brevity in accordance with rules of the USPTO for specification.

A more recent reference was obtained from the internet concerning the constituents of tea tree oil. This was obtained from the company called "Hans-Dieter Knoch Tea Tree Export" on Mar. 9, 2000 at the world-wide web address of "www.midcoast.com" that lists the following ingredients as a "Typical Analysis" from Batch No. HK008: alpha-pinene 1.3%; sabinene 1.3%; alpha-terpinene 9.4%; Limonene 1.1%; p-cymene 2.5%; 1,8 cineole 2.9%; gamma-terpinene 20.2%; terpineolene 3.4%; Terpinen-4-ol 38.2%; alpha-terpineol; 2.4%; Aromadendrene 2.4%; Ledene 1.4%; delta-cadinene 1.6%; Glubolul 0.5%; and Viridiflorol 0.4%.

Comments about Tea Tree Oil

It is of interest to note that item 21 in Table I of Swords and Hunter, 1978, (discussed above) is "Camphor", that is specified as one ingredient in Mentholatum® Ointment. However, the statement on a container of this ointment in the possession of the inventors reads as follows: "Gentle aromatics help relieve stuffy noses, chest congestion, sinus congestion, head colds, chest colds, and muscular aches due to coughs and colds." The label on the container does NOT make any statement about prevention of colds or flus by using the product.

Fugh-Berman, 1997, page 193, states the following: "Tea tree oil is widely used as an antibacterial and antifungal topical medication, and several studies indicate its effectiveness. One compared pure tea tree oil and the antifungal drug clotrimazole for treatment of fungal infection of the toenails. After six months, the two treatments were found to be equally effective. [Buck]"

Lawless, 1994, on pages 25–26, states the following:
"Due to its unique composition, tea tree oil displays a number of remarkable properties making it very effective for a wide range of complaints. Foremost among these properties, and what makes tea tree oil outstanding in comparison to other remedies, is that it is active against all varieties of infections organisms: bacteria, fungi and viruses. Independent microbiological testing has confirmed the effectiveness of tea tree oil against a wide range of micro-organisms, notably:
Gram Positive bacteria: *Staphyloccus aureus, Staphyloccus epidermidis, Staphyloccus pneumoniae, Staphyloccus faecalis; Staphyloccus pyrogenes, Staphyloccus agalactiae, Propionibacterium acnes, Beta haemolytic streptococcus*
Gram Negative bacteria: *Escherichia coli, Klebsiella pneumonia, Citrobacter* spp., *Shigella sonnei, Proteus mirabilis, Legionella* spp., *Pseudomonas aeruginosa*
Fungi: *Trichophyton mentagrophytes, Trichophyton rubrum, Aspergillus niger, Aspergillus flavus, Candida albicans, Microspourm canis, Microsporum gypseum, Thermoactinomycetes vulgaris.*"

Lawless, 1994, page 26, further states:
"Tea tree's effectiveness in fighting infection is further backed up by its ability to stimulate the immune system—this means that if the body is threatened by any of these organisms, tea tree increases the body's own ability to protect itself and to respond appropriately. Tea tree oil's main areas of activity may therefore be summarized as: antiseptic/bactericidal, anti-fungal, anti-viral, and immuno-stimulant."

Regarding the antiviral properties of tea tree oil, Lawless, 1994, page 27, states:
"Viruses are the invading organisms responsible for most epidemic illnesses. As a powerful anti-viral agent, tea tree is effective in fighting many common infectious diseases such as measles, chickenpox, flu, colds and shingles as well as other viral complaints such as cold sores, veruccae and warts."

Regarding the immuno-stimulant properties of tea tree oil, Lawless, 1994, pages 27–28, further states:
"In this context, tea tree is principally of great value as a preventative remedy—to help the body fight off all kinds of infection. This is especially important if the body is already in a weakened condition brought on by either stress, illness or the use of anti-biotics or other drugs which have lowered the body's natural resistance levels. Tea tree has been found to be especially helpful for those who need to have their strength built up, such as before a surgical operation or for those suffering from chronic or long-standing debilitating illnesses such as glandular fever or hepatitis. Its possible application to AIDS is also currently being researched."

Lawless, 1994, on pages 18–24, describes the chemical make-up of tea tree oil. On page 20, it states in part: "In its natural state, tea tree oil is an extremely complex chemical substance containing at least 48 organic compounds. The main constituents are terpenes, pinenes, cymones, terpineols, cineole, sesquiterpines and sesquiterpinene alcohols—however, it also contains four constitutions that are rarely found elsewhere in nature: viridiflorene (approximately 1 percent), B terpineol (0.24 percent), L-terpineol (trace) and allyhexanoate (trace).[1]" The reference cited at the end of this quote is Swords and Hunter, 1978, although the recitation is misspelled in Lawless, 1994 on page 112.

Following a percentage break-down of substances within tea tree oil, Lawless, 1994, on page 23, further states:
"It is interesting to note that none of the these substances is especially effective alone. It is only in combination that these substances demonstrate their maximum healing power—which is known as a 'synergy'. This is a quality common to many essential oils, where the unique balance of constituents, including the trace elements, contributes to the overall effectiveness of the remedy. This factor also helps to account for why synthetically produced products, or 'nature-identical' oils, cannot match properties exhibited by the naturally derived original, since it is very difficult to mimic the complex and diverse blend of components found in nature."

Igram, 1992, on page 17, states in part: "It should be emphasized that tea tree oil is an antiseptic." Igram, 1992, further states: "This is not to suggest that tea tree oil is exceptionally toxic when taken internally. There are no deaths on record from internal use or accidental overdose."

Igram, 1992, further states on page 17:

"Tea tree oil finds its greatest usage as a remedial agent for diseases affecting the exposed surfaces and mucous membranes. It can be safely used in small doses on all mucous membranes, including the gums, oral mucosa, vagina, urethra, colon and rectum. Although internal ingestion has been attempted without noticeable toxic effects, this is not enough evidence to warrant its widespread use internally."

With regards to the respiratory system, Igram, 1992, page 18, states with regard to tea tree oil: "It can be inhaled to help relive bronchial congestion and to aid in opening clogged sinus passages."

Further, tea tree oil penetrates tissues deeply. Regarding this subject, Igram, 192, page 54, states the following:

"One of the major obstacles in eradicating Candida infections, as well as other fungal infections, is getting the medicine to penetrate deep enough into the site of the invention. If a person weeds a garden by mowing the weeds only, they will grow right back. The cure is achieved by digging the weeds out by the roots, or in today's age, destroying the roots with chemicals. In a similar manner it is crucial to utilize medicines which penetrate as deeply as possible into the skin and mucous membranes. This is precisely the advantage of tea tree oil. It has the greatest penetrating capacity of any known antifungal agent. As it saturates the tissues, it kills fungal organisms on contact."

However, Olsen, 1991, points out that under apparently comparatively rare circumstances, that there are adverse affects related to the use of tea tree oil. For example, on page 14, of Olsen, 1991, it states the following: "Tea Tree Oil was tested recently in 1991 in a family practice office. Fifty patients with various skin problems were chosen at random." The reference continues with: "One patient dropped out of the study and a second discontinued due to a mild erythematous skin sensitivity to the 100% oil. This was the only side-effect reported." The reference further states: "The results of using the Tea Tree Oil were striking. All the patients but one were cured or showed remarkable improvement of the conditions treated."

Olsen, 1997, page 11, states the following:

"ISO Standard 4730 states that tea tree oil should be extracted from *Melaleuca alternifolia, Melaleuca linafolia,* or *Melaleuca dissitifolia* species of the Myrtaceae family. Other tea tree species, including Cajuput (*Melaleuca Cajuputi*), New Zealand Manuka (*Leptospermum scoparium*), New Zealand Ti-Tree (*Cordyline australis*), and Kanuka (*Leptospermum ericoides*) are not highly regarded, as they do not contain the same anti-microbial benefits, nor have they been in use for nearly a century as has *Melaleuca alternifolia.*"

Further, Olsen, 1997, on page 12, presents typical "Analytical Results" that presents the chemical composition and percentages present for a sample from the Australian Plantations, Jul. 17, 1997, which is incorporated herein by reference.

Yet further, Olsen, 1997, on page 83, states the following:

"Action. Pure tea tree oil conforming to Australian standard A.S.D. 175, revised 1985 (AS 2782-1985) and 1996 (ISO 4730) is a powerful broad-range antiseptic, fungicide, and bactericide. The main component is terpinen-4-ol (T-4-ol). Optimal activity at 35–40% w/v. Its bacterial actions is increased in the presence of blood, serum, pus, and necrotic tissue. It is able to penetrate deeply into infected tissue and pus, mix with these, and cause them to slough off while leaving a healthy surface. The oil has a very low toxicity, and is virtually a non-irritant event to sensitive tissues. Because of its lower cineole level, tea tree oil is less toxic and less irritating that *eucalyptus* oil. Be aware that some unknown *eucalyptus* oils have been blended with a synthetic form of terpinen-4-ol, which alters the chemical composition."

Essential Oils

The "essential oils" are defined on page 63, of Balch and Balch, 1997, as follows:

"Essential oils are derived from herbs or other plants through steam distillation or cold pressing. They are usually mixed with a vegetable oil or water, and used either as a mouth, ear, or eye wash, or as an inhalant, douche, or tea. These oils can also be used externally in massage or on burns and abrasions. Essential oils readily combine with the natural fats present in the skin. With few exceptions, such as the use of camphor, eucalyptus, or tea tree oil for certain skin conditions, essential oils should always be diluted in either water or oil before being applied to the body, and they should not be taken internally except under the direction of a physician trained in their use."

Prime examples of essential oils are *eucalyptus* oil and tea tree oil. In one preferred embodiment of the invention, vapors are alternatively inhaled, first from *eucalyptus* oil, and then from tea tree oil, to prevent colds, flu, and the like. This is the so-called "alter method" of using essential oils. The rationale for using such an approach is to avoid a build-up of immunity developed by organisms to just one substance. Further, *eucalyptus* oil may preferentially affect one set of pathogens, and tea tree oil may affect another set of pathogens, in a complex disease that may have bacterial, viral, and fungal elements.

Different embodiments of the invention contemplate using any essential oil known that has at least the following properties: it is non-toxic when inhaled; and it has anti-pathogenic properties. Many such essential oils are listed in Gunther, 1948; in Schnaubelt, 1998; in Lawless, 1999; in Olsen, 1997; and in Rose, 1999.

In addition to mixtures of essential oils that may substitute for element 4 in FIG. 1 that have already been listed above, element 4 in addition may be chosen to be any one of the following: any mixture of *eucalyptus* oil with tea tree oil; any mixture of *eucalyptus* oil with one or more other essential oils; any mixture of tea tree oil with one or more other essential oils; any mixture of *eucalyptus* oil, tea tree oil, with one or more other essential oils; any mixture of *eucalyptus* oil, tea tree oil, one or more essential oils, and distilled water; any mixture of (a) one or more components from *eucalyptus* oil, (b) one or more components from tea tree oil and (c) one or more components from any other essential oil; and any mixture of (a) one or more components from *eucalyptus* oil, (b) one or more components from tea tree oil, (c) one or more components from any other essential oil, and (d) any portion of distilled water. Typical procedures in the art may be used to determine the optimum percentage mixtures of any of the above components to prevent colds, flus, and infections of the human respiratory system. Therefore, element 4 in FIG. 1 may include any of the above listed fluids.

For the purposes herein, the term "essential oils" include all ingredients from the plant *Lomatium dissectum*. This plant was referred to in Schnaubelt, 1998, on page 39, with the following quote:

"As shown by Indians of the Pacific Northwest, placing more faith in a much broader effectiveness of essential oils against viral illnesses is more justified than the paucity of scientific studies would suggest. These Indians were able to protect themselves against the devastating consequences of the worldwide flu epidemic of 1918 with a preparation made from a native plant, *Lomatium dissectum*[8]." Here, the superscript refers to Alstat, 1987.

The following is a list of "essential oils". For the purposes of this application, this is called the "List of Essential Oils". The scientific name is on the left-hand side, and the common name appears in parentheses.

List of Essential Oils

*Abies alba* (Fir, Silver)
*Abies balsamica* (Fir, Balsam)
*Abies grandis* (Fir, Grand)
*Abies siberica* (Fir, Siberian)
*Achillea millefolium* (Yarrow, Blue)
*Amni Visnaga* (Amni Visnaga)
*Angelica archangel* (*Angelica* Seed)
*Angelica archangel* (*Angelica* Root)
*Aniba roseodora* (Rosewood)
*Anthemis nobilis* (Camomile, Roman)
*Apium graveolens* (Celery)
*Artemisia dracunculus* (Tarragon)
*Artemisia Herba Alba* (Mugwort, White, Thujone)
*Betula alleganiensis* (Birch, Yellow)
*Boswellia frerana* (Frankincense)
*Cananga odorata* (Ylang Ylang)
*Canarium luzonmicum* (Elemi)
*Carum carvi* (Caraway)
*Cedrus deodara* (Cedar, Himalayan)
*Cedrus atlantica* (Cedar, Atlas)
*Cinnamonum camphora* (Camphor)
*Cinnamonum zeylanicum* (Cinnamon Bark)
*Cistus landi.* var. *pinene* (*Cistus* [Rockrose])
*Citrus aurantifolia* (Petitgrain, Lime)
*Citrus aurantifolia* (Lime)
*Citrus aurantium* (Orange, Sweet)
*Citrus aurantium amara* (Neroli)
*Citrus aur. bergamia* (Bergamot)
*Citrus aur. bigarade* (Orange, Bitter)
*Citrus aur. bigarade* (Petitgrain, Bigarade)
*Citrus limonum* (Lemon, Yellow)
*Citrus paradisi* (Grapefruit)
*Citrus paradisii* (Grapefruit Pink)
*Citrus reticulata* (Petitgrain, Mandarine)
*Citrus reticulata* (Tangerine)
*Citrus reticulata* (Mandarine, Red)
*Citrus sinensis* var. (Orange, Red)
*Coriandrum sativum* (Coriander)
*Cupressus* (Cypress)
*Cymbopogon citratus* (Lemongrass)
*Cymbopogon flexuosus* (Lemongrass)
*Cymbopogon martini* (Palmarosa)
*Cymobopogon nardus* (Citronella)
*Daucus carota* (Carrot Seed)
*Eletteria cardamomum* (Cardamon)
*Eucalyptus citriadora* (*Eucalyptus citriadora*)
*Eucalyptus globulus* (Eucalyptus, Sweet)
*Eucalyptus radiata* (*Eucalyptus radiata*)
*Eucalyptus smithii* (*Eucalyptus smithii*)
*Eugenia caryophyllata* (Clove Bud)
*Ferula Galbaniflua* (Galbanum)
*Foeniculum dulce* (Fennel, Sweet)
*Gaulteria fragrantissima* (Wintergreen)
*Helichr. ital.* var. *serot.* (Helichrysum Serotinum)
*Hypericum perforat.* (St. John's Wort)
*Hyssopus off.* var. *dec.* (Hyssop, Decumbens)
*Hyssopus officinalis* (Hyssop)
*Inula graveolens* (*Inula*, Extra Fine)
*Iris Pallida* (*Iris* [Orris])
*Jas. offic. sambac* (Jasmine Sambac)
*Jasminum grandiflor.* (Jasmine, Grandiflorum)
*Juniperus communis* (Juniper, Berry)
*Juniperus com.* var. *alp.* (Juniper, Alpine)
*Juniperus virginiana* (Cedar, Virginia)
*Laurus nobilis* (Bay Laurel)
*Lavandula angustifolia* (Lavender)
*Lavandula hybrida* (Lavandin, Sweet)
*Lavandula latifolia* (Lavender, Spike)
*Lavendula officinalis*
*Lavandula officinalis* var. *veraE* (Lavandin, Sweet)
*Lavandula officinalis* var. *vera* (Lavender, Extra)
*Lippia citriodora* (Lemon Verbena)
*Litsea cubeba* (Litsea cubeba)
*Majorana hortensis* (Marjoram, Sweet)
*Matricaria chamom.* (Camomile, Ger.)
*Melaleuca alternifolia* (Tea-Tree)
*Melaleuca quinquinervera* (Niaouli)
*Melissa officinalis* (Melissa [Lemon Balm])
*Mentha piperita* (Peppermint)
*Mentha silvestris* (Mint, Forest)
*Mentha spicata* (Spearmint)
*Myristica fragrans* (Nutmeg)
*Myrtus communis* (Myrtle, Green)
*Myrtus communis* (Myrtle, Red)
*Nardostachys jatamansi* (Spikenard [Nardo])
*Ocimum basilicum* (Basil, Holy)
*Ocimum basilicum* (Basil, Tropical)
*Ocimum basilicum* (Basil, Sweet, Linalol)
*Ocotea cymbar* (Sassafras)
*Origanum compactum* (Oregano)
*Origanum vulgare* (Oregano)
*Pelargonium graveolens* (Geranium)
*Pelargonium roseum* (Geranium, Rose)
*Petroselinum crispum* (Parsley Seed)
*Pimenta racemosa* (Bay Leaf)
*Pimpinella anisum* (Anise)
*Pinus nigra* (Pine, Black)
*Pinus nigra, pinaster* and *sylvestris* (Pine des Alpes)
*Pinus sylvestris* (Pine Sylvestre)
*Piper nigrum* (Pepper, Black)
*Pistacia lentiscus* (Mastic)
*Pogostemon cablin* (Patchouli)
*Poliantes tuberosa* (Tuberose)
*Pseudotsuga menzesieii* (Fir Douglas)
*Ravensara aromatica* (Ravensare)
*Rosa damascena* (Rose Otto)
*Rosa damascena* (Rose
*Rosmarinus officinalis* (Rosemary)
*Salvia lavandulifolia* (Sage, Spanish)
*Salvia officinalis* (Sage)
*Salvia sclarea* (Clary Sage)
*Santalum album* (Sandalwood, Tamil Nadu)
*Satureia montana* (Savory)
(?) (Sea Pine)

*Styrax benzoe* (Benzoin resinoid 50%)
*Syzygium aromaticum* (Clove)
*Tagetes patula* (Tagetes)
*Tanacetum annuum* (Camomile, Blue)
*Tsuga canadensis* (Spruce, Hemlock)
*Thymus mastichina* (Marjoram, Spanish)
*Thymus satureioides* (Thyme Borneol)
*Thymus serpyllium* (?)
*Thymus vulgaris* (Thyme Linalol)
*Thymus vulgaris* (Thyme Thujanol)
*Thymus zygis* (Thyme, Red, Thymol)
*Vanilla Planifolia* (*Vanilla*)
*Vetiveria zizanoides* (Vetiver)
*Zingiber officinale* (Ginger, CO2)

As used herein, the above defines specific essential oils. For example, the scientific name *Eucalyptus globulus* is the name given a specific tree. The leaves from this tree are typically steam distilled to make the essential oil from that tree. So, the essential oil is made from the tree called *Eucalyptus globulus*. However, for the purposes herein, the inventors also call the essential oil made from this tree also simply "*Eucalyptus globulus*". Therefore, this scientific name can be used interchangeably for the name of the tree and for the name of the essential oil produced from the leaves and other components of the tree. Similar comments apply to the other scientific names above which can be used as the name of the species of the plant or tree, or as the name of the essential oil produced from the plant or tree. This definition specifically applies to the language used in any claims granted in a patent that might issue based upon this specification.

Various embodiments of the invention contemplate using the vapors from any one of the above essential oils. Other embodiments contemplate using the vapors from a mixture in any relative proportion of two of the above listed essential oils. Yet other embodiments contemplate using the vapors from a mixture in any relatively proportion of two or more of the above essential oils.

*Eucalyptus* Oil, Tea Tree Oil, and Prevention of Infections of Circulatory System and Prevention of Heart Attacks Several studies have been performed involving the expectorant effects of various essential oils. See Schnaubelt, 1998, pages 39–40, that describes results from several other references. A relevant point for this analysis is that a "clinical study determined the terpine levels in blood of test subjects after they inhaled essential oils." That reference further states: "Within thirty to forty minutes the concentration of essential oils absorbed through inhalation sinks to half its original value. This demonstrates that there is no danger of accumulating essential oils in the body even with repeated uses."

Further, Schnaubelt, 1998, on pages 98–99, shows that the inhalation of essential oils results in essential oils being provided to the "heart-lung-circulatory system". Recent literature points to irritations, or inflammations, of the circulatory system caused by unknown pathogens as being associated with certain forms of heart disease. For example, according to page A7, of The Seattle Times, Friday, Mar. 24, 2000, researchers identified "levels of C-reactive protein (CRP)" as an indicator for heart attacks. This article states "The protein indicates if arteries are inflamed."

To my knowledge, the quoted researchers do not know what pathogens cause the inflammation in the circulatory system. However, since *eucalyptus* oil and tea tree oil have antibacterial, antiviral, and antifungal properties, no matter what the type of pathogen is involved, then the periodic inhaling of concentrated vapors from *eucalyptus* oil and/or tea tree oil may be used as an effective preventative measure against the development of this type of heart disease and the resulting heart attacks.

Therefore, inhaled vapors from *eucalyptus* oil and tea tree oil enter the blood stream and are useful to reduce the inflammation caused by pathogens to reduce the probability of heart attacks.

Further, a preferred embodiment of the invention is a method to reduce inflammation of the human circulatory system caused by pathogens to prevent heart attacks that includes at least the step of inhaling concentrated vapors of *eucalyptus* oil so that the oil enters the circulatory system, whereby the tea tree oil possesses antibacterial, antiviral, and antifungal properties useful to reduce any the inflammation.

Another preferred embodiment is the method to reduce inflammation of the human circulatory system caused by pathogens to prevent heart attacks that includes at least the step of inhaling concentrated vapors of tea tree oil so that the oil enters the circulatory system, whereby the tea tree oil possesses antibacterial, antiviral, and antifungal properties useful to reduce any the inflammation.

Similar comments apply to other essential oils that are non-toxic when inhaled, that possess antibacterial, antiviral, and antifungal properties useful to reduce any inflammation within the circulatory system.

Methods to Reduce Infections Following Operations

A major cause of deaths in hospitals in the United States are attributed to infections following operations. For example, see the book entitled "To Err is Human, Building a Safer Health System", "Advanced Copy", published by the Institute of Medicine, National Academy of Sciences, that is listed under Kohn, et al., 1999 in the "References" below. Perhaps a dear cousin in my family fell victim recently to such an infection. A device similar to the atomizer shown in FIG. 1 could be used to reduce the probability of infection following many operations. In this case, nostril orifice 38 could be blocked off, or it could instead attached to a sterile source of flowing gas, such as air or nitrogen.

This preferred embodiment provides the method to generate and cause a mist of droplets of tea tree oil and distilled water to flow to the open wound in the human body during major surgery. The tea tree oil and distilled water mist would form an antibacterial, antiviral, and antifungal barrier against infection from the dreadful types of infections pathogens present in typical operating rooms. Other embodiments contemplate using various different mixtures of tea tree oil, other essential oils, and distilled water.

The Phrase "to Prevent"

The above disclosure has described methods to prevent the initial infection of the human respiratory system by pathogens causing diseases such as colds, flus and pneumonia, that includes at least the step of inhaling concentrated vapors of *eucalyptus* oil to form an anti-pathogenic barrier inside the respiratory system that is effective for a period of time of at least 30 minutes following the inhalation.

The above disclosure has also described methods to prevent the initial infection of the human respiratory system by pathogens causing diseases such as colds, flus and pneumonia, that includes at least the step of inhaling concentrated vapors of tea tree oil to form an anti-pathogenic barrier inside the respiratory system that is effective for a period of time of at least 30 minutes following the inhalation.

The above paragraphs have used the word "prevent". In typical drug tests regulated by the FDA (the Food and Drug Administration), Phase I, Phase II, Phase III, and sometimes, Phase IV trials are carried out. See page 16, of FughBerman, 1997. The word "prevent" is often used herein in a statistical manner. As pointed out on pages 11–13, of Fugh-Berman, 1997, a drug must provide benefit that is "statistically significant" over the so-called "placebo effect", where subjects report improvements in up to ⅓ of the cases. In several of the preferred embodiments, the word "prevent" means to provide "statistically significant" benefits against infection over the so-called "placebo effect".

Because of the statistical nature of the word "prevent", several of the above embodiments describe methods to reduce the risks of infection of the human respiratory system by pathogens that includes at least the step of the inhalation of concentrated vapors from *eucalyptus* oil immediately before entering an enclosed public area having one or more human beings within the enclosed area.

In the previous paragraph, pathogens include viruses, bacteria, fungi, tuberculosis, and infectious agents causing pneumonia.

One way to conduct trials on the above methods to prevent diseases are "randomized trials". See Fugh-Berman, 1997, page 12. For example, during the next flu season, perhaps 10 children's day care centers could be chosen. Then, on a random basis, ½ of the teachers in the children's day care centers could periodically inhale *eucalyptus* oil and/or tea tree oil to prevent colds and flus. Then, the results could be compared to the ½ of the teachers that did not do so. Then, the same group could be swapped. Standard statistical analysis can then be used to determine the statistical effectiveness of the preventative methods.

In several embodiments above, it is stated that *eucalyptus* oil and/or tea tree oil provide a barrier against infection by pathogens. These barriers include a direct barrier, but also include other "barrier-like effects". The inhaled oils soak into the cells within the respiratory system that provides additional protection against infection by pathogens. The oils reduce any pre-existing infection caused by pathogens, and therefore, in conjunction with the immune system, again provides additional protection against infection by pathogens. The oils help mucous membranes repair themselves, and so this effect also provides additional protection against infection by pathogens. The oils help repair many types of existing damage and therefore, this effect also provides additional protection against infection by pathogens.

Test Chamber

Heretofore, standard techniques have been used to measure the antipathogenic properties of essential oils. These methods generally employ the physical contact of the test essential oil with the test pathogen. Typically, a culture of bacteria is grown in a medium in a petri dish, and then filter paper soaked in an essential oil is placed on top of the culture. If the essential oil is effective, then the bacteria are killed out to a certain radius away from the filter paper soaked in the essential oil. For further references on such techniques, please refer to the chapter entitled "The Aromatogram" on pages 33–36 of Schnaubelt, 1998, an entire copy of which is incorporated herein by reference. Typical results from those tests appear in the table entitled "Effectiveness of Essential Oils Against Microorganisms" on page 35 of Schnaubelt, 1998, an entire copy of which is incorporated herein by reference.

Many different references are cited on the subject of testing the antipathogenic properties of essential oils in the book entitled "Aromatherapy for Health Professionals, by Shirley Price and Len Price, Second Edition, Churchill Livingstone, New York, N.Y., 1999 ("Price and Price, 1999"), an entire copy of which is incorporated herein by reference. In particular, please see pages 66–68 of Price and Price, 1999. Table 4.4 on pages 70–71 of Price and Price, 1999, shows typical results for the antibacterial properties of selected essential oils, an entire copy of which is incorporated herein by reference. Table 4.5 on page 73 of Price and Price, 1999, shows typical results for the antifungal effects of selected essential oils, an entire copy of which is incorporated herein by reference. Table 4.6 on page 75 of Price and Price, 1999, shows typical results for the antiviral properties of selected essential oils, an entire copy of which is incorporated herein by reference.

Additional references on the antipathogenic properties of essential oils are provided on pages 91–102 of Schnaubelt, 1999, an entire copy of which is incorporated herein by reference.

As previously stated, the above cited reference generally describe the physical contact of the test essential oil with pathogens under test. However, a new test is required that tests the antipathogenic properties of the vapors from essential oils on selected pathogens. That is the purpose of the apparatus shown in FIG. 12.

Figure 12:
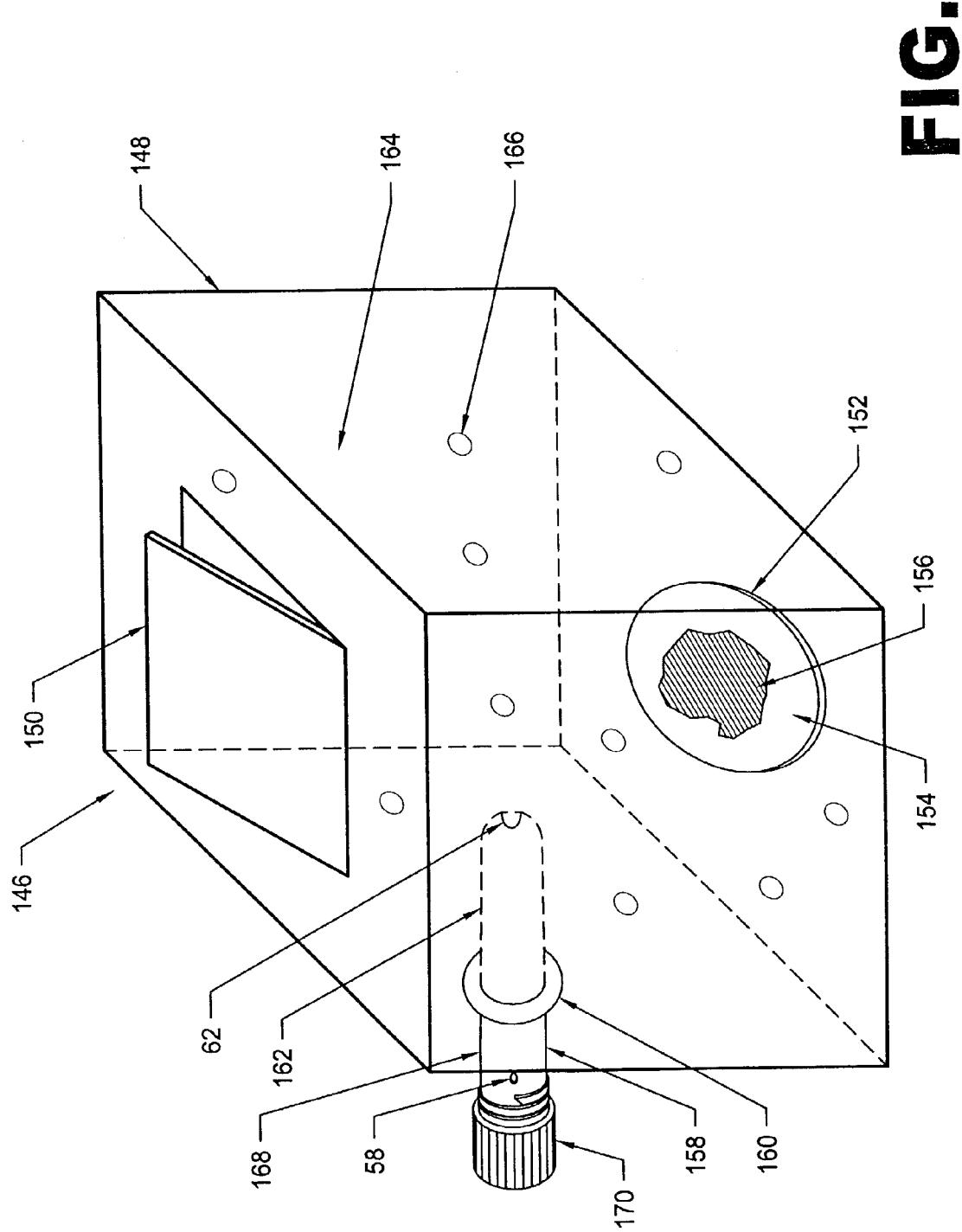
FIG. 12 shows a perspective view of the Inhaler Test Chamber to test the sensitivity of pathogens to vapors produced within an Inhaler.

FIG. 12 shows a perspective view of the Inhaler Test Chamber 146. A sealed test chamber 148 has an access door 150. FIG. 12 shows this access door in the open position. However, during tests of pathogens, this access door is in the closed position. A petri dish 152 contains a suitable pathogen growing medium 154 on which is grown a test pathogen 156 such as-anthrax (*Bacillus anthracis*), for example. A Test Inhaler 158 is inserted through grommet 160 so that the upper portion of the Inhaler 162 protrudes through and into the interior of the Inhaler Test Chamber 164. The vapor outlet orifice 62 allows vapor 166 to accumulate within the Test Chamber. The essential oils evaporate producing the vapor. Here, essential oils in the vapor phase are tested in the Inhaler Test Chamber. The air inlet hole 58 explicitly shown in FIG. 12, and air inlet hole 60, must be blocked off on the exterior of the Inhaler Test Chamber. These air inlet holes can be blocked with simple Teflon tape that is not shown in FIG. 12 for the purposes of brevity. Alternatively, any other type of covering means may be used to cover the lower portion of the inhaler 168 that extends outside the Inhaler Test Chamber. The fine groves are shown in the hand-held grip 170 of the Inhaler shown in FIG. 12.

As one example, if the No Colds, No Flus™ Inhaler is being tested, then the Inhaler contains 50% *Eucalyptus* Oil (*Eucalyptus globulus*) and 50% Tea Tree Oil (*Melaleuca alternifolia*). In this example, the vapor from this Inhaler is being tested to determine its effectiveness against anthrax. If the anthrax dies in the petri dish under the influence of the vapor from the Inhaler, then it would confirm the effectiveness of the vapor produced from a mixture of 50% *Eucalyptus* Oil and 50% Tea Tree Oil to eradicate anthrax.

The Inhaler Test Chamber 146 in FIG. 12 must be further isolated to contain dangerous test pathogens. Put another way, the Inhaler Test Chamber 146 must be entirely surrounded by another sealed safety chamber to contain the dangerous test pathogens. However, that additional isolation equipment is not shown for the purposes of brevity. Within this isolation equipment, a typical test is conducted as follows. First the test pathogens are grown on a pathogen growing medium in a petri dish which is then inserted through the access door into the Inhaler Test Chamber. Then the access door is closed. Then, the Test Inhaler 158 is inserted through grommet 160. The air inlet holes of the Inhaler are blocked off using Teflon tape or by using other means. The walls of the Inhaler Test Chamber may be made to be transparent. Then, the pathogens may be observed under the influence of the vapor from the essential oil within the Test Inhaler.

Other more complex Test Chambers may be assembled. When vapors from a typical Inhaler are inhaled into the lungs, and if sufficient vapor is inhaled, the vapor from the oil can actually "wet" the interior of the lungs. This "wetting" can be simulated as follows. A Flow Chamber covering the lower portion of the inhaler 168 that extends outside the Inhaler Test Chamber can be made and suitable attached to the wall of the Test Chamber adjacent to the Test Inhaler. That Flow Chamber is not shown in FIG. 12 in the interests of brevity. The pressure within the Flow Chamber (PFC) can be positively pressured with air with respect to the pressure within the Inhaler Test Chamber (PITC). If the air inlet holes of the Test Inhaler are open, then moist vapor is blown into the Inhaler Test Chamber through the vapor outlet orifice 62. The exhaust from the Inhaler Test Chamber may be accumulated from a pipe exiting the Inhaler Test Chamber and re-injected into the air input of the Flow Chamber keeping dangerous pathogens within a closed, continuously, circulating system. Then, the test pathogens in the petri dish may be observed and the effectiveness of the "wet" vapor from the essential oil may be determined.

Similarly the vapor from any one single essential oil from the "List of Essential Oils" can be tested against anthrax. Similarly, the vapor from any mixture of any number of different essential oils in different amounts of those oils in the "List of Essential Oils" can be similarly tested.

In addition, the Test Chamber can be used to determine the effectiveness of all the vapors from all the essential oils mentioned in the previous paragraph against many different pathogens.

For the purposes of this application, the following is the list:

List of Pathogens

Bacteria

*Bacteria Acinetobacter* spp
*Actinobacillus pleuropneumoniae*
*Acinetobacter* sp.
*Actinomyces* sp.
*Aeromonas hydrophila*
*Aeromomas salmonicida*
*Alcaligenes faecalis*
*Bacillus antaecis*
*Bacillus anthracis*
*Bacillus cereus*
*Bacillus diphteria*
*Bacillus dysentery*
*Bacillus mesentericus*
*Bacillus subtilis* spores
*Bacillus subtilus*
*Bacillus tuberculosis*
*Bacterium enteritidis* Gaertner
*Bacterium paratyphi*
*Bacterium rhusopatheae*
*Brucella abortus* bang
*Brucella suis*
*Burkholderia cepacia*
*Chlamydia pneumoniae*
*Chlamydia psittaci*
*Chlamydia trachomatis*
*Clostridium welchii*
*Clostridium sporogenes*
*Clostridium bifermentas*
*Clostridium botulinum*
*Clostridium tertium*
*Clostridium histolyticum*
*Clostridium caloritolerans*
*Coxiella burneti*
*Enterobacter aerogenes*
*Enterobacteriaceae Citrobacter*
*Enterobacteriaceae Hafnia*
*Enterobacteriaceae Klebsiella*
*Enterobacteriaceae Kluvera*
*Enterobacteriaceae Serratia*
*Enterobacter* sp.
*Enterococcus faecium*
*Escherichia coli*
*Francisella tularensis*
*Flavobacterium branchiophilum*
*Flavobacterium haematocrits*
*Haemophilus influenzae*
*Hemophilus influenzae*
*Klebsiella pneumoniae*
*Legionella pneumophila*
*Listeria monocytogenes*
Methicillin-resistant staphylococcal infections (MRSA)
*Micrococcus avium*
*Micrococcus citreus*
*Micrococcus pyogenes*
*Moraxella (Branhamella) catarrhalis*
*Moraxella* spp
*Mycobacterium africanum*
*Mycobacterium avium*
*Mycobacterium avum complex* (MAC)
*Mycobacterium avium-intracellulare*
*Mycobacterium bovis*
*Mycobacterium chelonei*
*Mycobacterium fortuitum*
*Mycobacterium fortuitum* complex
*Mycobacterium intracellulare*
*Mycobacterium lacticola*
*Mycobacterium kansasii*
*Mycobacterium marinum*
*Mycobacterium minetti*
*Mycobacterium pellegrino*
*Mycobacterium phlei*
*Mycobacterium piscium*
*Mycobacterium smegmatis*
*Mycobacterium tuberculosis*
*Mycobacterium ulcerans*
*Mycobacterium vole bacillus*
*Mycobacterium xenopi*
*Mycoplasma pneumoniae*
*Nocardia* sp.
*Pasteurella*
*Pediococcus cerevisiae*
*Proteus mirabilis*
*Proteus vulgaris*

*Proteus* sp.
*Pseudomonas aeruginosa*
*Pseudomonas fluorescens*
*Pseudomonas fragi*
*Pseudomonas putida*
*Pseudomonas putrefaciens*
*Pseudomonas pyocyanea*
*Pseudomonas tolaasii*
*Pyocyaneus*
*Salmonella anatum*
*Salmonella dublin*
*Salmonella durban*
*Salmonella livingstone*
*Salmonella newbrunswick*
*Salmonella newport*
*Salmonella oranienburg*
*Salmonella paratyphi* B
*Salmonella pullorum*
*Salmonella rostock*
*Salmonella senftenberg*
*Salmonella thompson*
*Salmonella typhimurium*
*Sarcina lutea*
*Serratia marcescens*
*Shigella boydii*
*Shigella sonnei*
*Staphylococcus aureus*
*Staphylococcus aureus* haemolyticus
*Staphylococcus bag*
*Staphylococcus epidermidis*
*Staphylococcus paratyphosa* B
*Staphylococcus pyogenes*
*Streptococcus agalactiae*
*Streptococcus faecalis*
*Streptococcus faecium*
*Streptococcus pneumoniae*
*Streptcoccus pyogenes*
*Vibrio alginoliticus*
*Vibrio anguilarum*
*Vibrio cholerae*
*Vibrio harveyi*
*Vibrio parahaemolyticus*
*Vibrio salmonicida*
*Yersinia enterocolitica*
*Yersinia pestis*
*Yersinia pseudo-tuberculosis*
*Yersinia ruckerii*

Viruses

Adenovirus
Adenoviruses
African swine fever virus
Aujeszky Disease virus
Avian reovirus
Canine parvovirus
Celovirus
Classical swine fever virus
Corona virus
Coronaviruses
Coxsackie virus
Coxsackieviruses
Crimean-Congo hemorrhagic fever virus
Cytomegalovirus
Dengue virus
Diphteria virus
Ebola virus
Ektromelie virus
Encephalomyocarditis virus
Enteric cytopathogenic bovine orphan virus (ECBO)
Epstein-Barr virus
European swine fever virus
Foot and Mouth Disease virus
Fowl plague virus (NCD)
Fowl pox virus
Gumboro Disease virus
*Haemophilus influenzae*
Hantavirus
Hepatitis B virus
Hepatitus contagiosa canine virus
Herpes virus
Human Immuno-Deficiency virus (HIV)
Human rotavirus
Infectious bronchitis virus
Infectious bursitis virus
Infectious pancreatic necrosis
Influenza virus
Influenza A virus
Influenza B virus
Influenza C virus
Irido virus (ASFV)
Kyasanur Forest disease virus
Lassa virus
Marburg virus
Myxomatosis virus
New Castle Disease virus
New World Arenaviridae virus
Orthopox commune virus (vaccinia)
Orthomyxoviruses
Omsk hemorrhagic fever virus
Parainfluenza virus
Paramyxo virus
Paramyxovirus type 1
Paramyxovirus type 2
Paramyxovirus type 3
Paramyxovirus type 4
Picorna virus
Picornaviruses
Poliovirus
Porcine parvovirus
Pox virus
Pseudo Bird Pest virus
Rabies virus
Respiratory syncytial virus
Reovirus
Retro virus
Rhino pneumonic virus
Rhinoviruses
Rift Valley fever virus
Smallpox
South African Pest virus
Swine fever virus
Syncytial virus
Systematic ectodermal and mesodermal aculo virus (SMBV)
Teschen virus
Toga virus
Vaccinia virus
Varicella-zoster virus
Vesicular Swine Disease virus
White spot disease virus (SMBV)
Yellow fever virus

Fungi

*Absidia* sp.
*Arachniotus citrinus*
*Aspergillus amstellodami*
*Aspergillus flavus*
*Aspergillus fumigatus*
*Aspergillus glaucus*
*Aspergillus nidulans*
*Aspergillus niger*
*Aspergillus* sp.
*Aspergillus versicolor*
*Blastomyces dermatitidis*
*Candida albicans*
*Candida lypolytica*
*Candida parapsilosis*
*Chaetomium globosum*
*Cladosporium cladosporoides*
*Coccidiodes immitis*
*Cryptococcus* sp.
*Cryptococcus neoformans*
*Entomophthora destruens*
*Entomophthora thaxteriana*
*Entomophthora virulenta*
*Epidermophyton floccosum*
*Exophilia jeanselmei*
*Histoplasma capsulatum*
*Microsporum canis*
*Microsporum gypseum*
*Mucor* sp.
*Myrothecium verrucaria*
*Oöspora lactis*
*Paecillomyces variotii*
*Penicillium funiculosum*
*Penicillium verruccosum*
*Pneumocystis carinii*
*Saprolegnia parasitica*
*Sporothrix schenckii*
*Trichoderma viride*
*Trichophyton equinum*
*Trichophyton mentagrophytes*
*Rhizopus* sp.

Algae

*Anabaena cylindrica*
*Chlorella vulgaris*
*Oscillatoria tenuis*
*Skeletonema* sp.
*Stigeoclonium* sp.
*Tetraselmis* sp.
Yeasts
*Candida albicans*
*Cryptococcus* spp
*Saccharomyces cerevisiae*
*Saccharomyces diastaticus*

Parasites

*Epistylis*
*Gyrodactilus salaris*
*Ichtyobodo necator*
*Ichtyophthiriu*

Various diseases are caused by specific pathogens. In the following, several diseases are related to their pathogenic cause. Then, preferred embodiments of the invention are described to treat, cure or prevent the disease.

Tuberculosis

An important reference on Tuberculosis is made in the book by Mark H. Beers, M.D. and Robert Berkow M.D, Editors, that appears as a the Publication on the World Wide Web (http://www.merck.com/pubs/mmanual/) entitled "The Merck Manual of Diagnosis and Therapy", "Seventeenth Edition", "Centennial Edition", Merck & Co., Whitehouse Station, N.J., 1999 (Beers, et al., 1999), an entire copy of which is incorporated herein by reference. In particular, Section 13 (Infectious Diseases), Chapter 157 (Bacterial Diseases) under the topic of "Caused by Mycobacteria" and "Tuberculosis" of Beers, et al., 1999, is particularly relevant, and entire copy of which is incorporated herein by reference.

Section 13 (Infectious Diseases), Chapter 157 (Bacterial Diseases) and under the general topic of "Caused by Mycobacteria" and "Tuberculosis" of Beers, et al., 1999, it states the following.

Under the specific topic of Etiology, Epidemiology, and Incidence, it states the following:

"TB refers only to disease caused by *Mycobacterium tuberculosis, Mycobacterium bovis* or *Mycobacterium africanum*. Other mycobacteria cause disease similar to TB (see below), but they generally respond poorly to drugs that are effective for TB."

"In developed countries, human TB occurs almost exclusively from inhalation of organisms dispersed as droplet nuclei from a person with pulmonary TB whose sputum smear is positive. *M. Tuberculosis* may float in the air for several hours, thus increasing the chance of spread. Spread can occur in mycobacteriology laboratories and autopsy rooms, in part because the hydrophobic nature of the organism facilitates aerosolization. Fomites appear to play no role in their spread."

"Signs of a potentially very dangerous epidemic of TB have already appeared. The advent of HIV infection has created the circumstances not only for an increased incidence of TB (up 30% in New York State in 1992 to 1993) but also for the development of organisms resistant to all first-line drugs. The incidence of TB increased from 1989 to 1992, but since then more strict control measures appear to have been effective.

However," the threat of drug-resistance organisms remains."

Under the subtitle of "Pulmonary Tuberculosis" related to the above paragraph, it states the following:

"Typically, recrudescent disease occurs in nodular scars in the apex of one or both lungs (*Simon foci*) and may spread through the bronchi to other portions."

Under the topic of "Other Mycobacteria Infections Resembling Tuberculosis" it states the following:

"Mycobacteria other than the tubercle *bacillus* can cause infections in humans. These organisms are commonly found in the environment (soil and water), and exposure is more frequency than development of disease. Since all of the organisms are less virulent than *M. Tuberculosis*, a defect in local or systemic host defense is usually a precondition for disease. *M. avium* complex (MAC)—the closely related species of *M. avium* and *M. intracellulare*—accounts for most of the diseases. Other noteworthy species are *M. kansasii, M. xenopi, M. marinum, M. ulcerans,* and *M. fortuitum* complex (*M. fortuitum* and *M. chelonei*).

Under the subtopic of "Pulmonary Disease" related to the above paragraph, it states:

"Most pulmonary infections involve MAC, but a few are due to *M. kansassi, M. xenopi,* and *M. fortuitim* complex.

The typical patient is a middle-aged white man with prior lung problems such as chronic bronchitis, emphysema, healed TB, bronchiectasis, or silicosis."

Please refer to the article by Eugene Sherry, M.D. and P. H. H. Warnke, Ph.D, entitled "Alternative for MRSA and Tuberculosis (TB): *Eucalyptus* and Tea-Tree Oils as New Topical Antibacterials", Poster Board Number: P376, 2002 Annual Meeting of the American Academy of Orthopaedic Surgeons, Dallas, Tex., February 13–17, 2002, (Sherry and Warnke, 2002), an entire copy of which is incorporated herein by reference.

Sherry and Warnke, 2002, confirm that *Eucalyptus* Oil and Tea Tree Oils are useful to combat TB methicillin-resistant staphylococcal) (MRSA) infections. Applicant has already disclosed the use of *eucalyptus* oil and tea tree oil in relation to tuberculosis in U.S. patent application Ser. No. 09/542,703 that was filed on Apr. 3, 2000. For example, in Ser. No. 09/542,703, please see lines 29–33 on page 1; lines 28–31 on page 3; and lines 14–16 of page 44. application Ser. No. 09/542,703 discusses *staphylococcus aureus* on lines 3–4, page 25; page 28, line 12; and line 10, page 32. The invention disclosed in Ser. No. 09/542,703 discloses *Eucalyptus* Oil and Tea Tree Oils as being effective against a variety of pathogens, including those listed in this paragraph.

Vapors from the 50% *Eucalyptus globulus* and 50% *Melaleuca alternifolia* mixture of essential oils are broadly antipathogenc. Those vapors are effective against many of the pathogens on the above defined list. In particular, they are effective against many of the pathogens that cause tuberculosis which are listed above within this section.

Therefore, the following general statements may be made.

In accordance with the invention, the inhalation of the vapor from 50% *Eucalyptus globulus* and 50% *Melaleuca alternifolia* can be used to prevent tuberculosis.

In accordance with the invention, the inhalation of the vapor from 50% *Eucalyptus globulus* and 50% *Melaleuca alternifolia* can be used to prevent the initial infection of bacteria that cause tuberculosis.

In accordance with the invention, the inhalation of the vapor from 50% *Eucalyptus globulus* and 50% *Melaleuca alternifolia* can be used to cure tuberculosis.

In accordance with the invention, the inhalation of the vapor from 50% *Eucalyptus globulus* and 50% *Melaleuca alternifolia* can be used to cure the infections of bacteria that cause tuberculosis.

In accordance with the invention, the inhalation of the vapor from 50% *Eucalyptus globulus* and 50% *Melaleuca alternifolia* can be used to treat tuberculosis.

In accordance with the invention, the inhalation of the vapor from 50% *Eucalyptus globulus* and 50% *Melaleuca alternifolia* can be used to treat the infections of bacteria that cause tuberculosis.

In accordance with the invention, the inhalation of the vapor from any mixture of *Eucalyptus globulus* and *Melaleuca alternifolia* can be used to prevent tuberculosis.

In accordance with the invention, the inhalation of the vapor any mixture of *Eucalyptus globulus* and *Melaleuca alternifolia* can be used to prevent the initial infection of bacteria that causes tuberculosis.

In accordance with the invention, the inhalation of the vapor from any mixture of *Eucalyptus globulus* and *Melaleuca alternifolia* can be used to cure tuberculosis.

In accordance with the invention, the inhalation of the vapor from any mixture of *Eucalyptus globulus* and *Melaleuca alternifolia* can be used to cure the infection of bacteria that cause tuberculosis.

In accordance with the invention, the inhalation of the vapor from any mixture of *Eucalyptus globulus* and *Melaleuca alternifolia* can be used to treat tuberculosis.

In accordance with the invention, the inhalation of the vapor from any mixture of *Eucalyptus globulus* and *Melaleuca alternifolia* can be used to treat the infection of bacteria that cause tuberculosis.

The No Sinus Pain™ Personal Lung Inhaler containing 50% *Eucalyptus globulus* and 50% *Melaleuca alternifolia* that is manufactured by Inhalation, Inc. is a preferred embodiment of the invention used to prevent, treat or cure tuberculosis. The Super Sinus and Lungs™ Personal Lung Inhaler containing 33⅓% *Eucalyptus globulus*, 33⅓% *Eucalyptus citriodora*, and 33⅓% *Melaleuca alternifolia* that is manufactured by Inhalation, Inc. is also another preferred embodiment of the invention used to prevent, treat or cure tuberculosis.

In accordance with the invention, the antipathogenic properties of vapors from any essential oil listed on the above defined "List of Essential Oils" can be tested in the above defined Test Chamber. Those vapors showing antipathogenic properties against the pathogens causing tuberculosis can be identified using the above Test Chamber. That essential oil may then be provided in one or more of the Inhalers described herein. Inhaled vapors from such Inhaler apparatus may be used to prevent or cure tuberculosis.

In accordance with the invention, the antipathogenic properties of vapors from any mixture of essential oil listed on the above defined List of Essential Oils can be tested in the above defined Test Chamber. Those vapors showing antipathogenic properties against the pathogens causing tuberculosis can be identified using the above defined Test Chamber. That essential oil may then be provided in the above defined Inhalers. Inhaled vapors from the Inhaler apparatus may be used to prevent or cure tuberculosis.

Specific mixtures of essential oils of interest to be tested in the above defined Test Chamber apparatus are listed as follows:

Mixture #1

One or more of the following mixed together:

A. *Eucalyptus globulus;*

B. *Melaleuca alternifolia;*

C. different varieties of Clove oil including *Eugenia caryophyllata* and *Syzygium aromaticum;*

D. different varieties of Cinnamon including *Cinnamonum camphora* and *Cinnamonum zeylanicum;*

E. different varieties of Oregano including *Origanum vulgare;*

F. different varieties of Savory including *Satureia Montana;* and

G. different varieties of Thyme including *Thymus satureioides, Thymus serpyllium, Thymus vulgaris,* and *Thymus zygis.*

For Example: Mixture #1A

A. 50% *Eucalyptus globuls;*

B. 25% *Melaleuca alternifolia;*

C. 5% by volume of *Uegenia caryophyllata;*

D. 5% by volume of *Cinnamonun camphora;*

E. 5% by volume of *Oreganum vulagare;*
F. 5% by volume of *Satureia montana;* and
G. 5% by volume of *Thymus vulgaris.*

Mixture #2

One or more of the following mixed together:
A. *Eucalyptus globulus* (at least 30% by volume);
B. *Melaleuca alternifolia* (at least 30% by volume)

With at least one of the following oils added:
C. different varieties of Clove oil including *Eugenia caryophyllata* and *Syzygium aromaticum;*
D. different varieties of Cinnamon including *Cinnamonum camphora* and *Cinnamonum zeylanicum;*
E. different varieties of Oregano including *Origanum vulgare;*
F. different varieties of Savory including *Satureia montana;* and
G. different varieties of Thyme including *Thymus satureioides, Thymus serpyllium, Thymus vulgaris,* and *Thymus zygis.*

For Example: Mixture #2A

A. *Eucalyptus globulus* (at least 30% by volume);
B. *Melaleuca alternifolia* (at least 30% by volume)
C. *Origanum vulgare* (less than 40%)

Mixture #3

One or more of the following mixed together:
A. different varieties of *Eucalyptus* oil *Eucalyptus citriadora, Eucalyptus globulus, Eucalyptus radiata,* and *Eucalyptus smithii*
B. *Melaleuca alternifolia;*
C. different varieties of Clove oil including *Eugenia caryophyllata* and *Syzygium aromaticum;*
D. different varieties of Cinnamon including *Cinnamonum camphora* and *Cinnamonum zeylanicum;*
E. different varieties of Oregano including *Origanum vulgare;*
F. different varieties of Savory including *Satureia montana;*
G. different varieties of Thyme including *Thymus satureioides, Thymus serpyllium, Thymus vulgaris,* and *Thymus zygis;*

For Example: Mixture #3A

A. 25% by volume of *Eucalyptus globulus;*
B. 25% by volume of *Eucalyptus citriodora;*
C. 25% by volume of *Melaleuca alternifolia;*
D. 5% by volume of *Uegenia caryophyllata;*
E. 5% by volume of *Cinnamonun camphora;*
F. 5% by volume of *Oreganum vulagare;*
G. 5% by volume of *Satureia Montana;* and
H. 5% by volume of *Thymus vulgaris.*

Mixture #4

One or more of the following mixed together:
A. different varieties of *Eucalyptus* oil *Eucalyptus citriadora, Eucalyptus globulus, Eucalyptus radiata,* and *Eucalyptus smithii* (at least 30% by volume)
B. *Melaleuca alternifolia* (at least 30% by volume);

With at least one of the following oils added:
C. different varieties of Clove oil including *Eugenia caryophyllata* and *Syzygium aromaticum;*
D. different varieties of Cinnamon including *Cinnamonum camphora* and *Cinnamonum zeylanicum;*
E. different varieties of Oregano including *Origanum vulgare;*
F. different varieties of Savory including *Satureia Montana;*
G. different varieties of Thyme including *Thymus satureioides, Thymus serpyllium, Thymus vulgaris,* and *Thymus zygis;*

For Example: Mixture #4A

A. *Eucalyptus globulus* (at least 20% by volume)
B. *Eucalyptus citriodora* (at least 20% by volume)
C. *Melaleuca alternifolia* (at least 40% by volume)
D. *Origanum vulgare* (less than 20% by volume)

Mixture #5

One or more of the following mixed together:
A. different varieties of *Eucalyptus* oil *Eucalyptus citriadora, Eucalyptus globulus, Eucalyptus radiata,* and *Eucalyptus smithii*
B. *Melaleuca alternifolia;*
C. different varieties of Clove oil including *Eugenia caryophyllata* and *Syzygium aromaticum;*
D. different varieties of Cinnamon including *Cinnamonum camphora* and *Cinnamonum zeylanicum;*
E. different varieties of Oregano including *Origanum vulgare;*
F. different varieties of Savory including *Satureia montana;*
G. different varieties of Thyme including *Thymus satureioides, Thymus serpyllium, Thymus vulgaris,* and *Thymus zygis;*
H. different varieties of Cajeput including *Melaleuca cajeputi;*
I. different varieties of Geranium including *Pelargonium roseum* and *Pelargonium graveolens.*
J. different varieties of Lavender including *Lavandula hybrida, Lavandula latifolia, Lavandula officinalis* var., and *Lavandula officinalis* var. vera;
K. different varieties of Myrtle including *Myrtus communis;*
L. different varieties of Niaouli including *Melaleucea quinquinervera*
M. different varieties of Petitgrain including *Citrus aurantifolia, Citrus aur. bigarade* and *Citrus arantium amara.*
N. different varieties of Pine oil including *Pinus nigra, Pinus nigra,* pinaster and sylvestris, *Pinus sylvestris,* and Sea Pine; and
O. different varieties of Tarragon including *Artemisia dracunculus;*

For Example: Mixture #5A

A. 25% by volume of *Eucalyptus globulus;*
B. 10% by volume of *Eucalyptus citriodora;*
C. 10% by volume of *Eucalyptus radiata;*
D. 25% by volume of *Melaleuca alternifolia;*
E. 2% by volume of *Uegenia caryophyllata;*
F. 2% by volume of *Cinnamonun camphora;*
G. 2% by volume of *Oreganum vulagare;*
H. 2% by volume of *Satureia Montana;*

I. 2% by volume of *Thymus vulgaris;*
J. 10% *Melaleuca cajeputi;* and
K. 10% *Lavendula officinalis.*

Mixture #6

One or more of the following mixed together:
A. different varities of *Eucalyptus* oil including *Eucalyptus citriadora, Eucalyptus globulus, Eucalyptus radiata,* and *Eucalyptus smithii*
B. *Melaleuca alternifolia;*
C. different varieties of Clove oil including *Eugenia caryophyllata* and *Syzygium aromaticum;*
D. different varieties of Cinnamon including *Cinnamonum camphora* and *Cinnamonum zeylanicum;*
E. different varieties of Oregano including *Origanum vulgare;*
F. different varieties of Savory including *Satureia montana;*
G. different varieties of Thyme including *Thymus satureioides, Thymus serpyllium, Thymus vulgaris,* and *Thymus zygis;*
H. different varieties of Cajeput including *Melaleuca cajeputi;*
I. different varieties of Geranium including *Pelargonium roseum* and *Pelargonium graveolens.*
J. different varieties of Lavender including *Lavandula hybrida, Lavandula latifolia, Lavandula officinalis* var., and *Lavandula officinalis* var. vera;
K. different varieties of Myrtle including *Myrtus communis;*
L. different varieties of Niaouli including *Melaleucea quinquinervera*
M. different varieties of Petitgrain including *Citrus aurantifolia, Citrus aur. bigarade* and *Citrus arantium amara.*
N. different varieties of Pine oil including *Pinus nigra, Pinus nigra, pinaster* and *sylvestris, Pinus sylvestris,* and Sea Pine;
O. different varieties of Tarragon including *Artemisia dracunculus;*
P. different varieties of Lemongrass including *Cymbopogon citratus* and *Cymbopogon flexuosus*
Q. different varities of peppermint including *Mentha piperita*
R. different varieites of Rosemary including *Rosmarinus officinalis*

For Example: Mixture #6A

A. 25% by volume of *Cymbopogon citratus*
B. 25% by volume of *Melaleuca alternifolia;*
C. 15% by volume of *Cinnamonum zeylanicum*
D. 2½% by volume of *Oreganum vulagare;*
E. 2½% by volume of *Thymus vulgaris;*
F. 10% *Melaleuca cajeputi;* and
G. 10% *Lavendula officinalis.*
H. 10% *Mentha piperita*

In some of the above mixtures, the term "*eucalyptus* oil" may be chosen to be *Eucalyptus globulus,* and "tea tree oil" is *Melaleuca alternifolia.*

The vapors from Mixture #1, Mixture #2, Mixture #3, Mixture #4, Mixture #5, and Mixture #6 which are defined above, and their respective examples, may be used to prevent, treat, and cure tuberculosis. The effective amounts of vapors are determined by various methods including those described in relation to the Test Chamber.

In accordance with the above, the vapors from 100% *Melaleuca alternifolia* may be used in a preferred embodiment of the invention to prevent, treat, and cure tuberculosis.

In accordance with the above, another preferred embodiment of the invention is a method to reduce the risks of infection of the human respiratory system by *Mycobacterium tuberculosis* in an enclosed public area having one or more human beings within the enclosed area comprising the following steps:

(a) within a period of time of 30 minutes before entering the public area, inhaling the concentrated vapors from a mixture of 50% of *eucalyptus* oil and 50% tea tree oil, whereby the concentrated vapors are generated within a hand-held atomizer apparatus; and (b) after entering the public area, periodically inhaling the concentrated vapors from the mixture in the hand-held atomizer apparatus, whereby the period of time between successive inhalations exceeds 30 minutes, and whereby the period of time between successive inhalations is less than 2 hours;

and whereby infections from *Mycobacterium tuberculosis* are known to cause serious infections of the human respiratory system.

Opportunistic Infections by Pathogens in Lungs of Patients Having with Cystic Fibrosis Please refer to book by Balch, J. F., and Balch, P. A., that is entitled "Prescription for Nutritional Healing", Third Edition, Avery Publishing Group, Garden City Park, New York, N.Y., 2000 ("Balch and Balch, 2000"), an entire copy of which is incorporated herein by reference.

Page 311 of Balch and Balch, 2000, states in part under the topic of "Cystic Fibrosis":

"Cystic fibrosis (CF) is the most common inherited illness among Americans of northern and western European ancestry. It occurs in people of all ethnic backgrounds and is most common in Caucasians. It occurs with approximately equal frequency in men and women."

"One in every 3,000 children in the United States is born with the disorder. It is estimated that 8 million Americans are silent carriers of the defective gene that leads to this disease. The gene responsible for CF was identified in 1989 on human chromosome 7, and it encodes instructions for a protein that regulates the passage of salt in and out of the cells of the body's endocrine glands. This defective gene transforms the protein (called the cystic fibrosis transmembrane conductance regulator [CFTR]) and causes it to produce a mucus too thick and too abundant for the body to excrete."

"The airway, gastrointestinal tract, bile ducts of the liver, ducts of the pancreas, and the male genitourinary tract all produce mucus. Cystic fibrosis alters this normally protective mucus and transforms it into a thick, abnormal excretion that obstructs airways and damages tissue. Symptoms of CF begin early in life. Glands in the lungs and bronchial tubes secrete large quantities of thick, sticky mucus that blocks lung passages and provides the perfect place for harmful bacterial to thrive. *Pseudomonas aeruginosa* (also common in cancer and burn patents) is the bacteria that most commonly colonizes the lungs, resulting in chronic coughing and wheezing, difficulty breathing, and recurrent lung infections. Once established, the bacteria remain in the lungs and are responsible for repeated outbreaks of infection. They form their own dense structure, called a biofilm, and are immune to most current treatments. They also produce toxic proteins that can cause tissue damage and weaken the immune system. The lungs of many children with CF are inhabited or colonized by the *Pseudomonas aeruginosa* bacteria before they are ten years of age."

An important reference in this field appears under the topic of "General" under Section 19 (Pediatrics), Chapter 267 (Cystic Fibrosis) Beers, et al., 1999, an entire copy of which is incorporated herein by reference.

Section 19 (Pediatrics), Chapter 267 (Cystic Fibrosis) in Beers, et al., 1999, states in part:

"Evidence suggests that the lungs are histologically normal at birth. Pulmonary damage is probably initiated by diffuse obstruction in the small airways by abnormally thick mucus secretions. Bronchiolitis and mucopurulent plugging of he airways occur secondary to obstruction and infection. Bronchial changes are more common than parenchymal changes. Emphysema is not prominent. As the pulmonary process progresses, bronchial walls thicken; the airways fill with purulent, viscid secretions; areas of atelectasis develop; and hilar lymph nodes enlarge. Chronic hypoxemia results in muscular hypertrophy of the pulmonary arteries, pulmonary hypertension, and right ventricular hypertrophy. Much of the pulmonary damage may be caused by immune-mediated inflammation secondary to the release of proteases by neutrophils in the airways. Bronchoalveolar lavage fluid, even early in life, contains large number os neutrophils and increased concentrations of free neutrophil elastase, DNA, and interleukin-8."

"Early in the course, *Staphylococcus aureus* is the pathogen most often isolated from the respiratory tract, but as the disease progresses, *Pseudomonas aeruginosa* is most frequently isolated. A mucoid variant of *Pseudomonas* is uniquely associated with CF. Colonization with *Burkholderia capacia* occurs in up to 7% of adult patients and may be associated with rapid pulmonary deterioration."

Vapors from the 50% *Eucalyptus globulus* and 50% *Melaleuca alternifolia* mixture of essential oils are broadly antipathogenc. Those vapors are effective against many of the pathogens on the above defined list. In particular, they are effective against many of the pathogens that invade the lungs of patients with cystic fibrosis that are listed above within this section.

Therefore, the following general statements may be made.

In accordance with the invention, the inhalation of the vapor from 50% *Eucalyptus globulus* and 50% *Melaleuca alternifolia* can be used to prevent infection of the lungs of patients having cystic fibrosis by pathogens that include *Pseudomonas aeruginosa*.

In accordance with the invention, the inhalation of the vapor from 50% *Eucalyptus globulus* and 50% *Melaleuca alternifolia* can be used to prevent the initial infection by bacteria that infect the lungs of patients having cystic fibrosis.

In accordance with the invention, the inhalation of the vapor from 50% *Eucalyptus globulus* and 50% *Melaleuca alternifolia* can be used to cure infections of *Pseudomonas aeruginosa* in the lungs of patients having cystic fibrosis.

In accordance with the invention, the inhalation of the vapor from 50% *Eucalyptus globulus* and 50% *Melaleuca alternifolia* can be used to cure infections of bacteria that infect the lungs of patients having cystic fibrosis.

In accordance with the invention, the inhalation of the vapor from 50% *Eucalyptus globulus* and 50% *Melaleuca alternifolia* can be used to treat infections of the lungs of patients having cystic fibrosis by pathogens that include *Pseudomonas aeruginosa*.

In accordance with the invention, the inhalation of the vapor from 50% *Eucalyptus globulus* and 50% *Melaleuca alternifolia* can be used to treat the infections of bacteria that infect the lungs of patients having cystic fibrosis.

In accordance with the invention, the inhalation of the vapor from any mixture of *Eucalyptus globulus* and *Melaleuca alternifolia* can be used to prevent infection of the lungs of patients having cystic fibrosis by pathogens that include *Pseudomonas aeruginosa*.

In accordance with the invention, the inhalation of the vapor any mixture of *Eucalyptus globulus* and *Melaleuca alternifolia* can be used to prevent the infection by bacteria that infect the lungs of patients having cystic fibrosis.

In accordance with the invention, the inhalation of the vapor from any mixture of *Eucalyptus globulus* and *Melaleuca alternifolia* can be used to cure infections of *Pseudomonas aeruginosa* in the lungs of patients having cystic fibrosis.

In accordance with the invention, the inhalation of the vapor from any mixture of *Eucalyptus globulus* and *Melaleuca alternifolia* can be used to cure infections of bacteria that infect the lungs of patients having cystic fibrosis.

In accordance with the invention, the inhalation of the vapor from any mixture of *Eucalyptus globulus* and *Melaleuca alternifolia* can be used to treat infections of the lungs of patients having cystic fibrosis by pathogens that include *Pseudomonas aeruginosa*.

In accordance with the invention, the inhalation of the vapor from any mixture of *Eucalyptus globulus* and *Melaleuca alternifolia* can be used to treat infections of bacteria that infect the lungs of patients having cystic fibrosis.

Similar statements to the above 12 statements are hereby made by reference with regards to the specific pathogen *Staphylococcus aureus* and to the specific pathogen *Burkholderia cepacia*.

The No Sinus Pain™ Personal Lung Inhaler manufactured by Inhalation, Inc. is a preferred embodiment of the invention used to prevent, treat, or cure opportunistic infections of the human respiratory system of those individuals having cystic fibrosis. The Super Sinus and Lungs™ Personal Lung Inhaler manufactured by Inhalation, Inc. is also another preferred embodiment of the invention used to prevent, treat or cure opportunistic infections of the human respiratory system of those individuals having cystic fibrosis.

A pertinent reference is Price and Price, 1999, op. cit. In particular, page 70 of Price and Price, 1999, has Table 4.4 that shows that "*Melaleuca alternifolia* [TEA TREE]" is particularly effective against the pathogen *Pseudomonas aeruginosa*. An entire copy of Table 4.4 is also incorporated herein by reference.

In accordance with the invention, the antipathogenic properties of vapors from any essential oil listed on the above defined "List of Essential Oils" can be tested in the above defined Test Chamber. Those vapors showing antipathogenic properties against the pathogens causing infections within the lungs of patients having cystic fibrosis can be identified using the Test Chamber and related experimental procedures. That essential oil may then be provided in one or more of the Inhalers as described herein. Inhaled vapors from such Inhaler apparatus may be used to prevent, treat, or cure infections of the lungs by bacteria that include

*Staphylococcus aureus, Pseudomonas aeruginosa*, including a mucoid variant of that bacteria, and *Burkholderia capacia*.

In accordance with the invention, the antipathogenic properties of vapors from any mixture of essential oil listed on the above defined "List of Essential Oils" can be tested in the Test Chamber. Those vapors showing antipathogenic properties against the pathogens infecting the lungs of patients having cystic fibrosis can be identified using that the Test Chamber and related experimental procedures. The essential oil having such antipathogenic properties may then be provided in the Inhalers described herein. Inhaled vapors from that Inhaler apparatus may be used to prevent, treat, or cure infections of the lungs by bacteria that include *Staphylococcus aureus, Pseudomonas aeruginosa*, including a mucoid variant of that bacteria, and *Burkholderia capacia*.

The vapors from Mixture #1, Mixture #2, Mixture #3, Mixture #4, Mixture #5, and Mixture #6 which are defined above, and their respective examples, may be used to prevent, treat, and cure opportunistic infections associated with cystic fibrosis. The effective amounts of vapors are determined by various methods including those described in relation to the Test Chamber.

In accordance with the above, any combination of *Eucalyptus* oil and Tea Tree oil may be used for various preferred embodiments of the invention. In accordance with the above, the vapors from pure 100% *Melalecua alternifolia* may be used in the invention to prevent, treat, and cure opportunistic infections associated with cystic fibrosis.

Accordingly, it is evident that a preferred embodiment of the invention is a method to reduce the risks of infection of the human respiratory system by *Staphylococcus aureus* in an enclosed public area having one or more human beings within the enclosed area comprising the following steps:

(a) within a period of time of 30 minutes before entering the public area, inhaling from a hand-held atomizer apparatus the concentrated vapors from a mixture of a first percentage of *eucalyptus* oil with the remaining component comprised of tea tree oil; and (b) after entering the public area, periodically inhaling from the hand-held atomizer apparatus the concentrated vapors from the mixture, whereby the period of time between successive inhalations exceeds 30 minutes, and whereby the period of time between successive inhalations is less than 2 hours; and whereby the first percentage of *eucalyptus* oil is selected from a list comprising 1% *eucalyptus* oil, 5% *eucalyptus* oil, 10% *eucalyptus* oil, 20% *eucalyptus* oil, 30% *eucalyptus* oil, 40% *eucalyptus* oil, 50% *eucalyptus* oil, 60% *eucalyptus* oil, 70% *eucalyptus* oil, 80% *eucalyptus* oil, 90% *eucalyptus* oil, 95% *eucalyptus* oil, and 99% *eucalyptus* oil; and whereby the concentrated vapors are generated within the hand-held atomizer apparatus; and whereby the concentrated vapors are inhaled through at least one orifice attached to the hand-held atomizer apparatus.

In accordance with the above, another preferred embodiment of the invention is a method to reduce the risks of infection of the human respiratory system by *Pseudomonas aeruginosa* in an enclosed public area having one or more human beings within the enclosed area comprising the following steps:

(a) within a period of time of 30 minutes before entering the public area, inhaling the concentrated vapors from a mixture of 50% of *eucalyptus* oil and 50% tea tree oil, whereby the concentrated vapors are generated within a hand-held atomizer apparatus, and whereby the concentrated vapors are inhaled through at least one orifice attached to the hand-held atomizer apparatus; and (b) after entering the public area, periodically inhaling the concentrated vapors from the mixture in the hand-held atomizer apparatus, whereby the period of time between successive inhalations exceeds 30 minutes, and whereby the period of time between successive inhalations is less than 2 hours;

and whereby infections from *Pseudomonas aeruginosa* are known to cause fatal lung infections of individuals having cystic fibrosis.

In accordance with the above, yet another preferred embodiment of the invention is a method to reduce the risks of infection of the human respiratory system by *Burkholderia capacia* in an enclosed public area having one or more human beings within the enclosed area comprising the following steps:

(a) within a period of time of 30 minutes before entering the public area, inhaling the concentrated vapors from a mixture of 50% of *eucalyptus* oil and 50% tea tree oil, whereby the concentrated vapors are generated within a hand-held atomizer apparatus, and whereby the concentrated vapors are inhaled through at least one orifice attached to the hand-held atomizer apparatus; and (b) after entering the public area, periodically inhaling the concentrated vapors from the mixture in the hand-held atomizer apparatus, whereby the period of time between successive inhalations exceeds 30 minutes, and whereby the period of time between successive inhalations is less than 2 hours;

and whereby infections from *Burkholderia capacia* are known to cause fatal lung infections of individuals having cystic fibrosis.

Inhaled Anthrax, Smallpox, Botulism, Plague, Tularemia, Hemorrhagic Fever Viruses, Tuberculosis and other Inhaled Bioterrorism Pathogens Various different pathogens are particularly susceptible to use by bioterrorists. These pathogens include bacteria, protozoa, viruses, prions, and fungi. Particular pathogens of great concern include anthrax, smallpox, botulism, plague tularemia, hemorrhagic fever viruses, and tuberculosis. Please refer to the article entitled "Bioterrorism a real threat; are we ready" in The Seattle Times, Oct. 7, 2001, the front page, page A26, and page A27, an entire copy of which is incorporated herein by reference. In particular, please see the table entitled "An invisible arsenal" under the category of "Biological terrorism" on page A26. That table shows that inhaled forms of the pathogens anthrax, smallpox, botulism, plague and tularemia are very likely to be used by bioterrorists because of their ease of dispersal.

For additional background information for such bioterrorism pathogens, please also refer the following: (a) the article entitled "Deadly fever hits border of Pakistan, Afghanistan", The Seattle Times, Oct. 5, 2001, page A6; (b) the article entitled "Fla. man gravely ill with rare anthrax", The Seattle Times, Oct. 5, 2001, page A9; (c) the article entitled "Florida man contracts rare form of anthrax", The Herald, Oct. 5, 2001, page A4; (d) the article entitled "Anthrax death first in 25 years", The Herald, Oct. 6, 2001, page A3; and (e) the article entitled "FBI Tries to crack anthrax mystery", The Seattle Times, Oct. 9, 2001, front page and page A4. Entire copies of the articles cited in (a), (b), (c), (d) and (e) are incorporate herein by reference.

Entire copies of all references cited in the articles in (a), (b), (c), (d), and (e) are also incorporated herein by reference.

The above articles describe the following typical situation. A pathogen, for example anthrax, is inhaled into the human respiratory system. If suitable antibiotics are used, then sometimes the massive infection due to anthrax is prevented. If a massive infection is prevented, then death is prevented. So, the "spores" from anthrax can be inhaled, but suitably administered antibiotics can prevent the onset of the disease called "anthrax". Ser. No. 09/542,703 teaches that the repetitive inhalation of vapors from essential oils including *Eucalyptus* Oil (such as *Eucalyptus globulus*, *Eucalyptus smithii*, etc.), and Tea Tree Oil (such as *Melaleuca alternifolia*) can prevent the initial infection of inhaled pathogens. While the pathogens are inhaled, the essential oils having antipathogenic qualities prevent the outbreak of an uncontrolled infection. The prevention of the uncontrolled infection "prevents the disease". Put anther way, the repetitive inhalation of vapors from essential oils having antipathogenic qualities prevents the death of the patient due to the "disease".

Put yet another way, the repetitive inhalation of essential oils having antipathogenic qualities can be used to prevent the disease of "inhalation anthrax". Similarly, the repetitive inhalation of essential oils having antipathogenic qualities can be used to prevent the additional diseases of inhalation smallpox, inhalation botulism, inhalation plague inhalation tularemia, inhalation hemorrhagic fever viruses, and of course, inhalation tuberculosis.

Various additional references are also incorporated herein that are related to preferred embodiments of the invention. Please refer to Time Magazine having the cover entitled "How Real is the Threat?", "Germ and chemical warfare . . . " dated Oct. 8, 2001, an entire copy of which is incorporated herein by reference. Entire copies of all the references cited in this Time Magazine article are also incorporated herein by reference.

Please refer to the book entitled "Killer Germs, Rogue Diseases of the Twenty-First Century" by Pete Moore B.Sc., PhD, Carlton Books Limited, London, Great Britain, 2001, an entire copy of which is incorporated herein by reference. Entire copies of all the references cited in this book are also incorporated herein by reference.

Please also refer to the book entitled "Germs: Biological Weapons and America's Secret War", by Judith Miller, Stephen Engelberg, and William J. Broad, Simon & Schuster, 2001, an entire copy of which is incorporated herein by reference. Entire copies of all the references cited in this book are also incorporated herein by reference.

Please also refer to the book entitled "Living Terror: What America Needs to Know to Survive the Coming Bioterrorist Catastrophe", by Michael T. Osterholm, and John Schwartz, Dell Publishing Company, 2001, an entire copy of which is incorporated herein by reference. Entire copies of all the references cited in this book are also incorporated herein by reference.

Please also refer to the book entitled "Biohazard: The Chilling True Story of the Largest Covert Biological Weapons Program in the World" by Ken W. Alibek and Stephen Handelman, Dell Publishing Company, 2000, an entire copy of which is incorporated herein by reference. Entire copies of all the references cited in this book are also incorporated herein by reference.

Please also refer to the book entitled "America's Achilles' Heel: Nuclear, Biological, and Chemical Terrorism and Covert Attack", by Richard A. Falkenrath, Robert D. Newman, and Bradley A. Thayer, MIT Press, 1998, an entire copy of which is incorporated herein by reference. Entire copies of all the references cited in this book are also incorporated herein by reference.

Please also refer to the book entitled "Toxic Terror: Assessing Terrorist Use of Chemical and Biological Weapons", by Jonathan B. Tucker (Editor), MIT Press, 2000, an entire copy of which is incorporated herein by reference. Entire copies of all references cited in this book are also incorporated herein by reference.

Please also refer to the book entitled "Chemical and Biological Terrorism: Research and Development to Improve Civilian Medical Response", Staff of the Institute of Medicine, National Academy Press, 1999, an entire copy of which is incorporated herein by reference. Entire copies of all references cited in this book are also incorporated herein by reference.

Please also refer to the book entitled "The Biology of Doom: The History of America's Secret Germ Warfare Project", Ed Regis, Henry Holt & Company, 1999, an entire copy of which incorporated herein by reference. Entire copies of all references cited in this book are also incorporated herein by reference.

Please also refer to the book entitled "Death in the Air: Globalism, Terrorism and Toxic Warfare", by Leonard G. Horowitz and Jacqueline G. Lindenbach, Tetrahedron Publishing Group, 2001, an entire copy of which is incorporated herein by reference. Entire copies of all references cited in this book are also incorporated herein by reference.

Please also refer to the book entitled "Lethal Mists: An Introduction to the Natural and Military Sciences of Chemical, Biological Warfare and Terrorism", by Eric R. Taylor, Nova Science, 1999, an entire copy of which is incorporated herein by reference. Entire copies of all references cited in this book are also incorporated herein by reference.

Please also refer to the book entitled "Handbook of Chemical and Biological Warfare Agents", by D. Hank Ellison, CRC Press, 1999, an entire copy of which is incorporated herein by reference. Entire copies of all references cited in this book are also incorporated herein by reference.

Please also refer to the book entitled "Plague Wars: The Terrifying Reality of Biological Warfare", by Tom Mangold and Jeff Boldberg, Martin's Press, 2001, an entire copy of which is incorporated herein by reference. Entire copies of all the references cited in this book are also incorporated herein by reference.

Also included herein by reference are entire copies of all references now cited in the U.S. Library of Congress on the subjects of bioterrorism, infectious agents, bacteria, viruses, fungi, prions, pathogens, infectious pathogens, or under any other topic, or phrase, explicitly mentioned in the specification herein or that is explicitly mentioned in any of the references cited herein.

There are many different essential oils with antipathogenic qualities. Some of these oils are listed in the Jun. 15, 2001 letter to Dr. Richard C. Honour, an entire copy of which is incorporated herein by reference. In that Jun. 15, 2001 letter are listed the samples of oils that the inventors gave to Dr. Honour for testing which the inventors had theorized to have had antipathogenic qualities. Dr. Honour confirmed that many of those oils which he tested had valid antipathogenic qualities. For further reference to these documents, please refer to Provisional Patent Application No. 60/328,912 having the Filing Date of Oct. 12, 2001.

Some of the essential oils having the strongest antipathogenic effects include oregano, savory, cinnamon, thyme, clove, and Tea Tree Oil. As a reference for these oils, please refer to the book entitled "Advanced Aromatherapy, The Science of Essential Oil Therapy", by Kurt Schnaubelt, Ph.D., Healing Arts Press, Rochester, Vt., 1998, Translated from the German by J. Michael Beasley, an entire copy of which is incorporated herein (hereinafter, "Schnaubelt, 1998"). In particular, please refer to page 36 in Schnaubelt, 1998.

Other essential oils having somewhat lesser antipathogenic properties include pine oil, cajeput, *Eucalyptus globulus,* lavender, myrtle, geranium, petitgrain, tarragon, niaouli, and *Thymus serpyllium.* Please refer to Schnaubelt, 1998, page 36.

The inventors have heretofore used many different mixtures of *Eucalyptus globulus* and *Melaleuca alternifolia* to prevent the infection of various pathogens. This mixture is also effective against certain bioterrorism pathogens.

The inventors have also used combinations of oregano oil with *Eucalyptus citriodora* to mask the strong smell of oregano oil and for its own specific antipathogenic properties. Oregano oil produces very strong vapors which are unpleasant to the inventors. Fortunately, the strong smell of oregano vapors may be masked by the pleasant smell from *Eucalyptus citriodora* vapors. In this way, the strong antipathogenic vapors from oregano oil may be inhaled to prevent infection from various pathogens.

To date, the inventors have also tested many other mixtures of essential oils to prevent the infection of various pathogens. As explained above, the test pathogens may be tested in the Test Chamber shown in FIG. 12. However, following such successful tests, animal tests may be required.

The antipathogenic qualities of test essential oils may be tested with animals. The following procedure provides one example for animal testing. For example, put a sheep in a room that has strong evaporated vapors from *Eucalyptus globulus* and *Melaleuca alternifolia.* Let the sheep stay in the room for several hours. Then take the sheep to an anthrax test chamber. Put the sheep in the anthrax test chamber. Introduce into the anthrax test chamber inhalation anthrax. Then, using prudent techniques approved by the Centers for Disease Control and Prevention ("CDC"), carefully exhaust the chamber, and remove the sheep. Then return the sheep to the room that has strong evaporated vapors *Eucalyptus globulus* and *Melaleuca alternifolia.* If the sheep does NOT contract the disease of inhalation anthrax, then in this case vapors from *Eucalyptus globulus* and *Melaleuca alternifolia* would be an effective preventative agent against inhalation anthrax. The vapors from other essential oils may be similarly tested against various other pathogens using analogous techniques.

A primary example of a bioterrorism agent is the pathogen causing anthrax. The bacterium, *Bacillus anthracis,* causes anthrax. The mechanism for generating disease from an infection of *Bacillus anthracis* was recently succinctly described in a Press Release dated Aug. 29, 2002 from the National Institute of Environmental Health Sciences, National Institutes of Health, an entire copy of which is incorporated herein by reference. Contact individuals are Sue Pondrom (619-543-6163) and Tom Harkins (919-541-1402). The first 4 paragraphs from this Press Release are repeated herein as follows:

"Why is anthrax so devastating? A mechanism by which inhaled anthrax disarms and evades the immune system has been described by NIEHS Superfund-supported researchers at the University of California, San Diego School of Medicine.

This lab-culture research with mouse cells shows how a complex of anthrax proteins called lethal toxin inhibits and destroys macrophages, the large white blood cells that act as the body's first defense against pathogens. The legal toxin also disables the signaling mechanism triggering immune activation. This allows the bacteria to spread through the body unchecked by the immune system, resulting in rapid and potentially lethal anthrax infection.

The research was published online August 29 in Science Express, the website of the journal Science.

When the bacterium (*B. anthracis*) is inhaled, its spores are surrounded by alveolar macrophages in the lung, the beginning stage of normal immune response. But instead of succumbing to the defensive assault, they survive and germinate within the cells, traveling with the macrophages in their normal sentinel duty throughout the body to the lymph nodes, and eventually onto the bloodstream, ultimately leading to fatal systemic shock if treatment fails."

Another pertinent reference is the article entitled "Anthrax as Biological Weapon, 2002, Updated Recommendations for Management", written by Thomas V. Inglesby, M.D, et al., that appeared in the Journal of the American Medical Association, Vol. 287, No. 17, May 1, 2002 pages 2236–2252 ("Inglesby, 2002"), an entire copy of which is incorporated herein by reference. On page 2238 it states in part under the topic of "Microbiology" the following:

"*B anthracis* derives from the Greek word for coal, anthrakis, because of the black skin lesions it causes. *B anthracis* is aerobic, gram-positive, spore-forming, nonmotile *Bacillus* species."

On pages 2238–2239 of Inglesby, 2002, it states in part under the topic of "Pathogenesis and Clinical Manifestations" and "Inhalation Anthrax" the following:

"Inhalation anthrax follows deposition into alveolar spaces of spore-bearing particles in the 1- to 5-um range (38, 39). Macrophages then ingest the spores, some of which are lysed and destroyed. Surviving spores are transported via lymphatics to mediastinal lymph nodes, where germination occurs after a period of spore dormancy of variable and possibly extended duration (35, 40, 41). The trigger(s) responsible for the transformation of B anthracis spores to vegetative cells is not fully understood (42). In Sverdlovsk, cases occurred from 2 to 43 days after exposure (18). In experimental infection of monkeys, fatal disease occurred up to 58 days (40) and 98 days (43) after exposure. Viable spores were demonstrated in the mediastinal lymph nodes of 1 monkey 100 days after exposure (44)."

In one preferred embodiment of the invention, an Inhaler with a 50% mixture of *Eucalyptus globulus* and 50% *Melaleuca alternifolia* may be inhaled to prevent, treat, or cure airborne infection by *Bacillus anthracis.* Vapors from this mixture destroy the spores of the *Bacillus* and destroy any germinated *Bacillus anthracis.* These statements may be verified with suitable tests using the Test Chamber and by animal studies.

Therefore, the following general statements may be made.

In accordance with the invention, the inhalation of the vapor from a mixture comprised of 50% essential oil from *Eucalyptus globulus* and 50% essential oil from *Melaleuca alternifolia* can be used to prevent infection of the lungs caused by *Bacillus anthracis.*

In accordance with the invention, the inhalation of the vapor from a mixture comprised of 50% essential oil from

*Eucalyptus globulus* and 50% essential oil from *Melaleuca alternifolia* can be used to treat infections of the lungs caused by *Bacillus anthracis*.

In accordance with the invention, the inhalation of the vapor from a mixture of 50% essential oil from *Eucalyptus globulus* and 50% essential oil from *Melaleuca alternifolia* can be used to cure infections of the lungs caused by *Bacillus anthracis*.

In various sections herein, the essential oil from *Eucalyptus globulus* is called "*Eucalyptus globulus* essential oil" or simply "*Eucalyptus globulus*". The terms may be used interchangeably for the purposes herein.

In various sections herein, the essential oil from *Melaleuca alternifolia* is called "*Melaleuca alternifolia* essential oil" or simply "*Melaleuca alternifolia*".

Experiments with Inhalers having 50% essential oil from *Eucalyptus globulus* and 50% *Melaleuca alternifolia* can be done in the Inhaler Test Apparatus to determine the effective amount of vapor necessary to eradicate *Bacillus anthracis*. Similarly, animal studies can confirm the effective amount required. Similar experiments may be suitably performed to determine the effective amount of inhaled vapors to neutralize the presence of anthrax spores in the lungs.

Therefore, the No Sinus Pain™ Personal Lung Inhaler is a preferred embodiment of the invention used to prevent, treat, or cure infections of the human respiratory system by anthrax spores and by *Bacillus anthracis*. The Super Sinus and Lungs™ Personal Lung Inhaler manufactured by Inhalation, Inc. is also another preferred embodiment of the invention used to prevent, treat or cure infections of the human respiratory system by anthrax spores and by *Bacillus anthracis*.

The vapors from other essential oils, or mixtures of oils, may be suitably tested against the spores before germination, or against the germinated *Bacillus anthracis* using the Test Chamber. Those methods may suitably determine the effective amount of vapor necessary to eradicate the anthrax spores or to kill the *Bacillus anthracis*. Sufficient methods have already been described for that purpose.

Accordingly, the vapors from Mixture #1, Mixture #2, Mixture #3, Mixture #4, Mixture #5, and Mixture #6 which are defined above, and their respective examples, may be used to prevent, treat, and cure infections of *Bacillus anthracis*. The effective amounts of vapors are determined by various methods including those described in relation to the Test Chamber.

A good reference on smallpox is the article entitled "Smallpox as a Biological a Weapon, Medical and Public Health Management", by Donald A. Henderson, M.D., M.P.H., in the Journal of the American Medical Association, Vol. 281, No. 22, Jun. 9, 1999, pages 2177–2137 ("Henderson, 1999"), an entire copy of which is incorporated herein by reference. Page 2129 states in part under the topic of "Microbiology": "Smallpox, a DNA virus, is a member of the genus orthopoxyirus (20)."

Using the above methods and apparatus, the inhalation of strong vapors from a mixture of 50% essential oil from *Eucalyptus globulus* and 50% essential oil from *Melaleuca alternifolia* can be used to prevent, treat or cure infections of inhalation smallpox. The effective amounts of inhaled vapors necessary to prevent, treat or cure such infections may be determined by the above described experimental methods with the Inhaler Test Chamber or by suitable animal studies. Similarly, other vapors from essential oils, or mixtures of essential oils, may be used to prevent, treat or cure infections of inhalation smallpox.

A good reference on botulism is the article entitled "Botulinum Toxin as a Biological Weapon, Medical and Public Health Management" by Stephen S. Arnon, M.D., et al., Journal of the American Medical Association, Vol. 285, No. 8, Feb. 28, 2001, pages 1059–1070 ("Arnon, 2001"), an entire copy of which is incorporated herein by reference. Arnon, 2001 states in part on page 1061:

"*Clostridium botulinum* is a spore-forming, obligate aerobe whose natural habitat is soil, from which it can be isolated without undue difficulty. The species *C. botulinum* consists of 4 genetically diverse groups that would not otherwise be designated as a single species except for their common characteristic of producing *botulinum* toxin (33, 34). *Botulinum* toxin exists in 7 distinct antigenic types that have been assigned letters A through G."

Using the above methods and apparatus, the inhalation of strong vapors from a mixture of 50% essential oil from *Eucalyptus globulus* and 50% essential oil from *Melaleuca alternifolia* can be used to prevent, treat or cure infections of inhalation botulism. The effective amounts of inhaled vapors necessary to prevent, treat or cure such infections may be determined by the above described experimental methods with the Inhaler Test Chamber or by suitable animal studies. Similarly, other vapors from essential oils, or mixtures of essential oils, may be used to prevent, treat or cure infections of inhalation botulism.

A good reference on the plague is the article entitled "Plague as a Biological Weapon, Medical and Public Health Management" by Thomas V. Inglesby, M.D., et al., Journal of the American Medical Association", Vol. 283, No. 17, May 3, 2000, pages 2281–2290 (Inglesby, et al., 2000), an entire copy of which is incorporated herein by reference. Page 2283 of Inglesby, 2000 states in part under the category of "Microbiology and Virulence Factors" the following:

"*Y pestis (Yersinia pestis)* is a nonmotile, gram-negative *bacillus*, sometimes coccobacillus, that shows bipolar (also termed safety pin) staining with Wright, Giemsa, or Wayson stain . . . ".

Page 2283 of Inglesby, 2002 describes "primary septicemic plague", and "secondary pneumonic plague". That page further states:

"Secondary pneumonic plague develops in aminority of patients with bubonic or primary septicemic plague—approximately 12% of total cases in the United States over the last 50 years (4). This process, termed secondary pneumonic plague, develops via hematogenous spread of plague bacilli to the lungs. Patients commonly have symptoms of severe bronchopneumonia, chest pain, dyspnea, cough, and hemoptysis (16, 21)."

Using the above methods and apparatus, the inhalation of strong vapors from a mixture of 50% essential oil from *Eucalyptus globulus* and 50% essential oil from *Melaleuca alternifolia* can be used to prevent, treat or cure infections of inhalation plague. The effective amounts of inhaled vapors necessary to prevent, treat or cure such infections may be determined by the above described experimental methods with the Inhaler Test Chamber or by suitable animal studies. Similarly, other vapors from essential oils, or mixtures of essential oils, may be used to prevent, treat or cure infections of inhalation plague.

A good reference on tularemia is the article entitled "Tularemia as Biological Weapon, Medical and Public Health Management" by David T. Dennis, M.D., M.P.H., et al., in the "Journal of the American Medical Association", Vol. 285, No. 21, Jun. 6, 2001, pages 2763–2773 (Dennis, et al., 2001), an entire copy of which is incorporated herein by reference. Page 2764 of Dennis, et al., 2000) states in part:

"*Francisella tularensis* has long been considered a potential biological weapon. It was one of the number of agents studied at Japanese germ warfare research units operating in Manchuria between 1932 and 1945 (23)."

Page 2765 of Dennis, et al., 2000, states in part under the topic of "Natural Occurrences of Inhalation Tularemia" the following:

"The largest recorded airborne tularemia outbreak occurred in 1966–1967 in an extensive farming area of Sweden (43). This outbreak involved more than 600 patients infected with strains of the milder European biovar of *F tularensis* (*F tularensis* biovar palaerctica) [type B], most of whom acquired infection while doing farm work that created contaminated aerosols. Case exposures and disease onsets occurred during a period of months but peaked during the winter, when rodent-infested hay was being sorted and moved from field storage sites to barns."

Using the above methods and apparatus, the inhalation of strong vapors from a mixture of 50% essential oil from *Eucalyptus globulus* and 50% essential oil from *Melaleuca alternifolia* can be used to prevent, treat or cure infections of inhalation tularemia. The effective amounts of inhaled vapors necessary to prevent, treat or cure such infections may be determined by the above described experimental methods with the Inhaler Test Chamber or by suitable animal studies. Similarly, other vapors from essential oils, or mixtures of essential oils, may be used to prevent, treat or cure infections of inhalation tularemia.

A good reference on hemorrhagic fever viruses is the article entitled "Hemorrhagic Fever Viruses as Biological Weapons, Medical and Public Health Management", by Luciana Borio, M.D., et al., in the Journal of the American Medical Association, Vol. 287, No. 18, May 8, 2002, pages 2391–2405 (Borio, et al., 2002), an entire copy of which is incorporated herein by reference. Page 2392 of Borio, et al., 2002, presents the common names of such viruses, and their respective individual family and genus. Page 2392 of Borio et al., 2002, describes hemorrhagic fever viruses as including the following viruses with the common names first and with the corresponding genus in parentheses: Ebola virus (*Filorvirus*), Marburg virus (*Filovirus*), Lassa virus (*Arenavirus*), New World Arenaviridae virus (*Arenavirus*), Crimean-Congo hemorrhagic fever virus (*Nairovirus*), Rift Valley fever virus (*Phiebovirus*), Hemorrhagic fever with renal syndrome (*Hantavirus*), Dengue virus (*Flavivrus*), Yellow fever virus (*Flavivrus*), Omsk hemorrhagic fever virus (*Flavivirus*), and Kyasanur Forest disease (*Flavivirus*).

Using the above methods and apparatus, the inhalation of strong vapors from a mixture of 50% essential oil from *Eucalyptus globulus* and 50% essential oil from *Melaleuca alternifolia* can be used to prevent, treat or cure infections of inhalation hemorrhagic fever viruses. The effective amounts of inhaled vapors necessary to prevent, treat or cure such infections may be determined by the above described experimental methods with the Inhaler Test Chamber or by suitable animal studies. Similarly, other vapors from essential oils, or mixtures of essential oils, may be used to prevent, treat or cure infections of inhalation hemorrhagic fever viruses.

Accordingly, a preferred embodiment of the invention is the method to reduce the risks of infection of the human respiratory system by *Bacillus anthracis* in an area subject to bioterrorism attack comprising the following steps:

(a) within a period of time of 30 minutes before entering the area subject to bioterrorism attack, inhaling from a hand-held inhaler device an effective amount of the concentrated vapors from a mixture comprising 50% of essential oil from *Eucalyptus globulus* and 50% essential oil from *Melaleuca alternifolia;* and (b) after entering the area subject to bioterrorism attack, periodically inhaling the effective amount of the concentrated vapors from the mixture in the hand-held inhaler device, whereby the period of time between successive inhalations exceeds 30 minutes, and whereby the period of time between successive inhalations is less than 2 hours.

The effective amount described in the previous paragraph may be determined as follows. Experiments with Inhalers having 50% essential oil from *Eucalyptus globulus* and 50% *Melaleuca alternifolia* can be done in the Inhaler Test Apparatus to determine the effective amount of vapor necessary to eradicate *Bacillus anthracis*. Similarly, animal studies can confirm the effective amount required. Similarly experiments may be suitably performed to determine the effective amount to neutralize the presence of anthrax spores in the lungs.

In accordance with the above, a preferred embodiment of the invention is the method to treat human patients exposed to inhalation anthrax spores that includes at least the step of repetitively inhaling an effective amount of the concentrated vapors from a hand-held inhaler apparatus possessing a mixture comprised of 50% of essential oil from *Eucalyptus globulus* and 50% essential oil from *Melaleuca alternifolia*, whereby the period of time between successive inhalations exceeds 30 minutes, and whereby the period of time between successive inhalations is less than 2 hours.

The effective amount described in the previous paragraph may be determined as follows. Experiments with Inhalers having 50% essential oil from *Eucalyptus globulus* and 50% *Melaleuca alternifolia* can be performed in the Inhaler Test Apparatus to determine the effective amount of vapor necessary to eradicate or neutralize the anthrax spores. Similarly, animal studies can confirm the effective amount required. Similar experiments may be suitably performed to determine the effective amount to neutralize the presence of anthrax spores in the lungs.

In view of the above disclosure, yet another preferred embodiment of the invention is method to treat the lungs of a patient infected by *Bacillus anthracis* that includes at least the step of repetitively inhaling an effective amount of the concentrated vapors from a hand-held inhaler apparatus possessing a mixture comprised of 50% of essential oil from *Eucalyptus globulus* and 50% essential oil from *Melaleuca alternifolia,* whereby the period of time between successive inhalations exceeds 30 minutes, and whereby the period of time between successive inhalations is less than 2 hours. The "effective amount" may be determined as stated in the previous paragraph.

In view of the above, yet another preferred embodiment of the invention is the method to reduce the risks of infection of the human respiratory system by bioterrorism inhalation pathogens that includes at least the step of the inhalation of concentrated vapors from a mixture comprised of 50% essential oil of *Eucalyptus globulus* and 50% essential oil of *Melaleuca alternifolia,* whereby the mixture has selected antibacterial, antiviral, and antifungal properties, and whereby the bioterrorism pathogens are selected from the group comprised of inhalation anthrax, inhalation smallpox, inhalation botulism, inhalation plague, inhalation tularemia, inhalation hemorrhagic fever viruses, and inhalation tuberculosis.

The particular embodiment in the previous paragraph is significant. Here, the phrase "an effective amount of concentrated vapors" is not used. This is deliberate because of the following scenario. Suppose that a bioterrorism attack has occurred in my city (Bothell, Wash.). Suppose early indications are that a "white powder" was used and released by aircraft. Suppose further that it is not yet known what an "effective amount" of vapor is to prevent or cure infections of *Bacillus anthracis*. As an individual, and upon receipt of such news, I will immediately begin inhaling vapors from the No Sinus Pain™ Personal Lung Inhaler manufactured by Inhalation, Inc. that possesses 50% essential oil from *Eucalyptus globulus* and 50% essential oil from *Melaleuca alternifolia*. The reasons are as follows. First, there is no downside risk for inhaling from the Inhaler. Second, it is possible that there may be effective amounts of vapor inhaled to prevent or cure infections from *Bacillus anthracis*. Third, even if less than an effective amount of vapor is inhaled, the vapors will nevertheless reduce infections of other pathogens susceptible to the vapors that may be present in my lungs thereby allowing my own immune system to respond better to the infection of *Bacillus anthracis*. Fourth, what good is a vaccine against *Bacillus anthracis* to me if it is not immediately available to me personally? Fifth, what good is the news to me that it was a real anthrax attack if it takes 3 days for national labs to determine that it was anthrax, and I have already been fatally infected? These reasons are called the "Five Reasons for Using the Inhaler Following the News of a Bioterrorism Attack". The idea here is to catch the initial infection of the anthrax spores early, or during the initial stages of germination of the *Bacillus anthracis* before those bacteria overwhelm my immune system. Therefore, this useful invention that solves a novel problem of what to do with incomplete information available to any one individual following the news of a bioterrorism attack.

In view of the above, another preferred embodiment of the invention is the method to treat the lungs of a patient that may have been infected by bioterrorism pathogens that includes at least the step of repetitively inhaling the concentrated vapors from a hand-held inhaler apparatus possessing a mixture comprised of 50% of essential oil from *Eucalyptus globulus* and 50% essential oil from *Melaleuca alternifolia,* whereby the mixture has selected antibacterial, antiviral, and antifungal properties, whereby the period of time between successive inhalations exceeds 30 minutes, and whereby the period of time between successive inhalations is less than 2 hours, and whereby the bioterrorism pathogens are selected from the list comprised of inhalation anthrax, inhalation smallpox, inhalation botulism, inhalation plague, inhalation tularemia, inhalation hemorrhagic fever viruses, and inhalation tuberculosis. This is a useful invention because of the previously defined "Five Reasons for Using the Inhaler Following the News of a Bioterrorism Attack".

In view of the above, yet another preferred embodiment of the invention is the method to reduce the risks of infection of the human respiratory system by bioterrorism inhalation pathogens that includes at least the step of the inhalation of concentrated vapors from a mixture of essential oils having antiseptic properties that are safe to inhale, whereby the antiseptic properties include selected antibacterial properties, selected antiviral properties, and selected antifungal properties, and whereby the bioterrorism pathogens are selected from the group consisting of inhalation anthrax, inhalation smallpox, inhalation botulism, inhalation plague, inhalation tularemia, inhalation hemorrhagic fever viruses, and inhalation tuberculosis. This is a useful invention because of the previously defined "Five Reasons for Using the Inhaler Following the News of a Bioterrorism Attack". Furthermore, here specific reference is made to a "mixture of essential oils having antiseptic properties that are safe to inhale, whereby the antiseptic properties include selected antibacterial properties, selected antiviral properties, and selected antifungal properties". Several preferred embodiments of this invention have taught that each different essential oil has selective effectiveness against different pathogens (bacteria, viruses and fungi). However, virtually all the essential oils listed in the "List of Essential Oils" have at least some antipathogenic activities. This is so because the essentials oils within the plants have naturally evolved to selectively protect the plants from different bacteria, viruses and fungi. Therefore, this preferred embodiment teaches that it is useful to inhale the vapors from essential oils of plants because of the antiseptic properties of the essential oils. This fundamental point has been heretofore overlooked as it applies to the prevention, treatment and cure of diseases by using the antiseptic properties of inhaled essential oils. In many embodiments of the invention, the inhalation of concentrated vapors from essential oils are used as antiseptic agents to prevent initial infection. In other embodiments of the invention, the inhalation of concentrated vapors from essential oils are used as antiseptic agents to treat or cure an initial infection immediately after exposure to a pathogen. Using the vapors immediately after exposure significantly improves the odds of successfully treating or curing any resulting infection. Again, this is a useful invention particularly in view of the incomplete information that will be available during the initial phases of a bioterrorism attack.

Accordingly, the vapors from Mixture #1, Mixture #2, Mixture #3, Mixture #4 and Mixture #5 above may be used to prevent, treat, and cure infections of different bioterrorism pathogens. The effective amounts of vapors are determined by various methods including those described in relation to the Test Chamber. In accordance with the above, the vapors from 100% *Melaleuca alternifolia* may be used in a preferred embodiment of the invention to prevent, treat, and cure bioterrorism pathogens.

Accordingly, the No Sinus Pain™ Personal Lung Inhaler is a preferred embodiment of the invention used to prevent, treat, or cure infections of the human respiratory system by bioterrorism pathogens. The Super Sinus and Lungs™ Personal Lung Inhaler manufactured by Inhalation, Inc. is also another preferred embodiment of the invention used to prevent, treat or cure infections of the human respiratory system by bioterrorism pathogens.

Sinusitis

An important reference in this field appears in the book by Robert Berkow, M.D., Editor in Chief, and Mark H. Beers M.D., Associate Editor, that is entitled "The Merck Manual of Medical Information", "Home Edition", Pocket Books, a division of Simon & Schuster, Inc., New York, N.Y., 1997, (Berkow and Beers, 1997), an entire copy of which is incorporated herein by reference. All references cited in Berkow and Beers, 1997 are also incorporated herein in their entirety by reference. In particular, the Chapter entitled "Nonallergic Rhinits" on pages 1015–1017 of Berkow and Beers, 1997, are incorporated herein by reference.

Page 1016 of Berkow and Beers, 1997 states: "Sinusitis is an inflammation of the sinuses caused by an allergy or a viral, bacterial, or fungal infection."

Page 1016 of Berkow and Beers, 1997, further states under the subtitle of "Causes" the following:

"Sinusitis may be acute (short-lived) or chronic (long-standing). Acute sinusitis may be caused by a variety of bacteria and often develops after a viral infection of the upper airways, such as the common cold. Occasionally, chronic sinusitis of the maxillary sinus results from a tooth infection.

During a cold, the swollen mucous membrane of the nasal cavity tends to block the openings of the sinuses. When this happens, air in the sinuses is absorbed into the bloodstream, and the pressure inside the sinuses decreases, resulting in a negative pressure that's painful—a condition called vacuum sinusitis. If the vacuum remains, fluid is drawn into and fills the sinuses, creating a breeding ground for bacteria. White blood cells and more fluid enter the sinuses to fight the bacteria; this influx increases the pressure and causes more pain."

Page 1017 of Berkow and Beers, 1997, states under the topic of "Treatment" the following: "Treatment of acute sinusitis is aimed at improving sinus drainage and curing the infection."

Page 1017 of Berkow and Beers, 1997, states under the topic of "Sinusitis and an Impaired Immune System" the following:

"In people who have poorly controlled diabetes or an impaired immune system, fungi can cause severe and even fatal sinusitis." . . . "Spergillosis and candidiasis are often fatal fungal infections that may develop in the sinuses of people whose immune system is impaired by anticancer treatment or by diseases such as leukemia, lymphoma, multiple myeloma, or AIDS."

Section 7 (Ear, Nose, And Throat Disorders), Chapter 86 (Nose and Paranasal Sinuses" of Beers, et al., 1999, op. cit., discusses the topic of "Sinusitis". This Chapter 86 states in part under the topic of "Sinusitis" the following: "Inflammation of the paranasal sinuses due to viral, bacterial or fungal infections or allergic reactions."

Section 7, Chapter 86 of Beers, et al., 1999 further states in part: "Acute sinusitis is caused to streptococci, pneumococci, *Haemophilus influenzae,* or staphylococci and is usually precipitated by an acute viral respiratory tract infection. Chronic sinusitis may be exacerbated by a gram-negative rod or anaerobic microorganisms. In aminority of cases, chronic maxillary sinusitis is secondary to dental infection."

Section 7, Chapter 86 of Beers, et al., 1999, further states under the topic of "Sinusitis in Metabolically or Immunocologically Compromised Patients" the following:

"Mucormycosis (phycomycosis)—a mycosis due to fungi of the order of Mucorales, including species of *Mucor, Absidia,* and *Rhizopus*—may develop in patients with poorly controlled diabetes. It is characterized by black, devitalized tissue in the nasal cavity and neurological signs secondary to retrograde thromboarteritis in the carotid arterial system"

Another useful reference on this subject is entitled "Allergy, Asthma, and Sinus" on the World Wide Web (http://allergy-asthma-sinus.com/) dated Apr. 8, 2002 by the Allergy, Asthma and Sinus Resource Center, Miami, Fla. that was printed-out on Apr. 30, 2002, (Allergy, Asthma and Sinus Resource Center, 2002), an entire copy of which is incorporated herein by reference.

The Allergy, Asthma and Sinus Resource Center, 2002, states in part under the topic of "Chronic Sinusitis Facts:

"Chronic sinusitis affects over 37 million Americans a year;"

"Bacteria, Fungi, and viruses can be a cause of sinusitis;"

"A large number of people with AIDS, Asthma, or Cystic Fibrosis also suffer from sinusitis;"

"Some sinusitis conditions can cause you to have severe headaches;"

"Because many symptoms of sinusitis coincide with those of a cold, many people with sinusitis fail to seek proper treatment;"

"Even though sinuses aren't fully developed until approximately the age of 20, they can still present problems to people under the age of 20;"

"Sinusitis is the most common chronic condition in the United States;"

"On average, sinusitis sufferers miss four days of work per year due to their sinus condition."

Another useful reference on this subject is the article entitled "Sinusitis (Sinus Infection)" on the World Wide Web Site entitled "Medical College of Wisconsin Physicians & Clinics" (http://www.healthlink.mcw.edu/), printed out on Apr. 30, 2002, ("Medical College of Wisconsin Physicians & Clinics, 2002"), an entire copy of which is incorporated herein by reference.

The Medical College of Wisconsin Physicians & Clinics, 2002, states in part:

"Sinusitis simply means inflammation of the sinuses, but this gives little indication of the misery and pain this condition can cause. Chronic sinusitis, sinusitis that recurs frequently, affects an estimated 32 million people in the United States. Americans spend millions of dollars each year for medications that promise relief from their sinus symptoms."

The Medical College of Wisconsin Physicians & Clinics, 2002, states under the title of "Causes" the following:

"Viruses can enter the body through the nasal passages and set off a chain reaction resulting in sinusitis. For example, the nose reacts to an invasion by viruses that cause infections such as the common colds, flus, or measles by producing mucus and sending white blood cells to the lining of the nose, which congest and swell the nasal passages. When this swelling involves the adjacent mucus membranes of the sinuses, air and mucus are trapped behind the narrowed openings of the sinuses. If the sinus openings become too narrow to permit drainage of the mucus, then bacteria, which normally are present in the respiratory tract, begin to multiply. Most apparently healthy people harbor bacteria, such a *Streptococcus pneumoniae* and *Haemophilus influenzae,* in their upper respiratory tracts with no ill effects until the body's defenses are weakened or drainage from the sinuses is blacked by a cold or other viral infection. The bacteria that may have been living harmlessly in the nose, throat, or sinus area can multiply and cause an acute sinus infection."

Another useful reference in this field is the article entitled "Sinusitis" that was published on the World Wide Web Site entitled "drkoop.com", that was printed out on Apr. 30, 2002, ("DrKoop.com, 2002"), an entire copy of which is incorporated herein by reference.

DrKoop.com, 2002, states in part:

"Acute sinusitis affects approximately 3 out of 1,000 people. There are 4 pairs of sinuses connected to the nasal cavity by small openings. Normally, air passes in and out of the sinuses and mucous and fluid draining from the sinuses into the nose."

DrKoop.com, 2002, further states in part under the topic of "Complications":

"chronic sinusitis"

"spread of infection into the bones of he face (osteomyelitis)"
"spread of infection into the brain (meningitis)"
"abscess formation"
"cavernous sinus thrombosis"

Experimental inhalers have been made by applicants having 50% *Eucalyptus globulus* and 50% *Melaleuca alternifolia*. If sinuses are partially restricted, and following the inhalation of vapors from this mixture, the sinuses of most people "open" within 30 seconds to 2 minutes. This is a spectacular effect that has been repeated with many individuals. This "sinus opening effect", or "sinus unclogging effect", or "sinus dilation effect" allows the sinuses to properly drain, thereby preventing any additional infection of the sinuses. This "sinus opening effect", or "sinus unclogging effect", or "sinus dilation effect" allows the antipathogenic vapors to enter the sinuses thereby eliminating any underlying bacterial, fungal or viral infection causing the sinusitis.

Vapors from the 50% *Eucalyptus globulus* and 50% *Melaleuca alternifolia* mixture of essential oils are broadly antipathogenc. Those vapors are effective against many of the pathogens on the above defined list. In particular, they are effective against many of the pathogens that specifically cause sinusitis. These pathogens specifically include the listed bacteria, viruses and fungi.

Therefore, the following general statements may be made.

In accordance with the invention, the inhalation of the vapor from 50% *Eucalyptus globulus* and 50% *Melaleuca alternifolia* can be used to prevent sinusitis that is caused by infectious pathogens.

In accordance with the invention, the inhalation of the vapor from 50% *Eucalyptus globulus* and 50% *Melaleuca alternifolia* can be used to prevent the initial infection of bacteria, viruses, and fungi that cause sinusitis.

In accordance with the invention, the inhalation of the vapor from 50% *Eucalyptus globulus* and 50% *Melaleuca alternifolia* can be used to cure sinusitis that is caused by infectious pathogens.

In accordance with the invention, the inhalation of the vapor from 50% *Eucalyptus globulus* and 50% *Melaleuca alternifolia* can be used to cure the infection of bacteria, viruses, and fungi that cause sinusitis.

In accordance with the invention, the inhalation of the vapor from 50% *Eucalyptus globulus* and 50% *Melaleuca alternifolia* can be used to treat sinusitis that is caused by infectious pathogens.

In accordance with the invention, the inhalation of the vapor from 50% *Eucalyptus globulus* and 50% *Melaleuca alternifolia* can be used to treat the infection of bacteria, viruses, and fungi that cause sinusitis.

In accordance with the invention, the inhalation of the vapor from any mixture of *Eucalyptus globulus* and *Melaleuca alternifolia* can be used to prevent sinusitis that is caused by infectious pathogens.

In accordance with the invention, the inhalation of the vapor any mixture of *Eucalyptus globulus* and *Melaleuca alternifolia* can be used to prevent the initial infection of bacteria, viruses, and fungi that cause sinusitis.

In accordance with the invention, the inhalation of the vapor from any mixture of *Eucalyptus globulus* and *Melaleuca alternifolia* can be used to cure sinusitis that is caused by infectious pathogens.

In accordance with the invention, the inhalation of the vapor from any mixture of *Eucalyptus globulus* and *Melaleuca alternifolia* can be used to cure the infection of bacteria, viruses, and fungi that cause sinusitis.

In accordance with the invention, the inhalation of the vapor from any mixture of *Eucalyptus globulus* and *Melaleuca alternifolia* can be used to treat sinusitis caused by infectious pathogens.

In accordance with the invention, the inhalation of the vapor from any mixture of *Eucalyptus globulus* and *Melaleuca alternifolia* can be used to treat the infection of bacteria, viruses, and fungi that cause sinusitis.

The No Sinus Pain™ Personal Lung Inhaler manufactured by Inhalation, Inc. is a preferred embodiment of the invention used to prevent, treat or cure the infection of bacteria, viruses, and fungi that cause sinusitis. The Super Sinus and Lungs™ Personal Lung Inhaler manufactured by Inhalation, Inc. is also another preferred embodiment of the invention used to prevent, treat or cure the infection of bacteria, viruses, and fungi that cause sinusitis.

In accordance with the invention, the antipathogenic properties of vapors from any essential oil listed on the above defined "List of Essential Oils" can be tested in the apparatus defined above in the section entitled "Test Chamber". Those vapors showing antipathogenic properties against the pathogens causing sinusitis can be identified using that apparatus and the procedures described in these sections. That essential oil may then be provided in one or more of the Inhaler apparatus shown herein. Inhaled vapors from the chosen Inhaler apparatus may be used to prevent or cure sinusitis that is caused by infectious pathogens.

In accordance with the invention, the antipathogenic properties of vapors from any mixture of essential oil listed on the above defined "List of Essential Oils" can be tested in the apparatus defined above in the section entitled "Test Chamber". Those vapors showing antipathogenic properties against the pathogens causing sinusitis can be identified using that apparatus and the procedures described in those sections. That essential oil may then be provided in one or more of the Inhaler apparatus shown herein. Inhaled vapors from a selected Inhaler Apparatus may be used to prevent or cure sinusitis that is caused by infectious pathogens.

Accordingly, the vapors from Mixture #1, Mixture #2, Mixture #3, Mixture #4, Mixture #5, and Mixture #6 which are defined above, and their respective examples, may be used to prevent, treat, and cure the infection of bacteria, viruses, and fungi that cause sinusitis. The effective amounts of vapors are determined by various methods including those described in relation to the Test Chamber. In view of the above, a preferred embodiment of the invention includes inhaling the vapors from 100% *Melaleuca alternifolia* to prevent, treat, and cure the infection of bacteria, viruses, and fungi that cause sinusitis.

Many individuals report that the No Sinus Pain™ Personal Lung Inhaler manufactured by the firm Inhalation, Inc. may be used to open up partially clogged sinuses within 30 second to 2 minutes. Here the phrase "partially obstructed sinuses" may be used interchangeable with the phrase "partially clogged sinuses".

Rhinitis

The document entitled "Rhinitis" of Section 7 (Ear, Nose, and Throat Disorders), Chapter 86 (Nose And Paranasal Sinuses) of Beers, et al., 1999, op. cit., an entire copy of which is incorporated herein by reference, defines various pathogens causing rhinitis. In addition, the section entitled "Nonallergic Rhinitis" Berkow and Beers, 1997, op. cit., an entire copy of which is incorporated herein by reference, also describes various pathogens causing rhinitis.

It is evident that the above invention may be used to prevent, treat or cure rhinitis that is caused by various infectious pathogens. The methods and apparatus necessary to prevent, treat or cure rhinitis is evident from the above disclosure and will not be repeated here in the interests of brevity.

Asthma

Pages 195–200 of Balch and Balch, 2000, op. cit., an entire copy of which is incorporated herein by reference, states in part the following: "There are two forms of asthma: allergic and nonallergic, although the two often occur together." In general, nonallergic asthma is presumed to be related to infections by bacterial, viral, or fungal infections. In general, allergic asthma is not necessarily caused by underlying pathogenic infections, but it often exasperated by such underlying bacterial, viral of fungal pathogenic infections.

Pages 173–180 of Berkow and Beers, 1997, an entire copy of which is incorporated herein by reference, defines Asthma as the following: "Asthma is a condition in which the airways are narrowed because hyperactivity to certain stimuli produces inflammation; the airway narrowing is reversible." Infections by pathogens including bacteria, viruses and fungi can exasperate any condition of asthma.

Berkow and Beers, 1997, defines Chronic Obstructive Pulmonary Disease (COPD) as the following: "Chronic obstructive pulmonary disease (COPD) is persistent obstruction of the airways caused by emphysema or chronic bronchitis." Infections by pathogens including bacteria, viruses and fungi can exasperate any condition of COPD.

Please refer to "FIG. 68-1. Interrelationships of chronic obstructive pulmonary disease (COPD), chronic bronchitis, emphysema, and asthma" in Section 6 (Pulmonary Disorders), Chapter 68 (Chronic Obstructive Airway Disorders"), of Beers, et. al, 1999, an entire copy of which is incorporated herein by reference, which shows the Venn Diagram. That shows a relationship between asthma, chronic bronchitis and emphysema and COPD. Certain pathogenic infections of bacteria, viruses and fungi can cause "pathogenic asthma". Certain pathogenic infections of bacteria, viruses, and fungi can cause "pathogenic bronchitis". Certain pathogenic infections of bacteria, viruses, and fungi can cause "pathogenic emphysema".

Certain forms of asthma such as allergic asthma, is not necessarily caused by a pathogenic infection, but it is exasperated by such an infection.

Certain forms of emphysema are not caused by an initial pathogenic infection, but it is exasperated by such an infection.

Vapors from the 50% *Eucalyptus globulus* and 50% *Melaleuca alternifolia* mixture of essential oils are broadly antipathogenc. Those vapors are effective against many of the pathogens on the above defined lists. In particular, they are effective against many of the pathogens that specifically cause pathogenic asthma, pathogenic bronchitis, and pathogenic emphysema. These pathogens specifically include the listed bacteria, viruses and fungi.

It is evident that the above invention may be used to prevent, treat or cure pathogenic asthma. The methods and apparatus necessary to prevent, treat or cure pathogenic asthma are evident from the above disclosure and will not be repeated in the interests of brevity.

It is evident that the above invention may be used to prevent, treat or cure pathogenic bronchitis. The methods and apparatus necessary to prevent, treat or cure pathogenic bronchitis are evident from the above disclosure and will not be repeated in the interests of brevity.

It is evident that the above invention may be used to prevent or treat pathogenic emphysema. The methods and apparatus necessary to prevent or treat pathogenic emphysema are evident from the above disclosure and will not be repeated in the interests of brevity. To the extent that the human lungs can rejuvenate under the conditions of no additional infections (as is the case for the inventor of William Banning Vail III, see the below), then the methods and apparatus necessary to remedy or partially cure emphysema are also disclosed in this invention.

In the following, pathogens include bacteria, viruses, and fungi of the type that infect the human respiratory system which have been previously described in the above "List of Pathogens" and elsewhere.

From the above disclosure, it is evident that:

In accordance with the invention, the inhalation of the vapor from 50% *Eucalyptus globulus* and 50% *Melaleuca alternifolia* can be used to prevent infection of the lungs by *Staphylococcus aureus* causing a form of pathogenic asthma.

In accordance with the invention, the inhalation of the vapor from 50% *Eucalyptus globulus* and 50% *Melaleuca alternifolia* can be used to prevent the initial infection of the lungs by pathogens causing pathogenic asthma.

In accordance with the invention, the inhalation of the vapor from 50% *Eucalyptus globulus* and 50% *Melaleuca alternifolia* can be used to cure the lungs infected by *Staphylococcus aureus* causing a form of pathogenic asthma.

In accordance with the invention, the inhalation of the vapor from 50% *Eucalyptus globulus* and 50% *Melaleuca alternifolia* can be used to cure the infection of the lungs by pathogens causing pathogenic asthma.

In accordance with the invention, the inhalation of the vapor from 50% *Eucalyptus globulus* and 50% *Melaleuca alternifolia* can be used to treat the lungs infected by *Staphylococcus aureus* causing a form of pathogenic asthma.

In accordance with the invention, the inhalation of the vapor from 50% *Eucalyptus globulus* and 50% *Melaleuca alternifolia* can be used to treat the infection of the lungs by pathogens causing pathogenic asthma.

In accordance with the invention, the inhalation of the vapor from any mixture of *Eucalyptus globulus* and *Melaleuca alternifolia* can be used to prevent infection of the lungs by *Staphylococcus aureus* causing a form of pathogenic asthma.

In accordance with the invention, the inhalation of the vapor from any mixture of *Eucalyptus globulus* and *Melaleuca alternifolia* can be used to prevent the initial infection of the lungs by pathogens causing pathogenic asthma.

In accordance with the invention, the inhalation of the vapor from any mixture of *Eucalyptus globulus* and *Melaleuca alternifolia* can be used to cure the lungs infected by *Staphylococcus aureus* causing a form of pathogenic asthma.

In accordance with the invention, the inhalation of the vapor from any mixture of *Eucalyptus globulus* and *Melaleuca alternifolia* can be used to cure the infection of the lungs by pathogens causing pathogenic asthma.

In accordance with the invention, the inhalation of the vapor from any mixture of *Eucalyptus globulus* and *Melaleuca alternifolia* can be used to treat the lungs infected by *Staphylococcus aureus* causing a form of pathogenic asthma.

In accordance with the invention, the inhalation of the vapor from any mixture of *Eucalyptus globulus* and *Melaleuca alternifolia* can be used to treat the lungs infected by pathogens causing pathogenic asthma.

The No Sinus Pain™ Personal Lung Inhaler manufactured by Inhalation, Inc. is a preferred embodiment of the invention used to prevent, treat or cure the infection of lungs by pathogens causing pathogenic asthma. The Super Sinus and Lungs™ Personal Lung Inhaler manufactured by Inhalation, Inc. is also another preferred embodiment of the invention used to prevent, treat or cure the infection of lungs by pathogens causing pathogenic asthma.

Similar statements to the above 12 statements are hereby made by reference with regards to any of the above listed specific pathogens in this document, for example, any bacterium such as *Mycobacterium tuberculosis,* any viruses including the rhinoviruses and Influenza B, and any fungi including *Coccidioides immitis* and/or *Blastomyces dermatitedis.*

In accordance with the invention, the antipathogenic properties of vapors from any essential oil listed on the above defined "List of Essential Oils" can be tested in the apparatus defined in the section entitled "Test Chamber". Those vapors showing antipathogenic properties against the pathogens causing pathogenic asthma, pathogenic bronchitis, or pathogenic emphysema can be identified using that apparatus and the procedures described in those sections. That essential oil may then be provided in one or more of the Inhaler apparatus shown herein. In accordance with the invention, inhaled vapors from a selected Inhaler apparatus may be used to prevent, treat, or cure infections by pathogens causing pathogenic asthma, pathogenic bronchitis, and/or pathogenic emphysema.

In accordance with the invention, the antipathogenic properties of vapors from any mixture of essential oil listed on the above defined "List of Essential Oils" can be tested in the apparatus defined in the above section entitled "Test Chamber". Those vapors showing antipathogenic properties against the pathogens causing pathogenic asthma, pathogenic bronchitis, and pathogenic emphysema can be identified using the apparatus and the procedures described those sections. That essential oil may then be provided in one or more Inhaler apparatus shown herein. In accordance with the invention, inhaled vapors from a selected Inhaler Apparatus may be used to prevent, treat or cure infections of pathogens causing pathogenic asthma, pathogenic bronchitis, and pathogenic emphysema.

Accordingly, vapors from Mixture #1, Mixture #2, Mixture #3, Mixture #4, Mixture #5, and Mixture #6 which are defined above, and their respective examples, may be used to prevent, treat, and cure infections of pathogens causing pathogenic asthma, pathogenic bronchitis, and pathogenic emphysema. The effective amounts of vapors are determined by various methods including those described in relation to the Test Chamber. In accordance with the above, the vapors from 100% *Melaleuca alternifolia* may be used in a preferred embodiment of the invention to prevent, treat, and cure infections of pathogens causing pathogenic asthma, pathogenic bronchitis, and pathogenic emphysema.

Pneumonia

Under the subject of "Pneumonia" on pages 567–571, in Balch and Balch, 2000, op. cit., an entire copy of which is incorporated herein by reference, it states the following:

"Pneumonia is a serious infection of the lungs that can be caused by any of a number of different infectious agents, including viruses, bacteria, fungi, protozoa, and mycoplasma. The infection causes tiny air sacs in the lung area to become inflamed and filled with mucus and pus, inhibiting oxygen from reaching the blood. Lobar pneumonia affects only a section, or lobe of one lung. Bronchial pneumonia affects portions of both lungs. Although symptoms can vary in intensity, they usually include fever, chills, cough, bloody sputum, muscle aches, fatigue, sore throat, enlarged lymph glands in the neck, cyanosis (a bluish cast to the skin and nails), pain in the chest, and rapid, difficult respiration."

"Pneumonia is typically preceded by an upper respiratory infection such as a cold, influenza, or measles. Factors that increase the risk of pneumonia being either under one year or over sixty years of age, a weakened immune system, cardiovascular disease, diabetes, HIV infection, seizure or stroke, aspiration under anesthesia, alcoholism, smoking, kidney failure, sickle cell disease, malnutrition, foreign bodies in the respiratory passages, exposure to chemical irritants, and even allergies"

"Bacterial pneumonia can be very dangers and may come on either suddenly or gradually, usually as a complication of some other health problem such as respiratory disease, a weakened immune system, or viral infection. Older adults, young children, alcoholics, and people have just undergone surgery are also at risk. *Streptococcus pneumonia* is the most common cause of bacterial pneumonia. Symptoms usually include shaking, chills, and a high temperature. The cough is dry at first. Then a rust-colored sputum is produced, and breathing becomes rapid and labored. Chest pain that worsens upon inhalation, abdominal pain, and fatigue are also common. This type of pneumonia is unlikely to spread from one person to another."

"Viral pneumonia is more variable in course and severity. It can come on suddenly or gradually, and symptoms—which are much the same as those of bacterial pneumonia—can be mild, sever, or anywhere in between. It is less serious than bacterial pneumonia, but if not cared for properly, a second, bacterial pneumonia infection can set in."

"Fungal pneumonia, especially *Pneumocystis carinii* pneumonia (PCP), is much less common than either the bacterial or viral variety, and is often associated with a weakened or suppressed immune system. People with HIV, AIDS or certain types of cancer, or who are taking immunosuppressive drugs following organ transplantation, are most likely to be affected."

'*Mycoplasma pneumonia,* or "walking pneumonia" is caused by an agent that is unclassified but appears to be both bacterium and virus. This form of pneumonia usually affects people under forty. The symptoms tend to be less sever than those of viral or bacterial pneumonia and include a cough that is spasmodic, along with chills and a fever"

"Infants can contract pneumonia due to a *Chlamydia trachomaties* infection transferred to the child during birth. childhood pneumonia can also be cased by the same bacteria that cause whooping cough"

"Young children (especially infants), older adults, and people who have compromised immune systems are very vulnerable to the potentially life-threatening effects of this illness. Pneumonia is now the fifth leading cause of death in the United States. No matter what the cause, pneumonia usually leaves the sufferer with weakness that persists for four to eight weeks after the acute phase of the infection has resolved."

Under the topic of "General" of Section 6 (Pulmonary Disorders), Chapter 73 (Pneumonia), of Beers, et al., 1999, op. cit., an entire copy of which is incorporated herein by reference, it states the following:

"Bacteria are the most common cause of pneumonia in adults (over) 30 yr. Of these, *Streptococcus pneumonia* is the most common. Other pathogens included anaerobic bacteria, *Staphylococcus aureus, Haemophilus influenzae, Chlamydia pneumonia, C. psittaci, C. trachomatis, Moraxella (Branhamella) catarrhalis, Legionella penumophila, Klebsiella pneumonia,* and other gram-negative bacilli. *Mycoplasma pneumoniae,* a bacteria-like organism, is particularly common in older children and young adults, typically in the spring. Major pulmonary pathogens in infants and children are viruses: respiratory syncytial virus, parainfluenza virus, and influenza A and B viruses. These agents may also cause pneumonia in adults; however, the only common viruses in previously healthy adults are influenza A, occasionally influenza B, and rarely varicella-roster. Among other agents are higher bacteria including *Nocardia* and *Actinomyces* sp; mycobacteria, including *Mycobacterium tuberculosis* and a typical strains (primarily *M. kansassi* and *M. aviumintracellulare*); fungi, including *Histoplasma capsulatum, Coccidioides immitis, Blastomyces dermatitidis, Cryptococcus neoformans, Aspergillus fumigatas,* and *Pnumocystis carinii;* and rickettsaie, primarily *Coxiella burnetti* (Q fever)." u "The usual mechanisms of spread are inhaling droplets small enough to reach the alveoli and aspirating secretions from the upper airways. Other means include hematogenous or lymphatic dissemination and direct spread from contagious infections. Predisposing factor include upper respiratory viral infections, alcoholism, institionalization, cigarette smoking, heart failure, chronic obstructive airway disease, age extremes, debility, immunocompromised (as in diabetes mellitus and chronic renal failure), compromised consciousness, dysphagia, and exposure to tansmissable agents."

A copy under the topic of "Viral Pneumonia" of Section 6 (Pulmonary Disorders), Chapter 73 (Pneumonia), of Beers, et al., 1999, op. cit., an entire copy of which is incorporated herein by reference, it states the following:

"Many viruses can cause bronchitis, and a few cause pneumonia. Most common among infants and children are respiratory syncytial virus, parainfluenza virus, and influenza A and B viruses. Among otherwise healthy adults, the only frequency recognized viral pathogens are influenza A and B viruses. Infrequently, pneumonia in adults is caused by adenovirus, varicella-zoster virus, Epstein-Barr virus, coxsackievirus, and Hantavirus."

Under the topic of "Pneumonia Caused by Gram-Negative *Bacilli*" of Section 6 (Pulmonary Disorders), Chapter 73 (Pneumonia), Beers, et al.; 1999, op. cit., an entire copy of which is incorporated herein by reference, it states the following:

"Gram-negative *bacilli* account for (less than) 2% of community-acquired pneumonia but for most nosocomial pneumonia, including fatal ones. The most important pathogen is *Klebsiella pneumoniae,* which causes Friedlander's pneumonia. Other usual pathogens are *Pseudomonas aeruginosa, Escherichia coli, Enterobacter* sp., *Proteus* sp., *Serratia marcescens,* and *Acinetobacter* sp. *P. aeruginosa* is a common pathogen in patients with cystic fibrosis, neutopenia, advanced AIDS, bronchiectasis, and pneumonia acquired in intensive care."

Under the topic of "Fungal Infections" of Section 6 (Pulmonary Disorders), Chapter 73 (Pneumonia), of Beers, et al., 1999, op. cit., an entire copy of which is incorporated herein by reference, it states the following:

"Primary fungal pneumonia is caused most commonly by *Blastomyces dermatitidis, Histoplasma capsulatum,* or *Coccidiodes immitis* and less commonly by *Sporothrix schenckii* or *Cryptococcus, Aspergillus,* or *Mucor* sp (see Ch. 158). Fungal pneumonia may be a complication of antibacterial therapy, especially in patients with altered host defense mechanisms due to illness or immunosuppressive therapy and in those with AIDS (see Ch. 151.)"

The above defined bacteria, viruses, and fungi are in this section entitled "Pneumonia" are separately and collectively identified with the term "pathogens which cause pneumonia".

Vapors from the 50% *Eucalyptus globulus* and 50% *Melaleuca alternifolia* mixture of essential oils are broadly antipathogenc. Those vapors are effective against many of the pathogens on the above defined list. In particular, they are effective against many of the pathogens that invade the lungs of patients which cause pneumonia that are listed above.

In accordance with the previous disclosure in the invention, the following general statements may be made.

In accordance with the invention, the inhalation of the vapor from 50% *Eucalyptus globulus* and 50% *Melaleuca alternifolia* can be used to prevent infection of the lungs of patients by pathogens that cause pneumonia.

In accordance with the invention, the inhalation of the vapor from 50% *Eucalyptus globulus* and 50% *Melaleuca alternifolia* can be used to prevent the initial infection by bacteria, viruses and fungi that cause pneumonia.

In accordance with the invention, the inhalation of the vapor from 50% *Eucalyptus globulus* and 50% *Melaleuca alternifolia* can be used to cure pneumonia caused by infections of bacteria, viruses, and fungi.

In accordance with the invention, the inhalation of the vapor from 50% *Eucalyptus globulus* and 50% *Melaleuca alternifolia* can be used to cure infections of bacteria, viruses and fungi that cause pneumonia.

In accordance with the invention, the inhalation of the vapor from 50% *Eucalyptus globulus* and 50% *Melaleuca alternifolia* can be used to treat the infection of the lungs of patients by pathogens that cause pneumonia.

In accordance with the invention, the inhalation of the vapor from 50% *Eucalyptus globulus* and 50% *Melaleuca alternifolia* can be used to treat the initial infection by bacteria, viruses and fungi that cause pneumonia.

In accordance with the invention, the inhalation of the vapor from any mixture of *Eucalyptus globulus* and *Melaleuca alternifolia* can be used to prevent the initial infection by bacteria, viruses and fungi that cause pneumonia.

In accordance with the invention, the inhalation of the vapor any mixture of *Eucalyptus globulus* and *Melaleuca alternifolia* can be used to prevent the initial infection by bacteria, viruses and fungi that cause pneumonia.

In accordance with the invention, the inhalation of the vapor from any mixture of *Eucalyptus globulus* and *Melaleuca alternifolia* can be used to cure pneumonia caused by infections of bacteria, viruses, and fungi.

In accordance with the invention, the inhalation of the vapor from any mixture of *Eucalyptus globulus* and *Mela-*

*leuca alternifolia* can be used to cure infections of bacteria, viruses and fungi that cause pneumonia.

In accordance with the invention, the inhalation of the vapor from any mixture of *Eucalyptus globulus* and *Melaleuca alternifolia* can be used to treat the infection of the lungs of patients by pathogens that cause pneumonia.

In accordance with the invention, the inhalation of the vapor from any mixture of *Eucalyptus globulus* and *Melaleuca alternifolia* can be used to treat the initial infection by bacteria, viruses and fungi that cause pneumonia.

Similar statements to the above 12 statements are hereby made by reference with regards to the specific pathogen *Staphylococcus aureus, Haemophilus influenzae,* Influenza A, Influenza B, *Histoplasma capsulatum,* and/or *Blastomyces dermatitidis.*

The No Sinus Pain™ Personal Lung Inhaler manufactured by Inhalation, Inc. is a preferred embodiment of the invention used to prevent, treat or cure the infection of bacteria, viruses, and fungi that cause pneumonia. The Super Sinus and Lungs™ Personal Lung Inhaler manufactured by Inhalation, Inc. is also another preferred embodiment of the invention used to prevent, treat or cure the infection of bacteria, viruses, and fungi that cause pneumonia.

In accordance with the invention, the antipathogenic properties of vapors from any essential oil listed on the above defined "List of Essential Oils" can be tested in the apparatus defined in the above section entitled "Test Chamber". Those vapors showing antipathogenic properties against the pathogens causing pneumonia can be identified using that apparatus and the procedures described in those two sections. That essential oil may then be provided in one or more of the Inhaler apparatus shown herein. Inhaled vapors from a selected Inhaler apparatus may be used to prevent, treat or cure infections of bacteria, viruses and fungi causing pneumonia.

In accordance with the invention, the antipathogenic properties of vapors from any mixture of essential oil listed on the above defined "List of Essential Oils" can be tested in the apparatus defined in the above section entitled "Test Chamber". Those vapors showing antipathogenic properties against the pathogens causing pneumonia can be identified using that apparatus and the procedures described those two sections. That essential oil may then be provided in one or more Inhaler apparatus shown herein. Inhaled vapors from the selected Inhaler Apparatus may be used to prevent, treat or cure infections of the lungs by bacteria, viruses, and fungi causing pneumonia.

Accordingly, the vapors from Mixture #1, Mixture #2, Mixture #3, Mixture #4, Mixture #5, and Mixture #6 which are defined above, and their respective examples, may be used to prevent, treat, and cure infections of the lungs by bacteria, viruses, and fungi causing pneumonia. The effective amounts of vapors are determined by various methods including those described in relation to the Test Chamber. In accordance with the above, the vapors from 100% *Melaleuca alternifolia* may be used in a preferred embodiment of the invention to prevent, treat, and cure infections of the lungs by bacteria, viruses, and fungi that cause pneumonia.

Respiratory Viral Infections

The symptoms for Colds and Flus are discussed in the Balch and Balch, 2000, op. cit., in the following sections: (a) the section entitled "Common Cold" on pages 297–300; and (b) the section entitled "Influenza" on pages 468–470. An entire copy of these sections is included herein by reference.

Under the topic of "Respiratory Viral Diseases" in Section 13 (Infectious Diseases), Chapter 162 (Viral Diseases), of Beers, et al., 1999, op. cit., an entire copy of which is incorporated herein by reference, it states the following under the title of "The Common Cold":

> "Picornaviruses, especially rhinoviruses and certain echoviruses and coxsackievirses, cause the common cold. About 30 to 50% of all colds are caused by one of the (over) 100 stereotypes of rhinovirses. At any time only a few viruses are prevalent. Often a single virus is responsible during outbreaks in relatively closed populations, such as in a school or barrack. Coronavirsues cause some outbreaks, and infections caused by influenza, parainfluenza, and respiratory syncytial viruses may also manifest as common colds, particularly in adults who are experiencing reinfection. Adenoviruses most often lead to pharyngitis but may produce symptoms difficult to distinguish from other respiratory viruses."

> "Rhinoviral infections are rare during winter months, particularly when influenza or respiratory syncytial viruses appear. The seasonality may relate at least partly to changing patterns of social behavior and effects of climate on viral ecology and host factors, including inhibitory substances (eg, interferon) in respiratory secretions. Rhinoviruses are spread by person-to-person contact via contaminated secretions on fingers and by aerosols."

Under the topic of "Respiratory Viral Diseases" in Section 13 (Infectious Diseases), Chapter 162 (Viral Diseases), of Beers, et al., 1999, op. cit., an entire copy of which is incorporated herein by reference, it states the following under the title of "Influenza":

> 'Influenza (or "flu") is commonly and incorrectly used by laymen and some health professionals to refer to respiratory infections that are not caused by influenza virus. Influenza viruses, which are orthomyxoviruses, are classified as types A, B, or C by complement-fixing antibodies to the nucleoprotein and matrix proteins.'

Under the topic of "Respiratory Viral Diseases" in Section 13 (Infectious Diseases), Chapter 162 (Viral Diseases), of Beers, et al., 1999, op. cit., an entire copy of which is incorporated herein by reference, it states the following under the title of "Parainfluenza Viruses" it states the following:

> "The parainfluenza viruses are paramyxoviruses types 1, 2, 3, and 4. The types are similar structurally and biologically, but they tend to cause diseases of different severity, even through they share common antigens as evidenced by cross-reactive antibody responses. Type 4 has antigenic cross-reactivity with mumps."

Please refer to the document entitled "Common Infections" from the web site for the "Community Outreach Health Information Service" or "COHIS" (http://www.cohis.org) that was printed out on Apr. 30, 2002, "COHIS, 2002", an entire copy of which is incorporated herein by reference. COHIS, 2002 lists various viruses causing respiratory viral infections.

For the purpose of this section, all viruses listed herein shall be defined as "viruses causing respiratory infections". It is evident from the above how the invention may be used to treat, cure or prevent diseases caused by those viruses causing respiratory infections. Those detailed descriptions will not be repeated here solely in the interests of brevity.

Therefore, the following statements may be made in the following.

Vapors from the 50% *Eucalyptus globulus* and 50% *Melaleuca alternifolia* mixture of essential oils are broadly antipathogenc. Those vapors are effective against many of the pathogens on the above defined list. In particular, they are effective against many viruses causing respiratory infections.

In accordance with the previous disclosure in the invention, the following general statements may be made.

In accordance with the invention, the inhalation of the vapor from 50% *Eucalyptus globulus* and 50% *Melaleuca alternifolia* can be used to prevent infection of the lungs of patients by Influenza A.

In accordance with the invention, the inhalation of the vapor from 50% *Eucalyptus globulus* and 50% *Melaleuca alternifolia* can be used to prevent the initial infection by viruses causing respiratory infections.

In accordance with the invention, the inhalation of the vapor from 50% *Eucalyptus globulus* and 50% *Melaleuca alternifolia* can be used to cure lungs infected with Influenza A.

In accordance with the invention, the inhalation of the vapor from 50% *Eucalyptus globulus* and 50% *Melaleuca alternifolia* can be used to cure respiratory infections caused by viruses.

In accordance with the invention, the inhalation of the vapor from 50% *Eucalyptus globulus* and 50% *Melaleuca alternifolia* can be used to treat the infection of the lungs by Influenza A.

In accordance with the invention, the inhalation of the vapor from 50% *Eucalyptus globulus* and 50% *Melaleuca alternifolia* can be used to treat the infection of lungs by viruses causing respiratory infections.

In accordance with the invention, the inhalation of the vapor from any mixture of *Eucalyptus globulus* and *Melaleuca alternifolia* can be used to prevent infection of the lungs of patients by Influenza A.

In accordance with the invention, the inhalation of the vapor any mixture of *Eucalyptus globulus* and *Melaleuca alternifolia* can be used to prevent the initial infection by viruses causing respiratory infections.

In accordance with the invention, the inhalation of the vapor from any mixture of *Eucalyptus globulus* and *Melaleuca alternifolia* can be used to cure lungs infected with Influenza A.

In accordance with the invention, the inhalation of the vapor from any mixture of *Eucalyptus globulus* and *Melaleuca alternifolia* can be used to cure respiratory infections caused by viruses.

In accordance with the invention, the inhalation of the vapor from any mixture of *Eucalyptus globulus* and *Melaleuca alternifolia* can be used to treat the infection of the lungs by Influenza A.

In accordance with the invention, the inhalation of the vapor from any mixture of *Eucalyptus globulus* and *Melaleuca alternifolia* can be used to treat the infection of lungs by viruses causing respiratory infections.

Similar statements to the above 12 statements are hereby made by reference with regards to any of the above listed specific pathogens, for example, rhinoviruses and Influenza B.

The No Sinus Pain™ Personal Lung Inhaler manufactured by Inhalation, Inc. is a preferred embodiment of the invention used to prevent, treat or cure the infection of lungs by viruses causing respiratory infections. The Super Sinus and Lungs™ Personal Lung Inhaler manufactured by Inhalation, Inc. is also another preferred embodiment of the invention used to prevent, treat or cure the infection of lungs by viruses causing respiratory infections.

In accordance with the invention, the antipathogenic properties of vapors from any essential oil listed on the above defined "List of Essential Oils" can be tested in the apparatus defined in the above section entitled "Test Chamber". Those vapors showing antipathogenic properties against the pathogens causing pneumonia can be identified using the apparatus and the procedures described in those two sections. That essential oil may then be provided in one or more of the Inhaler apparatus shown herein. Inhaled vapors from the selected Inhaler apparatus may be used to prevent, treat, or cure infections of viruses that infect the respiratory system.

In accordance with the invention, the antipathogenic properties of vapors from any mixture of essential oil listed on the above defined "List of Essential Oils" can be tested in the apparatus defined in the above section entitled "Test Chamber". Those vapors showing antipathogenic properties against the pathogens causing pneumonia can be identified using the apparatus and the procedures described in those two sections. That essential oil may then be provided in one or more Inhaler apparatus shown herein. Inhaled vapors from a selected Inhaler Apparatus may be used to prevent, treat or cure infections of viruses that infect the respiratory system.

Accordingly, the vapors from Mixture #1, Mixture #2, Mixture #3, Mixture #4, Mixture #5, and Mixture #6 which are defined above, and their respective examples, may be used to prevent, treat, and cure viral infections of the human respiratory system. The effective amounts of vapors are determined by various methods including those described in relation to the Test Chamber. In accordance with the above, the vapors from 100% *Melaleuca alternifolia* may be used in a preferred embodiment of the invention to prevent, treat, and cure viral infections of the human respiratory system.

Reference on Essential Oil Vapors and Respiratory System Pathogens

Before addressing the current literature on Severe Acute Respiratory Syndrome ("SARS"), it is first wise to see what the recent scientific literature has to say about the antipathogenic properties of essential oil vapors.

At the time we invented the Inhalers at Inhalation, Inc., (see the introductory portion of the Description of the Preferred Embodiments) the inventors believed that essential oils in the vapor phase would have antibacterial, antiviral, and antifungal properties. The more recent scientific literature which has appeared after our first patent application Ser. No. 09/542,703 was filed on Apr. 3, 2000 shows that oils in the vapor phase can be effective against at least certain bacteria that attack the human respiratory system.

A relevant publication is entitled "Antibacterial activity of essential oils and their major constituents against respiratory tract pathogens by gaseous contact" having the authors of Shigeharu Inouye, Toshio Takizawa and Hideyo Yamaguchi that was published in the Journal of Antimicrobial Chemotherapy in 2001 (The British Society for Antimicrobial Chemotherapy), Volume 47, pages 565–573, hereinafter Inouye, et al., 2001, an entire copy of which is incorporated herein by reference. An complete copy is also available on the internet accessible through Medline.

This publication states in part the following: "The antibacterial activity of 14 essential oils and their major constituents in the gaseous state was evaluated against *Haemophilus influenzae, Streptococcus pneumoniae, Streptococcus*

*pyogenes* and *Staphylococcus aureus*. For most essential oils examined, *H. influenzae* was most susceptible, followed by *S. pneumoniae* and *S. pyogenes*, and then *S. aureus*." It further states: "These results indicate that the antibacterial action of essential oils was most effective when at high vapor concentration for a short time."

Inouye, et al., 2001, further states: "Essential oils produced by plants have been traditionally used for respiratory tract infections, and are used nowadays as ethical medicines for colds (1, 2). In the medicinal field, inhalation therapy of essential oils has been used to treat acute and chronic bronchitis and acute sinusitis. Inhalation of vapors of essential oils augmented the output of respiratory tract fluid (3), maintained the ventilation and drainage of the sinuses (4), had an anti-inflammatory effect on the trachea (5) and reduced asthma (6)."

Inouye, et al., 2001, further states: "Essential oils are known to possess antimicrobial activity, which has been evaluated mainly in liquid medium. Systematic evaluation of the vapor activity was first reported by Maruzzella et. al (7, 8) and Kienholz (9) in 1959, using the inverted Petri dish technique. The technique, in which a volatile compound placed in a cup or a paper disc was exposed to the inverted agar medium plate inoculated with test strains at about 5 mm distances, was convenient and has been used by subsequent researchers (10, 11). Under these conditions, the air space was too small to measure the vapor concentration of essential oil. We employed an airtight box of 1 L air capacity for the measurement of vapor activity (12, 13). Although evaluation of cinnamon bark oil against respiratory tract mycoses has been reported (14), there are no reports describing vapor activity of essential oils against major bacterial respiratory tract pathogens."

Inouye, et al., 2001, further states: "In contrast to antibiotics, essential oils are highly volatile at room temperature. We therefore investigated a potential role for these oils as inhalation therapy, and determined the antibacterial activity of a wide variety of them against five pathogens: *Haemophilus influenzae*, penicillin-susceptible and -resistant *Streptococcus pneumoniae*, *Streptococcus pyogenes* and *Staphylococcus aureus*, by gaseous contact in an airtight box. *Escherichia coli* was used as a control."

Inouye, et al., 2001, further states: "Summarizing these results, we conclude that the antimicrobial action of essential oils by gaseous contact is most efficient when exposed at high vapor concentration for a short time."

Of course, preferred embodiments of the inhalers described herein provide a high vapor concentration that is provided to the respiratory system in a short length of time.

In Table II, Inouye, et al., 2001, shows that Tea Tree Oil is generally effective against the five listed test pathogens, and so is Eucalyptus radiata in higher "MID" doses, where "MID" is defined as the "minimal inhibitory dose" in the paper.

Relevant references are as follows, which are quoted from Inouye, et. al. (2001):

"1. Federspil, P., Wulkow, R. & Zimmermann, T. (1997). Effect of standardized Myrtol in therapy of acute sinusitis—Results of a double-blind, randomized multicenter study compared with placebos. *Laryngo-Rhino-Otologie* 76, 23–7."

"2. von Schindl, R. (1972). Inhalative Wirkung aetherischer Oele. *Weiner Medizinische Wochenschrift* 122, 591–3."

"3. Boyd, E. M. & Sheppard, E. P. (1970). Nutmeg oil and camphene as inhaled expectorants. *Archives of otolaryngology* 92, 372–8."

"4. Burrow, A., Eccles, R. & Jones, A. S. (1983). The effects of camphor, eucalyptus and menthol vapors on nasal resistance to airflow and nasal sensation. *Acta Otolaryngologica* 96, 157–61."

"5. Shubina, L. P., Siurin, S. A. & Savchenko, V. M. (1990). Inhalation of essential oils in the combined treatment of patients with chronic bronchitis. *Vrachebnoe Delo* (Kiev) Part 5, 66–7."

"6. Frohlich, E. (1968) Lavender oil; review of clinical, pharmacological and bacteriological studies. Contribution to clarification of the mechanism of action. *Wiener Medizinische Wochenschrift* 118, 345–50."

"7. Maruzzella, J. C., Balter, J. & Katz, A. (1959). The action of perfume-oil vapours on fungi. *American Perfumer and Aromatics* 74, 21–2."

"8. Maruzzella, J. C. & Sicurella, N. A. (1960). Antibacterial activity of essential oil vapors. *Journal of the American Pharmaceutical Association, Scientific Edition* 49, 692–4.

"9. Kienholz, M. (1959). Studies on the antibacterial action of ethereal oils. *Arzneimittel-Forschung/Drug Research* 9, 519–21."

"10. Pandey, D. K., Tripathi, N. N., Tripathi, R. D. & Dixit, S. N. (1982). Fungitoxic and phytotoxic properties of the essential oil of *Hyptis suaveolens*, *Journal of Plant Diseases and Protection* 89, 344–9."

"11. Gocho, S. (1991) Antibacterial action of aroma compounds in vapor state. *Journal of Antibacterial and Antifungal Agents* 19, 329–34."

"12. Inouye, S., Goi, H., Miyauchi, K., Muraki, S. Ogihara, M. & Iwanamia, Y. (1983). Inhibitory effect of volatile constituents of plants on the proliferation of bacteria. *Journal of Antibacterial and Antifungal Agents* 11, 609–15."

"13. Goi, H., Inouye, S. & Iwanami, Y. (1985). Antifungal activity of powdery black mustard, powdery Wasabi (Japanese horseradish) and allyl isothioacyanate by gaseous contact. *Journal of Antibacterial and Antifungal Agents* 13, 199–204."

"14. Singh, H. B., Srivastava, M. Singh, A. B. & Srivastava, A. K. (1995) Cinnamon bark oil, a potent fungitoxicant against fungi causing respiratory tract mycoses. *Allergy* 50, 995–9."

Entire copies of the above cited 14 references are incorporated herein by reference in their entirety.

Inouye, et al., 2001, states in part with respect to their paper: " . . . , there are no reports describing vapor activity of essential oils agaisnt major bacterial respiratory tact pathogens." Again, Inouye, et al. was published after the filing date of Apr. 3, 2000 for Ser. No. 09/542,703.

Inouye, et al., 2001, does not describe any results about the effects of essential oil vapors on viruses or fungi.

SEVERE ACUTE RESPIRATORY SYNDROMA (SARS)

The World Health Organization ("WHO") recently issued a health alert concerning the infectious disease called "Severe Acute Respiratory Syndrome ("SARS"). See the article in the Seattle Times entitled "Worldwide alert issued over mystery illness", Sunday, Mar. 16, 2003, pages 1 and 18, an entire copy of which is incorporated herein by reference. In view of the above inventions cited in pending U.S. Patent Applications, U.S. Provisional Patent Applications, and in a related U.S. Disclosure Document, the inventors claim the use of the inhalers to prevent, treat, and cure SARS. In particular, the inventors claim the use of their No Colds, No Flus™ Lung Personal Inhaler (containing

*Eucalyptus globulus*), their No Sinus Pain™ Personal Lung Inhaler (containing *Eucalyptus globulus,* and *Melaleuca alternifolia*), their Super Sinus and Lungs™ Personal Lung Inhaler (containing *Eucalyptus globulus, Eucalyptus citriodora,* and *Melaleuca alternifolial*), and their Wild Radiata" Personal Lung Inhaler (containing *Eucalyptus radiata*) to prevent, treat, and cure infections causing SARS. Each of these inhalers possess oils having wide spectrum antibacterial, antiviral, and antifungal properties. So, no matter what causes SARS, there very good reason to conclude that these broadly antisepctic inhalers will be useful to prevent, treat, or cure infections of SARS.

One possible cause of SARS has been recently tentatively identified. See the article in The Seattle Times entitled "Doctors may have found clue to mystery illness", Wednesday, Mar. 19, 2003, page A5, an entire copy of which is incorporated herein by reference. This article states in part: "Specialists at the Institute for Medical Virology at Frankfurt University in Germany said samples from two people there resemble a paramyxovirus, the family of microbes that causes measles, mumps and canine distemper. There is no treatment for that virus group." The article further states: "The paramyxovirus family includes hundreds of different viruses of varying degrees of danger to people. Besides measles and mumps, there is respiratory syncytial virus'a common cause of croup in children, and parainfluenza viruses, which are not influenza, but cause flulike symptoms." In various preferred embodiments, inhaled essential oil vapors from the above "List of Essential Oils" are used to prevent, treat, and cure SARS.

Another more likely cause of SARS has more recently been identified. See the article in The Seattle Times entitled "New findings link mystery illness to mutant cold virus", Tuesday, Mar. 25, 2003, front page and page A14, an entire copy of which is incorporated herein by reference. This article states in part: "A mutated killer cousin of the common cold may be behind the mysterious respiratory disease that has spread quickly around the world and killed 17 people, U.S. public-health officials said yesterday." The article further states: "Different types of viral tests indicate that the new disease—called Severe Acute Respiratory Syndrome, or SARS—is a never-before-seen member of the coronavirus family, the Centers for Disease Control and Prevention announced." The article further states: "There is no known cure for coronaviruses, believed to be responsible for about half of all common colds and so named because their shape resembles a crown." The article further states: "There are three known families of coronaviruses. Limited genetic analysis suggests that the newly discovered one belongs to a fourth family, Dr. Julie Gerberding, director of the CDC." The article yet further states: "The surprising development contradicts the leading theory of international health experts, who believed SARS was related to mumps and measles." The article further states: "Nine of 11 laboratories working around the world to identify the cause of the new disease have found evidence of a paramyxovirus, said David Heymann, director of the World Health Organization's communicable-diseases program." The article further states: "CDC scientists, however, think a coronavirus is a likely candidate because they have isolated it from tissues from lungs and kidneys—the organs that are most severely damaged by SARS. CDC researchers have also found that patients they have tested have no antibodies to the virus in the early stages of the disease but do have them later. That is strong evidence that the coronavirus is playing a major role in the infection." The article further states: "SARS, spread by droplets from sneezes, has spread in six weeks from a rural Chinese province to key cities in Asia to around the world. As of yesterday, 458 people were infected—including 39 Americans in 18 states—Gerberding said." The article further states: "No drugs are known to work against the coronaviruses. But the CDC is working with the Defense Department to test existing antiviral agents to determine if any kill the virus, and to develop tests for the virus." Similar comments also appeared in the article entitled "Deadly illness linked to cold virus" that appeared in The Herald, Tuesday, Mar. 25, 2003, page A4, an entire copy of which is incorporated herein by reference.

The Inhalers identified above called the No Colds, No Flus™ Personal Lung Inhaler, the No Sinus Pain™ Personal Lung Inhaler, the Super Sinus and Lung™ Personal Lung Inhaler, and the Wild Radiata™ Personal Lung Inhaler possess oils that are effective against certain members of the coronavirus family of viruses. Accordingly, a preferred embodiment of this invention is the method of a human inhaling vapors from the No Colds, No Flus™ Lung Personal Inhaler possessing 100% *Eucalyptus globulus* to prevent, treat, and cure infections of SARS. Accordingly, another preferred embodiment of the invention is the method of a human inhaling vapors from the No Sinus Pain™ Personal Lung Inhaler possessing 50% *Eucalyptus globulus* and 50% *Melaleuca alternifolia* to prevent, treat, and cure infections of SARS. Accordingly, yet another preferred embodiment of the invention is the method of a human inhaling vapors from the Super Sinus and Lungs™ Personal Lung Inhaler containing 33⅓% *Eucalyptus globulus,* 33⅓% *Eucalyptus citriodora*, and 33⅓% *Melaleuca alternifolia* to prevent, treat, and cure infections of SARS. Accordingly, and yet further, a preferred embodiment of this invention is the method of a human inhaling vapors from the Wild Radiata™ Personal Lung Inhaler containing 100% *Eucalyptus radiata* to prevent, treat, and cure infections of SARS.

This invention is important. For example, please refer to the article entitled "Mystery illness to keep hospital workers off job" that appeared in The Seattle Times, on Friday, Mar. 21, 2003 on page A20, an entire copy of which is incorporated herein. That article states: "As many as 15 workers at an Albuquerque hospital have been given two days off work to avoid the possible spread of a mysterious respiratory disease brought in by a patient, officials said yesterday." So, even medical workers are fearing this disease.

The SARS infection seems to be getting worse. For example, pease refer to the article entitled "More sick with mystery Asian illness" in The Herald, Sunday, Mar. 23, 2003, page A10, an entire copy of which is incorporated herein by reference. That article states in part: "The federal government increased to 22 the number of people in America suspected of having the mysterious flu-like illness that has sickened hundreds in Asia." The article further states: "The CDC has handed out 35,000 fliers warning of the illness to travelers returning from Asia. This week, U.S. health officials intercepted five planes or boats with sick passengers." The article further states: "Ill passengers were isolated and taken to health care facilities. The other passengers were required to give officials information of their whereabouts for the next two weeks so they can be notified if needed, said Dr. Marty Cetron, a CDC quarantine expert."

The new virus appears to be dramatically affecting airline travel. Please see the article entitled "Travelers, industry are feeling war's baggage" with the subtitle of "Bookings are declining, destinations changing" and "Outbreak of new illness also spurring caution", The Seattle Times, Mar. 25, 2003, page A9, an entire copy of which is incorporated herein by reference. This article states in part: "The U.S.

State Department, on the other hand, warned Americans yesterday to avoid nonessential travel to Vietnam, mainly because some hospitals there are quarantined or closed because of the SARS outbreak and airlines won't accept people who have symptoms of the illness on flights." The article further states: "Singapore authorities also were aggressively trying to contain the disease, quarantining in their homes about 740 residents who had been in contact with people suffering from the illness."

Please refer to the article entitled "Masks in demand" in The Seattle Times, Apr. 3, 2003, on page A17 that states the following: "Most of the masks don't fit well, so airborne pathogens can creep through the sides." "Masks come in different styles and shapes. According to the U.S. Centers for Disease Control and Prevention, the most effective is an N95 model, which filters out 95 percent of tiny particles."

Please refer to the article entitled "SARS outbreak already causes business struggles" that appeared in The Seattle Times, Apr. 3, 2003, on pages C-1 and C-2. That article states in part: "'The outbreak of SARS is significant enough to affect growth across the region," said Merrill Lynch economist T. J. Bond.'

On Apr. 4, 2003, Reuters published an article entitled "China: SARS May Be Linked to Chlamydia-Like Agent", an entire copy of which is incorporated herein by reference. This article states in part: "China's center for disease control said on Friday it suspects a *chlamydia like agent caused an outbreak of a flue-like virus that has killed* 82 people and infected over 2,400 worldwide." This article further states: "'We're 80% sure,", Hong Tao, a researcher with the Institute of virology under the Chinese Center for Disease Control and Prevention, told a news conference.'" This article further states: 'In Geneva, a spokesman for the World Health Organization said the U.N. agency was "99 percent" certain SARS was caused by a previously unknown strain belonging to the coronavirus family, a major cause of the common cold.'

Please refer to the article entitled "SARS quarantines approved" that appeared in the Herald on Apr. 5, 2003, on page A4, that is attributed to The Associated Press. That article states: "President Bush Friday gave federal health officials authority to quarantine Americans sick with the highly contagious mystery illness SARS. Officials said there were no immediate plans to use the emergency powers." This Apr. 5, 2003 article further states: "'It's the first time a new disease has been added to the list in two decades.'" "'If spread in the population," the order says, SARS "would have severe public health consequences."' This Apr. 5, 2003 article further states: "A number of diseases have long been on the list for which quarantine may be used: cholera, diphtheria, infectious tuberculosis, plague, smallpox, yellow fever and several viral hemorrhagic fevers." This Apr. 5, 2003 article further states: "The last large-scale quarantine in this country was during the Spanish flu pandemic of 1918–1919, though there have been small-scale quarantines—for instance, travelers coming off airlines or cruise ships, who have been exposed to curable diseases."

Please refer to the article entitled "Spread of SARS is seen as likely" that appeared in The Seattle Times on Apr. 6, 2003, on page A15, that is attributed to Mr. Daniel Q. Haney of The Associated Press and which also states "Information from The New York Times is included in this report." This article begins with the introduction stating: "dOMINOUS SIGNS are the steep climb in cases, particularly in Hong Kong, and, while many are infected through face-to-face contact, the virus also may spread through the air or be picked up from contaminated surfaces."

This Apr. 6, 2003 article further states: "Can severe acute respiratory syndrome be stopped? As hard as public-health officials work to stamp out the virus, many experts reluctantly conclude it is likely if not inevitable that it eventually will spread everywhere. That Apr. 6, 2003 article further states: "The highly contagious disease has already sickened more than 2,000 people, and at least 90 have died. New cases appear daily in Hong Kong, despite an all-out effort to isolate victims and quarantine those at risk. That Apr. 6, 2003 article further states: "Experts acknowledge that the eventual coarse of any new disease is almost impossible to predict. Some frightening new infections have burned themselves out, while others, like AIDS, have become global disasters.

That Apr. 6, 2003 article further states: "'Will it explode into a major epidemic that will propagate over the years? Or will it fizzle out or be contained at a low rate? That's unknown," said Dr. Lee Harrison of the University of Pittsburgh. "I suspect we will see this disease for at least the next several years. It's hard to imagine it will be over soon.'"

That Apr. 6, 2003 article further states: "Perhaps the most ominous sign is the steep climb in the new cases, especially in Hong Kong, which has had a nearly fourfold increase in just two weeks. Each person who gets it may spread the infection to several others before he even knows he has it." That Apr. 6, 2003 article further states: "While many are infected through face-to-face contact, evidence is mounting that the virus also may spread through the air or be picked up from contaminated surfaces."

That Apr. 6, 2003 article further states: "'A 3.5 percent death rate in the current era, that's notable," said Dr. William Schaffner, director of the infectious-diseases division at Vanderbilt University.'" "'This is a new respiratory illness, undefined, and it has, under certain circumstances, a propensity to spread rapidly, and it had an immediate international component in terms of spread. In that sense it has overtones of new influenza outbreaks that have similar kinds of characteristics, and there it's pretty high up on the urgency list.'"

That Apr. 6, 2003 article further states: "On Friday, President Bush gave federal health officials the power to quarantine Americans sick with SARS, although there is no plan to use that power now. There are more than 100 suspected cases in the United States, but no one has died."

That Apr. 6, 2003 article further states: "'Most people are hesitant to say it will just go away," said Dr. Ruth Berkelman, head of Emory University's Center for Public Health Preparedness and Research. "Too many people are infected to think we won't see it for a long time to come.'"

That Apr. 6, 2003 article further states: "Besides quarantining the sick, health officials have tried to minimize SARS' spread by urging people with suspicious symptoms not to fly on airlines."

That Apr. 6, 2003 article further states: "Officials from the World Health Organization (WHO) visiting the southern Chinese province of Guangzhou, where the epidemic began, said yesterday that the key to controlling the fast-spreading illness could lie in identifying highly infectious people." 'A WHO team is investigating "the phenomenon of 'super spreaders'—people who seem to spread their disease to a lot of other people," said the WHO team leader, Dr. Robert Breiman.' 'Figuring out why they are so infectious "may lead to public-health approaches that will be very effective for control," he said.'

That Apr. 6, 2003 article further states: "However, some experts worry that those who are clearly sick may not be the biggest concern. People catch bad colds from friends who have mild ones." "And the same may be true for SARS; those who have slight symptoms still could spread the disease. In such a scenario, isolating the sick and quarantining their contacts will not work."

That Apr. 6, 2003 article further states: 'We may be able to slow transmission, but we won't be able to stop it if there are many other cases of milder disease out there," said Dr. Arnold Monto, a University of Michigan epidemiologist.'

That Apr. 6, 2003 article further states: "Although the cause of the outbreak has not been proven beyond doubt, investigators say most evidence points to a previously unknown version of the coronavirus, the bug that causes about a third of all colds. Some who study this family of viruses say that because it spreads through coughs and sneezes, they cannot imagine totally wiping it out now that it has infected so many people." That Apr. 6, 2003 article further states: "Just how it acts in the long run will depend on its genetic makeup and origins. Birds and other animals have their own version of coronavirus, and some of them cause much worse disease than the human type."

That Apr. 6, 2003 article further states: "Researchers say SARS may be a standard human coronavirus that underwent a genetic shift that made it more virulent. Or it may be caused by a coronavirus that moved from animals to people." "Such leaps have happened in the recent past. The hendra virus spread from horses to people in Australia, while the nipah virus went from pigs to humans in Malaysia. However, neither virus then spread from person to person."

That Apr. 6, 2003 article further states: "Whatever happens, the virus is likely to change over time, says Dr. Michael Lai of the University of Southern California, a coronavirus expert. Coronaviruses mutate and swap genes frequently. 'The severe problems we are seeing right now might represent a very small minority of the coronavirus infections," Lai said.'

That Apr. 6, 2003 article further states: 'The World Health Organization is still officially optimistic. "We think it is possible that this disease can be beaten back, that with more effort this doesn't have to get out of hand," said Dick Thompson, a WHO Spokesman.' "Such an outcome is far from definite, cautioned Dr. James Hughes, infectious-disease chief at the CDC." 'He called SARS "an urgent global public-health threat" and added: "I think we had better all keep an open mind here. We've seen it spread very dramatically and very rapidly."'

Please refer to the article entitled "2 airlines cut back flights, citing war, economy, SARS" in The Seattle Times on Apr. 8, 2003, on pages C1 and C2. This article states: "FORT WORTH, Tex.—American Airlines said yesterday it would scrap more flights because of the war in Iraq and the weak economy. Meanwhile, Continental Airlines suspended some flights to Hong Kong because of a drop in traffic caused by fear of a mystery illness."

Please refer to the article entitled "Asian airlines are sick of SARS" that appeared in the Herald, on Apr. 9, 2003 on page C-1, that was written by Bryan Corliss. This article states: "The onset of SARS, or sudden (severe—correction) acute respiratory syndrome, has resulted in dramatic drops in tourism in some parts of Southeast Asia, newspapers report, and that in turn has some airlines looking to delay orders."

Please refer to the article entitled "State adds 8 suspected SARS cases" that appeared in The Seattle Times, on Apr. 12, 2003, on page B2. That article states: "Eight new suspected cases of SARS have been reported in Wash. state, including six in King County—one of those a health worker." "The new reports bring the total to 21 suspected cases for the state since the spread of the severe respiratory disease in the United States became apparent about three weeks ago." That Apr. 12, 2003 article also states: "As of Thursday, Washington state ranked third in the number of cases within the U.S. California was first, with 35; New York was second, with 21."

Please refer to the article entitled "Hospital workers feel effects of SARS" that appeared in The Seattle Times on Apr. 13, 2003, on page A26. That Apr. 13, 2003 article on page A26 states: "Severe acute respiratory syndrome, or SARS, has hit hardest the most involved in fighting it—hospital workers. And hospitals, supposed to be havens during medical emergencies, have often turned out to be fountainheads of contagion."

Please refer to the article entitled "Canadians decode SARS" that appeared in the Herald, on Apr. 14, 2003 on page A5. That article states: "Canadian scientists say they have deciphered the genetic code of the virus that causes a mysterious new respiratory infection that has sparked an international health emergency." This Apr. 14, 2003 article further states: "Researchers at the Michael Smith Genome Sciences Center in British Columbia said they were immediately making the information available on the internet to help scientists around the world use the data to fight the epidemic."

This Apr. 14, 2003 article further states: "'This is a huge step forward in the fight to control the spread of SARS,'", said Caroline Astell, projects leader at the center which usually studies cancer.'" This Apr. 14, 2003 article states: "Since scientists zeroed in on a coronaviurs as the cause of SARS, geneticists have been racing to decode all its genes. The Canadian lab finished first, unraveling the nearly 30,000 chemical components at 4 A.M. Saturday." This Apr. 14, 2003 article further states: "Cracking the genetic code will help determine whether the virus has been hiding in nature, jumped from an animal to humans or resulted from a human coronavirus mutation."

Please refer to the article entitled "SARS study hinges on Chinese records" that appeared in The Seattle Times, Apr. 16, 2003, on page A16 which was written by Edith M. Lederer of The Associated Press. This article states in part: "United Nations—The World Health Organization won't know whether SARS is a global disease that's here to stay until it fully understands what's going on in China where it began, the U.N. agency's top communicable-disease expert said yesterday."

That Apr. 16, 2003 article further states: "'For the present, everything hinges on what we find out in China, as far as our projections," said Dr. David Heymann, WHO's executive director of communicable diseases.' That Apr. 16, 2003 article further states: 'Nonetheless, Heymann said, the government has now raised the SARS issue "to a very high political level as well as heath level."' "'What we are talking about is a new disease," Heyman said. "What's dangerous about this is we don't know its potential."'

That Apr. 16, 2003 article further states: "There are more than 3,200 SARS infections worldwide, the bulk of them in China and Hong Cong. So far, 154 people have died."

That Apr. 16, 2003 article further states: 'Heyman said "the jury is still out" on whether SARS can be contained or whether it will become another permanent infectious disease like tuberculosis or malaria.'

That Apr. 16, 2003 article further states: "Experts need to know whether all cases can be traced back too one case, or whether SARS was introduced into many people from something in nature, perhaps an animal, Heymann said.

They also want to know whether there are infected people without symptoms, and if so, whether they can spread the disease."

That Apr. 16, 2003 article further states: "Asked about prospects for developing drugs or a vaccine to combat SARS, Heymann noted a number of obstacles." "'If it's going to be the private sector that develops the vaccine or drug, they want to make sure that this disease is a permanent resident in humans, because they need a market to recover from their investment in research," he said.' "In addition, he said, antiviral drugs are difficult to develop and most effective in early stages when the virus level is low."

Please refer to the article entitled "SARS virus related to common cold, WHO says" that appeared in The Seattle Times, on Apr. 17, 2003, on page A13, which was written by Mr. Bob Stein of The Washington Post. This article states: "The lung infection that has triggered an international health emergency is unquestionably caused by a previously unknown virus related to germs that cause the common cold, the World Health Organization (WHO) confirmed yesterday." That Apr. 17, 2003 article further states: "Dutch scientists produced the evidence needed to link the microbe, known as a coronavirus, to the disease, severe acute respiratory syndrome (SARS), scientists at the United Nations health agency concluded." That Apr. 17, 2003 article further states: "While researchers have been focusing on the virus as the probable cause of SARS for several weeks, the definitive connection is a crucial milestone in the global health crisis."

That Apr. 17, 2003 article further states: "'We now know with certainty what causes SARS," David Heymann, executive director of the organization's communicable-disease program, said in Geneva, Switzerland. "Now we can move . . . aggressively toward modern intervention strategies, including specific treatments and eventually vaccination.'"

That Apr. 17, 2003 article further states: "It will also help scientists trace the evolution of the virus and could help them determine whether it jumped from animals to humans, and if so, from which animals. Tests are under way in pigs and poultry to see how susceptible those animals are to SARS." That Apr. 17, 2003 article further states: "Heymann, meanwhile, said that while the primary route of SARS transmission is through droplets that infected people spray out when they sneeze or cough, scientists had detected evidence of the virus in feces and urine." That Apr. 17, 2003 article further states: "While several tests have been developed for the virus, none is precise enough to answer key questions, such as whether people can spread the virus before and after their symptoms begin and end."

That Apr. 17, 2003 article further states: "The microbe's genes don't appear similar to any other known coronavirus, suggesting it has been hiding in nature in southern China, perhaps in an animal, said Masato Tashira, of the National Institute of Infectious Diseases in Tokyo. There were only two previously known human coronaviruses—so-called because of their distinctive crown-like shell—and they cause about one-third of all colds." That Apr. 17, 2003 article further states: "The conclusion came after researchers in the Netherlands produced two final pieces of evidence: Monkeys infected with the virus developed a disease identical to that in humans, and scientists were able to then find the virus in the animals."

That Apr. 17, 2003 article further states: "'We can with all confidence say the causative agent of SARS is the coronavirus," said Albert Osterhaus, of the Erasmus Medical Center in Rotterdam, who led the research.'

That Apr. 17, 2003 article further states: "Researchers at the University of Hong Kong were the first to isolate the virus. Scientists at the U.S. Centers for Disease Control and Prevention (CDC) in Atlanta quickly confirmed the microbe was a coronavirus. Other laboratories soon found evidence of the same virus in more patients." That Apr. 17, 2003 article further states: "But some scientists also found signs of another virus known as a paramyxovirus, and Chinese scientists said they had evidence another organism, known a *chlamydia,* might be involved."

That Apr. 17, 2003 article further states: "The WHO network started building the case for the coronavirus. For a virus to be conclusively linked to a disease, it must satisfy four criteria, known as Koch's Postulates: The microbe must be found in all patients with the disease; it must be isolated from a patient and grown in the laboratory; it must reproduce the disease in an animal; and it must be found in that animal." That Apr. 17, 2003 article further states: "The Dutch research satisfied the final two criteria, showing that monkeys infected with the coronavius developed the disease, those infected with the paramyxovirus did not and those infected with both did not get sicker than if they were infected with the coronavirus alone."

Please refer to the article entitled "In Hong Kong, a tower of infection" that appeared in The Seattle Times on Apr. 18, 2003 on page A2, written by Mr. Rob Stein of The Washington Post. That article states in part: "The SARS virus that infected hundreds of people in a 33-story Hong Kong apartment building probably spread in part by traveling through bathroom drainpipes, officials said yesterday. That Apr. 18, 2003 article further states: "The possible explanation for what has been one of the most baffling and worrisome outbreaks in the epidemic indicates the virus can be transmitted in ways other than person-to-person contact."

That Apr. 18, 2003 article further states: "'The possibility that the virus could by aerosol move thorough a vertical pipe through other pipes . . . into the air and effect so many people, that's not comforting," said Klaus Stohr, who is leading the World Health Organization's (WHO) efforts against SARS, or severe acute respiratory syndrome.'" "Nevertheless, evidence of the virus has been found in almost every bodily fluid that has been tested, including blood, feces, urine, saliva and tears, Stohr said." "Moreover, other members of the coronavirus family can be rugged, surviving at freezing temperatures for up to a year, in direct sunlight for 10 hours and at room temperature for two weeks, Stohr said."

The Apr. 18, 2003 article further states: "The SARS virus appears to spread primarily in droplets expelled when an infected person sneezes or coughs. But when 321 people became infected in the Block E building in the Amory Gardens apartment complex in Hong Kong, health authorities said that kind of transmission could not account for it. The outbreak prompted officials to evacuate the building and quarantine its residents in camps."

The Apr. 18, 2003 article further states: "'Interviews with Amory Gardens residents revealed frequent complaints bout foul smells in the bathrooms," Eng-kiong said. One test showed air spewed from a drain when an exhaust fan was on.' "'When the bathroom was in use, with the door closed and the exhaust fan switched on, there could be negative pressure to extract contaminated droplets into the bathroom," he said. "Contaminated droplets could then have been deposited on various surfaces such as floor mats, towels, toiletries and other bathroom equipment.'"

The Apr. 18, 2003 article further stats: 'No infected rodents were found, but the building was infested with cockroaches. "Coronavirus was also detected in the pest droppings and in some instances on the surfaces of the cockroaches," indicating the insects could have carried virus around the building, he said.' 'Eng-kiong stressed "there is no evidence to suggest that the disease is transmitted by the waterborne route or by infected dust aerosols," or by virus hanging in the air.' '"So there is a whole series of methods of infection. One is thorough the sewage—through droplets—the second is through person-to-person contacts, and the third is through environmental contamination."'

Please refer to the article entitled "SARS alters business contacts" in The Seattle Times, on Apr. 18, 2003, on page C3. Therein it states: "It sounds extreme, but in the new post-SARS world, global companies such as CenDyne, one of the world's largest producers of CD burners, aren't taking any chances. With the death toll mounting by the day in places as far as Hanoi, Hong Kong, and Toronto, executives are willing to try almost anything to keep their companies on track without endangering themselves or their employees." "'I think the expectation that (globalization) would be a smooth, direct process no longer holds true," said Daniel Yergin, chairman of Cambridge Energy Research Associates and producer of television series on globalization that will air on PBS next month.

This Apr. 18, 2003 article on page C3 further states: 'Over the weekend, the World Health Organization" issued a warning that SARS could become the "first severe new disease of the 21st century with global epidemic potential."'

This Apr. 18, 2003 article on page C3 further states: "The Chinese government has been criticized for not fully disclosing the extent of the illness. U.S. companies are watching anxiously for signs that the virus has migrated to the factories in China that are leading suppliers of apparel, toys, footwear and light electronics." "The Pearl River Delta has been a fertile breeding ground for diseases because of the crowded conditions, the close proximity of farms and cities and a huge migrant work force. It was in the city of Foshan that the first known case of SARS was reported in November."

This Apr. 18, 2003 article on page C3 further states: "Suddenly, getting on an airplane began to feel more like taking a turn at the roulette wheel." "'It's not just your life," said Meadows, a veteran traveler. "It's all the people around you. It's your wife, your daughter, the people who you like at work. It's the people you meet at the Starbucks.'"

Please refer to the article in The Seattle Times entitled "The SARS Prognosis", Apr. 22, 2003, page A3. That Apr. 22, 2003 article states: "Despite an unparalleled global counterattack, severe acute respiratory syndrome (SARS) may be with humanity indefinitely, some infectious-disease experts say." That Apr. 22, 2003 article also states: "A scientific consensus appears to have emerged that the window for completely stamping out the dangerous new lung infection has probably closed because the SARS virus has become entrenched in many places." That Apr. 22, 2003 article further states: "To contain any disease transmitted through the respiratory system is difficult. So, it might have been impossible under any circumstances to contain SARS in China. But any chance of squelching the nascent epidemic was lost because the Chinese government concealed the disease for so many months, experts said."

That Apr. 22, 2003 article further states: "SARS circumnavigated the globe rapidly because it is the first dangerous new disease in decades other than AIDS that can be transmitted person to person—most commonly through droplets sprayed out by a sneeze or a cough. In addition, intercontinental air travel enabled infected people to transport the virus internationally in record time." That Apr. 22, 2003 article further states: '"We can't control tuberculosis in the world. And that is clearly a disease that doesn't look to be as easily transmissible as this, "Osterholn said.'" The Apr. 22, 2003 article attributes this quote to Michael Osterholm, director of the University of Minnesota's Center for Infectious Disease Research and Policy.

Please refer to the article entitled "Work on SARS treatment continues in labs", "Scientists frantically test existing antiviral drugs—U.S. drops ribavirin trials" by The Associated Press, on Wednesday, Apr. 23, 2003, that appeared on the web site of www.journalnow.com. That Apr. 23, 2003 article states: "Scientists in search of a SARS cure have narrowed their focus to several dozen drugs that appear to have the best chance of stopping the deadly respiratory virus, but they have abandoned plans to test one of them in people."

That Apr. 23, 2003 article further states: "The urgent hunt for something that works—preferably a medicine already on the market or close to it—was helped by the breakthrough a week ago in decoding the virus' genetic makeup, which gives scientists some logical targets." That Apr. 23, 2003 article further states: "Although they cannot predict when they will find a treatment, they should know soon if an effective medicine is likely to be in hospitals quickly. If none in testing shows promise in the next few weeks, a treatment may have to be created from scratch, a process that could take at least five years." That Apr. 23, 2003 article further states: "For now, SARS treatment amounts to keeping patients isolated and dealing with their symptoms as the infection runs its course."

That Apr. 23, 2003 article further states: "The drug ribavirin is being used by doctors in Hong Kong and Toronto who are convinced that it helps many SARS patients. But U.S. researchers, who have been skeptical all along, shelved a plan to formally test the drug with a careful experiment in people." That Apr. 23, 2003 article further states: "The decision was made this week after testing at the U.S. Army Medical Research Institute for Infectious Diseases at Fort Detrick, Md., found no evidence that the drug has any effect against the SARS virus growing in tissue cultures." That Apr. 23, 2003 article further states: 'Dr. Catherine Laughlin, the virology chief at the National Institute of Allergy and Infectious Diseases, said that there is no evidence that it worked. "It has significant toxicity, and there was a real chance you could do more harm than good."

That Apr. 23, 2003 article further states: "Viruses are much harder to kill than bacteria, and only 36 antiviral medicines are on the market in the United States. None is specifically aimed at the coronaviruses, the family that includes the SARS virus as well as some that cause common colds." That Apr. 23, 2003 article further states: "Laughlin said that ribavirin is the only drug conclusively shown ineffective in the Army experiments so far, and lab testing is under way or will begin this week on all the other antiviral drugs on the market. These include 16 AIDS drugs, 13 herpes drugs and seven aimed at flu and other viruses. That Apr. 23, 2003 article also states: "Also to be tested are seven forms of interferon, which are the body's natural microbe killers." This Apr. 23, 2003 article further states: '"Certainly there isn't an upfront rational reason to think any of those would work", she (Laughlin) said. "But if any of them did, it would be extremely valuable, because they are available and understood."'

That Apr. 23, 2003 article further states: "The best chance of success may be with about 30 drugs not yet approved but already in testing for other purposes. All are aimed at viral processes similar to those in the coronavirus. These include drugs that may prevent the virus from sticking to human cells or that block some of the steps the virus takes to copy itself." That Apr. 23, 2003 article further states: "Depending on how far along they are in human testing, some of these drugs could be available for SARS fairly quickly. But if none looks promising in Army testing, prospects become more remote. Drug companies have sent in hundreds of others for screening, but it would take years to prove their safety and effectiveness." That Apr. 23, 2003 article further states: "Laughlin said that the government also plans a study of the natural history of the disease in hopes of finding more clues to treatment. Questions include whether lung damage in SARS results from the virus or the body's overly enthusiastic efforts to kill it." That Apr. 23, 2003 article further states: "Some experts worry that it may be too soon to give up on ribavirin. Dr. Michael Lai, a coronavirus expert at the University of Southern California, said that its failure in the test tube does not prove it worthless in people, since the drug might somehow bolster immune defenses."

Please refer to the Apr. 25, 2003 article in The Seattle Times entitled "SARS death rate rises ominously", page A2, which states: "'In Canada, the death rate seems to be very high," said David Brandling-Bennett, deputy director of the Pan American Health Organization in Washington, the WHO's regional office. "One wouldn't expect to see higher death rates in Canada; it may depend on the intensity of the exposure. The more viral particles you get, the more severe the disease."'

That Apr. 25, 2003 article further states: "One thing that worries health officials about SARS is that so far, it seems to be considerably more deadly than influenza, another major respiratory disease. SARS is the first life-threatening new disease to emerge in decades that can be spread directly from one person to another by casual contact." That Apr. 25, 2003 article further states: "Reliable death rates are available for the flu. In a typical year, it is usually below 1 percent. The Spanish flu epidemic of 1918–1919 had a death rate estimated at 2 percent. However, it killed perhaps 25 million people because it quickly swept the globe." That Apr. 25, 2003 article further states: "'What made it such a big killer was that so many people were infected," said Stephen Morse, director of the Center for Public Health Preparedness at the Mailman School of Public Health of Columbia University."'That Apr. 25, 2003 article further states: "SARS' actual mortality rate remains to be seen. It may turn out that there are a large number of people who become infected but never fall ill."

Please refer to the article in The Seattle Times entitled "Scientists warn of multiple SARS strains", Apr. 27, 2003, page A12, which is credited to Mr. Rob Stein of The Washington Post. This article states: "Different strains of the virus that causes severe acute respiratory syndrome, or SARS, may be circulating around the world, which could explain why the disease seems more dangerous in some places than others, scientists say." This article further states: "Researchers have deciphered the genetic makeups of more than 12 samples of SARS virus, and preliminary analyses indicate there is a spectrum of genetic variation." This article further states: "Although it is too early to draw conclusions from those variations—whether any affect how easily the virus spreads, how sick it makes people or how easily the immune system recognizes it—that spectrum could explain why the disease has appeared to be more transmissible and deadly in places such as Hong Kong and Toronto." This article further states: "'Scientifically, it would not be at all surprising," said Robert Webster, a virologist at the St. Jude Children's Medical Center in Memphis, Tenn., who just returned from Hong Kong. "The chances are very good that the virus that got carried into Toronto and Hong Kong were different."' This article further states under the subtitle of "*Prone to mutations*" the following: "If there are different varieties of the virus, they could either be the result of different strains jumping from animals to humans at the same time or of mutations that have occurred since the disease emerged in southern China in November." The article further states: "SARS is caused by a previously unknown version of coronavirus. Coronaviruses are so-called RNA viruses which are especially prone to mutations because their reproductive process has fewer safeguards." This article further states: "'When an RNA virus goes across to a new host, it goes through an explosive burst of evolution," Webster said. Most genetic changes in viruses have little effect on how they behave. But if a mutation occurs in a crucial gene, it can have significant impact.' The article further states: "'It only takes one mutation in the critical area," said Webster, noting just a single change in the genetic makeup of the flu virus can turn it from a relatively mild pathogen into a killer. "I would not be at all surprised if there were variants."' This article further states: 'Klass Strohr, top SARS scientist at the World Health Organization (WHO), said different varieties of the virus could explain the apparent disparities in the disease. "We know a single amino-acid change can lead to a significant change in pathogenicity of the virus," said Stohr, referring to the chemical components of DNA.' The article further states under the substitute of 'Virus is going to evolve' the following: 'Stohr added, however, that viruses often change, especially if they recently moved from an animal to humans. "The virus is gong to evolve. It's going to be subject to selective pressure," Stohr said. "Certain substrains could be favored by this evolution."' The article further states: "In evolutionary terms, it would be to the virus' advantage to be easily spread but not very deadly. That way an infected person would have more time to infect others, keeping the virus alive." The article further states: 'Julie Gerberding, director of the federal Centers for Disease Control and Prevention in Atlanta, said one of the key questions about SARS is why some people seem to be getting sicker in some places more than others. "We have a lot to learn."' The article concludes with: "To try to answer some of these questions, the WHO plans to establish a central repository of genetic information about the SARS virus so methodical analyses can be made, Stohr said."

Various embodiments of the invention contemplate using the vapors from one or more of the essential oils in the "List of Essential Oils" defined above the section heading of "SARS" herein to prevent, treat, or cure infections of a coronavirus that causes SARS. Other embodiments contemplate using the vapors from a mixture in any relative proportion of two of the previously defined essential oils in the "List of Essential Oils" defined above the section heading of "SARS" herein to prevent, treat, or cure infections a coronavirus that causes SARS. Yet other embodiments contemplate using the vapors from a mixture in any relative proportion of two or more of the essential oils in the "List of Essential Oils" defined above the section heading of "SARS" herein to prevent, treat, or cure infections a coronavirus causing SARS. Essential oils within the hand-held Inhalers are used to produce the respective vapors.

As previously stated above, it has been theorized that a paramyxovirus or a coronavirus is responsible for SARS. However, in the previously filed Provisional Patent Applications cited above, the inventor has theorized about different pathogens interacting in an associated, or symbiotic, or mycorrhizal type relationship.

The book entitled "A Dictionary of Biology", Third Edition, Oxford University Press, New York, N.Y., 1996 ("Oxford, 1996"), an entire copy of which is incorporated herein by reference, suitably defines certain of these terms.

Oxford, 1996, defines "association" to be: "An ecological unit in which two or more species occur in closer proximity to one another than would be expected on the basis of chance. Early plant ecologists recognized associations of fixed composition on the basis of the *dominant species present (e.g. a coniferous forest association). Associations now tend to be detected by using more objective statistical sampling methods. See also consociation."

Oxford, 1996, defines "symbiosis" as follows: "An interaction between individuals of different species (symbionts). The term symbiosis is usually restricted to interactions in which both species benefit (cooperation; mutualism), but it may be used for other close associations, such as *commensalism. Many symbioses are obligatory (i.e. the participants cannot survive without the interaction); for example, a lichen is an obligatory symbiotic relationship between an alga or blue-green bacterium and a fungus."

Oxford, 1996, defines "mycorrhiza" as follows: "The mutually beneficial association (see mutualism) formed between fungi and the roots of plants. This is a very common form of mutualism; the absorption of mineral ions by the plant roots is enhanced by the presence of the fungus, which benefits by obtaining soluble organic nutrients from the root cells. Ectotrophic mycorrhizas form a network of hyphae around the root and grow into the air spaces between the cells of the root. The hyphae of endotrophic mycorrhizas are thought to actually enter the cells of the roots."

Oxford, 1996, defines "consociation" as follows: "A climax plant *community that is dominated by one particular species, e.g. a pine forest. See dominant. Compare association."

Oxford, 1996, defines cooperation as follows: "An association between two or more members of the same species (intraspecific cooperation), or between individuals of different species (interspecific cooperation), in which all members benefit. An example of interspecific cooperation is the relationship formed between ants and aphids; the aphids gain protection by living in the ant colonies, while the ants feed on secretions from the aphids. Interspecific cooperation is a looser association than *mutualism.

Oxford, 1996, defines "mutualism" as follows: "An interaction between two species in which both species benefit. (The term *symbiosis is often used synonymously with mutualism.) A well-known example of mutualism is the association between termites and the specialized protozoans that inhabit their guts. The protozoans, unlike the termites, are able to digest the cellulose of the wood that the termites eat and release sugars that the termites absorb. The termites benefit by being able to use wood as a foodstuff, while the protozoans are supplied with food and a suitable environment. See also mycorrhiza."

In view of these definitions, SARS may be caused by an association or symbiotic relationship between a coronavirus and paramyxovirus.

In view of these definitions, SARS may be caused by an association or symbiotic relationship between a coronavirus and a *chlamydia* bacterium.

In view of these definitions, SARS may be caused by an association or symbiotic relationship between a paramyxovirus and a *chlamydia* bacterium.

In view of these definitions, SARS may be caused by an association or symbiotic relationships between any two or more of the following: a coronavirus; a paramyxovirus; and/or a *chlamydia* bacterium.

In view of these definitions, SARS may be caused by an association or symbiotic relationships between any two or more of the following: one or more coronaviruses; one or more paramyxoviruses; and/or one or more types of *chlamydia* bacteria.

As is evident from the above, there are various varieties, or strains, of coronavirus found in humans that causes SARS. Similarly, there are different varieties, or strains, of paramyxovirus that may be associated with the SARS. And further, there are different varieties, or strains, of *chlamydia* bacteria associated with SARS.

Please refer to U.S. patent application Ser. No. 10/269, 891 that has the filing date of Oct. 12, 2002, an entire copy of which is incorporated herein by reference. Ser. No. 10/269,891 was filed before the outbreak of SARS in China that is thought to have begun sometime during November of 2002. Ser. No. 10/269,891 presents a table entitled "List of Pathogens", under the subcategories of "Bacteria", "Viruses", "Fungi", "Algae" and "Parasites" which spans page 68, line 8, to page 76, line 21 of the specification. An entire copy of that "List of Pathogens" in Ser. No. 10/269, 891 is also incorporated herein by reference. *Chlamydia pneumoniae* appears on page 69, line 2, under the subcategory of "Bacteria". Other *Chlamydias* appear on the same page, lines 3 and 4. Coronaviruses appear on page 72, line 22, under the subcategory of "Viruses". Four different types of paramyxoviruses appear on page 73, line 32, to page 74, line 2. The parainfluenza virus appears on page 73, line 30.

In view of these definitions, SARS may be caused by an association ("associated") or by symbiotic relationships between any two or more of the following: a coronavirus; paramyxovirus; a *chlamydia* bacterium; or any other entry in the "List of Pathogens" defined above.

In view of these definitions, SARS may be caused by an association ("associated") or by symbiotic relationships between any two or more of the following: a coronavirus; a paramyxovirus; a *chlamydia* bacterium; or two or more entries in the "List of Pathogens" defined above.

In fact, SARS may be caused by an association or by symbiotic relationships between one or more entries on the above "List of Pathogens".

In fact, SARS may be caused by an association or by symbiotic relationships between two or more entries on the above "List of Pathogens".

As shown in prior patent documents, selected vapors from essential oils possess antibacterial, antiviral, and antifungal properties. Because SARS is caused by a yet to be identified pathogen, or an association of pathogens, one approach to prevent, treat, or cure SARS is to inhale a general "antiseptic agent" that will not harm humans. Unfortunately, alcohols, hydrogen peroxide, and many other antiseptic agents cannot be inhaled safely by humans. Fortunately, essential oil vapors behave like antiseptics, and they have been known to be safe to inhale by humans. For more on this topic, please refer to the following section below section entitled "Advantages of Inhaled Antiseptics".

The Inhalers identified above called the No Colds, No Flus™ Personal Lung Inhaler, the No Sinus Pain™ Personal Lung Inhaler, the Super Sinus and Lung™ Personal Lung Inhaler, and the Wild Radiata™ Personal Lung Inhaler possess oils that are broadly effective against many different pathogens. Accordingly, a preferred embodiment of the invention is the method of a human inhaling vapors from the No Colds, No Flus™ Lung Personal Lung Inhaler possessing 100% *Eucalyptus globulus* to prevent, treat, and cure infections of associated pathogens causing SARS. Accordingly, another preferred embodiment of the invention is the method of a human inhaling vapors from the No Sinus Pain™ Personal Lung Inhaler possessing 50% *Eucalyptus globulus* and 50% *Melaleuca alternifolia* to prevent, treat, and cure infections of associated pathogens causing SARS. Accordingly, yet another preferred embodiment of the invention is the method of a human inhaling vapors from the Super Sinus and Lungs™ Personal Lung Inhaler containing 33⅓% *Eucalyptus globulus,* 33⅓% *Eucalyptus citriodora,* and 33⅓% *Melaleuca alternifolia* to prevent, treat, and cure infections of associated pathogens causing SARS. Accordingly, yet another preferred embodiment of the invention is the method of a human inhaling vapors from the Wild Radiata™ Personal Lung Inhaler containing 100% *Eucalyptus radiata* to prevent, treat, and cure infections of associated pathogens causing SARS.

Another preferred embodiment of the invention is using the essential oils in steam nebulizers to prevent, treat, and cure infections of associated pathogens causing SARS.

Here, for clarity, a pathogen may be a virus, bacteria, fungi. In rarer situations, the term pathogen may refer to a prion, an algae, or a parasite.

The above Inhalers are used to prevent the infection of SARS.

Accordingly, the No Colds, No Flus™ Personal Lung Inhaler is used as a "1st Inhalation Defense™".

The No Sinus Pain™ Personal Lung Inhaler is used as a "2nd Inhalation Defense™".

The Wild Radiata™ Personal Lung Inhaler is used as a "3rd Inhalation Defense™".

The Super Sinus & Lungs™ Personal Lung Inhaler is used as the "4th Inhalation Defense™".

Another preferred embodiment of the invention is the method to select certain ingredients in essential oils that are effective against SARS. This method comprises the following steps:

a. Perform vapors tests in a laboratory to determine which natural essential oil vapors are effective against SARS—for example *Melaleuca alternifolia.* b. If the essential oil vapors tested proves effective against SARS, then try an individual constituent of the oil to determine its effectiveness—for example 1-terpinen-4-ol, a major constituent in *Melaleuca alternifolia.* c. Repeat step B with different individual constituents, or combinations of individual constituents, to determine the mixture of individual components that have maximum effectiveness against SARS. For example, in *Melaleuca alternifolia,* 1,8-cineole can be studied separately or in combination with 1-terpinen-4-ol.

d. After an effective component, or components have been determined, perform tests on humans by placing the components, or components in either: (a) the Inhalers as previously described; or (b) in a nebulizer device.

e. If the results are successful in tests on humans to prevent, treat, or cure infections related to SARS, then use the effective component, or components, to prevent, treat, cure infections related to SARS.

Because of the statistical nature of the word "prevent", several of the above embodiments describe methods to reduce the risks of infection of the human respiratory system by pathogens causing SARS that includes at least the step of the inhalation of concentrated vapors from *eucalyptus* oil immediately before entering an enclosed public area having one or more human beings within the enclosed area. The method of inhaling essential oil vapors that have antiseptic properties will stastically reduce the probability of being infected by the pathogens causing SARS. This is a useful invention that can be used by the public not having access to the expensive protective equipment of the type recommended by the CDC.

Vapors from the 50% *Eucalyptus globulus* and 50% *Melaleuca alternifolia* mixture of essential oils are broadly antipathogenc. Those vapors are effective against many of the pathogens on the above defined List of Pathogens. In particular, they are effective against the pathogens causing Severe Acute Respiratory Syndrome (SARS).

Therefore, the following general statements may be made.

In accordance with the invention, the inhalation of the vapor from 50% *Eucalyptus globulus* and 50% *Melaleuca alternifolia* can be used to prevent infection of coronaviruses within lungs that cause Severe Acute Respiratory Syndrome (SARS).

In accordance with the invention, the inhalation of the vapor from 50% *Eucalyptus globulus* and 50% *Melaleuca alternifolia* can be used to prevent the initial infection by pathogens within lungs that cause Severe Acute Respiratory Syndrome (SARS).

In accordance with the invention, the inhalation of the vapor from 50% *Eucalyptus globulus* and 50% *Melaleuca alternifolia* can be used to cure infections of coronaviruses within lungs that cause Severe Acute Respiratory Syndrome (SARS).

In accordance with the invention, the inhalation of the vapor from 50% *Eucalyptus globulus* and 50% *Melaleuca alternifolia* can be used to cure infections of pathogens within lungs that cause Severe Acute Respiratory Syndrome (SARS).

In accordance with the invention, the inhalation of the vapor from 50% *Eucalyptus globulus* and 50% *Melaleuca alternifolia* can be used to treat infections of coronaviruses within lungs that cause Severe Acute Respiratory Syndrome (SARS).

In accordance with the invention, the inhalation of the vapor from 50% *Eucalyptus globulus* and 50% *Melaleuca alternifolia* can be used to treat the infections of pathogens within lungs that cause Severe Acute Respiratory Syndrome (SARS).

In accordance with the invention, the inhalation of the vapor from any mixture of *Eucalyptus globulus* and *Melaleuca alternifolia* can be used to prevent infection of coronavirsues within lungs that cause Severe Acute Respiratory Syndrome (SARS).

In accordance with the invention, the inhalation of the vapor any mixture of *Eucalyptus globulus* and *Melaleuca alternifolia* can be used to prevent the infection by pathogens in lungs that cause Severe Acute Respiratory Syndrome (SARS).

In accordance with the invention, the inhalation of the vapor from any mixture of *Eucalyptus globulus* and *Melaleuca alternifolia* can be used to cure infections of coronaviruses that cause Severe Acute Respiratory Syndrome (SARS).

In accordance with the invention, the inhalation of the vapor from any mixture of *Eucalyptus globulus* and *Melaleuca alternifolia* can be used to cure infections of pathogens that cause Severe Acute Respiratory Syndrome (SARS).

In accordance with the invention, the inhalation of the vapor from any mixture of *Eucalyptus globulus* and *Melaleuca alternifolia* can be used to treat infections of coronavirsues within the lungs which cause Severe Acute Respiratory Syndrome (SARS).

In accordance with the invention, the inhalation of the vapor from any mixture of *Eucalyptus globulus* and *Melaleuca alternifolia* can be used to treat infections of pathogens within lungs that cause Severe Acute Respiratory Syndrome (SARS).

Accordingly, the No Sinus Pain™ Personal Lung Inhaler manufactured by Inhalation, Inc. is a preferred embodiment of the invention used to prevent, treat, or cure infections of pathogens that cause Severe Acute Respiratory Syndrome (SARS). Another preferred embodiment is the use of the Super Sinus and Lungs™ Personal Lung Inhaler to prevent, treat, and cure the infections of pathogens that cause Sever Acute Respiratory Syndrome (SARS).

In accordance with the invention, the antipathogenic properties of vapors from any essential oil listed on the above defined "List of Essential Oils" can be tested in the above defined Test Chamber. Those vapors showing antipathogenic properties against the pathogens causing Severe Acute Respiratory Syndrome (SARS) can be identified using the Test Chamber and related experimental procedures. That essential oil may then be provided in one or more of the Inhalers as described herein. Inhaled vapors from such Inhaler apparatus may be used to prevent, treat, or cure infections of pathogens causing Sever Acute Respiratory Syndrome (SARS).

In accordance with the invention, the antipathogenic properties of vapors from any mixture of essential oil listed on the above defined "List of Essential Oils" can be tested in the Test Chamber. Those vapors showing antipathogenic properties against the pathogens causing Severe Acute Respiratory Syndrome (SARS) can be identified using that the Test Chamber and related experimental procedures. The essential oil having such antipathogenic properties may then be provided in the Inhalers described herein. Inhaled vapors from that Inhaler apparatus may be used to prevent, treat, or cure infections of the lungs by pathogens causing Severe Acute Respiratory Syndrome (SARS).

Accordingly, the vapors from Mixture #1, Mixture #2, Mixture #3, Mixture #4, Mixture #5, and Mixture #6 which are defined above, and their respective examples, may be used to prevent, treat, and cure infections associated with Severe Acute Respiratory Syndrome (SARS). The effective amounts of vapors are determined by various methods including those described in relation to the Test Chamber. In accordance with the above, the vapors from 100% *Melaleuca alternifolia* may be used in a preferred embodiment of the invention to prevent, treat, and cure infections associated with Severe Acute Respiratory Syndrome (SARS).

The above methods to prevent, treat, and cure infections of the pathogens causing Severe Acute Respiratory Syndrome (SARS) may be done in addition to any other standard therapies that are developed.

Another embodiment of the invention is to use vapors from *Lomatium disectum* to prevent, treat, and cure infections causing SARS.

Advantages of Inhaled Antiseptics to Prevent, Treat and Cure Respiratory Diseases Including SARS Regretfully, there seems to be a fundamental reluctance in the medical community to test natural substances to prevent, treat, and cure human diseases despite the fact that many of our current drugs derive directly from natural substances such as taxol, aspirin, and penicillin—to name just a few. Despite this situation, there are intrinsic advantages to the new method of using inhaled antiseptic vapors, such as vapors from selected essential oils, to prevent, treat, and cure infections causing SARS. These intrinsic advantages are listed as follows:

A. From Ser. No. 09/542,703, and later, from Inouye, et al., 2001, selected essential oil vapors are known to be effective against certain infectious respiratory bacteria.

B. From the literature, liquid essential oils are known to have broad antiseptic properties against a wide variety of viruses, bacteria, and fungi.

C. Selected essential oil vapors are safe to inhale. For example the applicants are not aware of any known deaths cited in the medical literature from inhaling the vapors from *Eucalyptus globulus* ("*Eucalyptus* Oil").

D. Using essential oil vapors as inhaled antiseptics would be effective against combinations of viruses, bacteria and perhaps fungi that could form associated, or symbiotic relationships, resulting in complex infections that might be responsible for SARS.

E. An inhaled antiseptic approach is ideal when the nature of the pathogen is unknown and/or the pathogen mutates rapidly.

F. The essential oil vapors can be provided immediately to humans in the form of simple hand-held inhaler devices (such as those manufactured by Inhalation, Inc. at the web site of www.NoColds-NoFlus.com).

G. Most essential oils are fat soluble. Therefore, these oils permeate the lung tissue.

H. After inhalation, some of the vapors enter the blood stream. These oils are thought to cross the blood-brain boundary and may possibly eradicate pathogens elsewhere in the body.

I. According to the literature, there is little chance for humans overdosing on inhaling essential oil vapors. In about 2 hours after inhalation, the vapors have normally been exhaled back out of the body—primarily from the lungs.

J. Selected essential oils, such as *Eucalyptus* Oil, smell very good to humans, and the patients are therefore likely to repetitively inhale the vapors to suitably prevent, treat, or cure infections from pathogens causing SARS. It is likely necessary to repetitively inhale the essential oil vapors every 2 hours or so to prevent infections caused by a nearby infected individual who may be coughing, sneezing, etc.

K. Infections of pathogens causing SARS may be made more severe in the presence of other infections such as bronchitis, TB, or some other form of pneumonia in the patient. Therefore, a broad antiseptic approach is desirable.

L. If such an inhaled antiseptic approach appeared to "help", it could be implemented immediately giving more time to come up with other therapies, perhaps including immunization therapies.

M. Inhaled antiseptic essential oil vapors have an immediate impact in the lungs, whereas digested pills take relatively longer, and immunization can still take longer periods of time.

N. One of the co-inventors, William Banning Vail III, has been repetitively inhaling essential oil vapors from *Eucalyptus globulus* and *Melaleuca alternifolia* for about 3½ years at this point. He has not had any lung infections during this period, and others have had similar experiences for about 2½ years. See "Our Stories" on the web site of www.NoColds-NoFlus.com. Many M.D.'s and N.D.'s recommend inhaling the vapors from *Eucalyptus globulus* for other reasons, and please see their comments in the "References" on the cited web site.

O. Inhalers having essential oil vapors could at least provide a "first defense" to prevent the infection of pathogens causing SARS. The CDC web site has recently stated that surgical masks do not provide positive protection against either SARS, or against TB. Accordingly, the inhalers containing essential oils should be considered ASAP—particularly if SARS is caused by an airborne pathogen as suggested by some experts.

P. Each natural essential oil has many constituents—which are all well documented in the literature. If the vapors from natural essential oils are found to be effective against SARS, then perhaps the most effective ingredient, or combination of ingredients, can be rapidly isolated.

Q. Mankind has probably used *Eucalyptus* Oil and Tea Tree Oil for a broad range of respiratory conditions for many centuries. Perhaps these oils have additional uses which have yet to be confirmed by medical science. Please consider the history of aspirin as an analogy. There are also many other essential oils which can be considered that are listed in the above "List of Essential Oils".

R. *Eucalyptus* Oil is now used as a major active ingredient in Listerine (R). Tea Tree Oil is now used as the major antipathogenic ingredient in some toothpastes, mouthwashes, and in some shampoos.

S. During the evolutionary history of life on Earth, on Earth, essential oils in plants and trees have been theorized to have co-evolved with viruses, bacteria and fungi to protect the plants and trees from viral, bacterial and fungal infections. Accordingly, it seems wise to test these natural substances ASAP under the circumstances.

Inhalation, Inc.

The inventors have formed Inhalation, Inc. to commercialize their inventions. As of this date, this firm manufactures and provides the following inhalers:

The No Colds, No Flus™ Personal Lung Inhaler that contains 100% *Eucalyptus globulus* ("*Eucalyptus* oil"). This may also be re-labeled to read "1st Inhalation Defense™".

The No Sinus Pain™ Personal Lung Inhaler that contains a mixture of *Eucalyptus globulus* ("*Eucalyptus* oil") and *Melaleuca alternifolia* ("Tea Tree oil"). This may also be re-labeled to read "2nd Inhalation Defense™".

The Wild Radiata™ Personal Lung Inhaler that contains 100% *Eucalyptus radiata* that is wild-picked in Australia. This may also be re-labeled to read "3rd Inhalation Defense™".

The Super Sinus & Lungs™ Personal Lung Inhaler that contains a mixture of *Eucalyptus globulus, Eucalyptus citriodora,* and *Melaleuca alternifolia.* This may also be re-labeled to read "4th Inhalation Defense™".

The No Asthma Attack™ Personal Lung Inhaler that contains *Eucalyptus radiata.*

The No Head Ache™ Personal Inhaler that contains a mixture of *Lavandula hybrida* ("Lavandin"), *Metha piperita* ("Peppermint") and *Betula alleghaniensis* ("Birch").

The No Stress, No Nerves™ Personal Inhaler that contains a mixture of *Lavandula angustifolia* ("Lavender oil") and *Eucalyptus globulus* ("*Eucalyptus* oil")

The Women's Hormone Balance™ Personal Inhaler that contains a mixture of *Citrus aur. bergamia* ("Bergamot"), *Salvia sclarea* ("Clary Sage"), and *Pelargonium roseum* ("Rose Geranium").

The Go To Sleep™ Personal Inhaler that contains a mixture of *Lavandula vera* ("Lavender oil") and *Anthemis nobilis* ("Roman Chamomile").

These Inhalers are a commercial success. They are now sold on the internet and in high-end naturopathic stores. Several physicians are now using these inhalers in their normal practices.

Use of Essential Oils in Nebulizers

There are small personal nebulizers and large nebulizers used in doctors offices and in hospitals. Many of these use a compressor of some size that typically blows air through a container of some variety containing medication. The resulting vapor is inhaled by patients. Other nebulizers use different forms of energy such as ultrasonic transducers.

A preferred embodiment of this invention is the method of using the previously defined essential oils and mixtures of essential oils in nebulizer devices to produce vapors that are inhaled by patients to prevent, treat, and cure human respiratory diseases.

Measurements of Interest

Measurements by an internationally known expert show that it is safe for humans to inhale the vapors from the mixture of 50% *Eucalyptus globulus* and 50% *Melaleuca alternifolia.* Please refer to the Apr. 26, 2002 letter from Dr. Christoph Streicher, Chief Chemist, The Foundation for Aromatherapy Education and Research, which is 27 pages long, an entire copy of which is incorporated herein by reference.

Measurements on the antipathogenic properties of the essential oils used in inhalers manufactured by Inhalation, Inc. were performed by Dr. Richard Honour, Chairman, of Inhalation, Inc. and Chairman of the Eulara Corporation. Please refer to the Sep. 10, 2002 Press Release from Inhalation, Inc., an entire copy of which is incorporated herein by reference. That Press Release states the following in part:

'Seattle-based Eulara Corporation, a plant essential oils company that focuses primarily on skin care products, including antibacterial, antifungal and antiviral applications, recently conducted a series of in vitro anti-microbial tests, which confirm the Vail's claims in the patent applications, as well as those cited in scientific literature.

"Our company has a substantial collection of human pathogenic bacteria which we use in our testing programs," said Eulara chairman Dr. Richard Honour. "We challenged the eucalyptus and tea tree oils used in Inhalation, Inc.'s products against a broad collection of human clinical isolates of *Staphylococcus, Pseudomonas, Mycobacterium, Salmonella, E. Coli* and other bacteria. Our test results showed significant, direct anti-microbial activity against these bacteria." Dr. Honour holds a Ph.D. in Microbiology and Plant Pathology, and can be reached at www.Eulara.com.'

These comments from Dr. Honour were based in part upon the following e-mails sent by Dr. Honour to the first inventor: Jun. 1, 2002 (2 pages); a second e-mail also dated Jun. 1, 2002 (showing a photograph of clearing zones); Jun. 25, 2002 (2 pages); Jun. 26, 2002 (1 pages); and Jul. 15, 2002 (2 pages). Entire copies of each of these e-mails referenced in this paragraph are incorporated herein by reference.

The Jun. 25, 2002 e-mail from Dr. Honour shows that the *Melaleuca alterniflolia* used by Inhalation, Inc. is effective against the following bacteria: *Enterococcus faecium; Bacillus subtilus; Escherichia coli; Salmonella typhimurium; Streptococcus pyogenes; Streptococcus faecium; Streptococcus faecalis; Pseudomonas aeruginosa;* Methicillin-Resistant *Staphylococcus epidermidis; Staphylococcus epidermidis*; and Methicillin-Resistant *Staphylococcus aureus*.

The Jun. 25, 2002 e-mail from Dr. Honour shows that the mixture of 50% *Eucalyptus globulus* with 50% *Melaleuca alternifolia* is effective against most of the above pathogens. This Jun. 25, 2002 e-mail shows that this 50%—50% mix is more effective than 100% *Melaleuca alternifolia* by itself against *Enterococcus faecium, Bacillus subtilus,* and *Staphylococcus aureus*.

The Jun. 25, 2003 e-mail from Dr. Honour shows that pure *Eucalyptus globulus* as used by Inhalation, Inc. is effective against the following bacteria: *Bacillus subtilus; Salmonella typhimurium; Streptococcus pyogenes;* and *Streptococcus faecalis*.

The Jul. 15, 2003 e-mail from Dr. Honour shows that the 100% *Eucalyptus globulus,* the 100% *Melaleuca alternifolia,* and the mixture of 50% *Eucalyptus globulus* and *Melaleuca alternifolia* that are provided by Inhalation, Inc. are all effective against the following mycobacteria: *Mycobacterium smegmatis; Mycobacterium fortuitum;* and *Mycobacterium phlei*.

Unknown Respiratory Pathogens

A very important attribute of the invention is that it may be used as a practical method by individuals to reduce the probability of respiratory infection by unknown, and unpredictable, pathogens, in crowded locations where many other possibly infectious individuals are present.

At the present time of the filing of this application herein, many individuals are wearing low quality surgical masks in Hong Kong in an attempt to reduce the probability of being infected by the pathogen causing SARS. This is despite the fact that the CDC currently advises that these low quality surgical masks are generally ineffective against bacteria causing tuberculosis and against the pathogens causing SARS. Nevertheless, many individuals do wear these masks simply to reduce the probability of being infected.

Further, as of today, the precise pathogen, or pathogens, causing SARS are not known definitively. Despite this fact, certain antiviral drugs are used to treat SARS despite the fact there is absolutely no proof that they are effective, such as ribavirin, as described above in the Apr. 23, 2003 article from The Associated Press. Nevertheless, these drugs are considered useful by the medical profession.

Therefore, despite the fact that low quality surgical masks are used in an attempt to reduce the probability of infection by individuals in public places, and despite the fact that the detailed nature of the pathogen causing SARS is not known, any method that has a reasonable chance of reducing the probability of infection from unknown pathogens, including SARS, is a useful invention for individuals trying to reduce the probability of infection in enclosed public places.

Put in another perspective, individuals are advised to wash their hands to prevent infection of a wide variety of infectious respiratory pathogens. This is true even through it is impossible for individuals in crowded spaces to determine what pathogens might be on their hands. Further, it has not been shown that washing of hands is effective against every known infectious pathogen. Nevertheless, it is suggested that individuals wash their hands in an effort to reduce the probability of infection by respiratory pathogens.

Similarly, hospital personnel are advised to use alcohol wipes on their hands in an effort to reduce the probability of becoming infected themselves, or infecting somebody else, by a range of pathogens. However, this procedure has not been shown to be effective against all known infectious pathogens. Nevertheless, alcohol wipes are advised as a general precautionary measure to reduce the probability of infection.

In the specification above, essential oil vapors are described that may be inhaled to reduce the probability of infection from the following wide range of pathogens: from bacteria causing tuberculosis; from opportunistic infections in the lungs of patients having cystic fibrosis; by inhaled bioterrorism pathogens including inhaled anthrax, smallpox, and botulism; by various viral, bacterial, and fungal pathogens causing pneumonia; and the known, and perhaps unknown, pathogens causing SARS.

Various essential oils have a wide range of antibacterial, antifungal, and antiviral properties. The antiseptic properties of essential oils may be chemically adjusted to have selected antiviral, selected antibacterial, and selected antifungal properties by mixing different oils, or by enhancing certain components found in those oils. Accordingly, in different preferred embodiments of the invention, any one component from any first essential oil may be added to any other second essential oil obtained from a plant or tree to enhance selected antiviral, selected antibacterial, and selected antifungal properties. In other preferred embodiments of the invention, any one component from any first essential oil may be added to any other combination of essential oils obtained from a combination of plants and/or trees to enhance selected antiviral, selected antibacterial, and selected antifungal properties. In fact, any one component from any essential oil may be used separately in certain preferred embodiments of the invention. In view of the above, essential oils obtained from plants and trees, and any components thereof, may be used in the various preferred embodiments of the invention.

Put yet another way, the inhalation of vapors from a mixture of essential oils such as 50% *Eucalyptus globulus* and 50% *Melaleuca alternifolia* is effective against many viruses (but not all viruses), many bacterial (but not all bacteria), and many fungi (but not all fungi), that inhaling these vapors reduces the probability of becoming infected by an unknown pathogen simply because in many cases (but not all the cases) the pathogen will be susceptible to the vapors. Therefore, inhaling this particular mixture reduces the probability of becoming infected by an unknown pathogen in an enclosed public area having one or more human beings present who may have variety of infectious respiratory diseases.

In view of the above specification, therefore another preferred embodiment of the invention is a method to prevent the infection of the human respiratory system by unknown pathogens that includes at least the step of inhaling the concentrated vapors from an essential oil having antiseptic properties, whereby the vapors are safe to inhale, and whereby the antiseptic properties include selected antibacterial properties, selected antiviral properties, and selected antifungal properties. Similar comments apply to the vapors from selected essential oils and mixtures of essential oils. In accordance with the above, the vapors from 100% *Melaleuca alternifolia* may be used in a preferred embodiment of the invention to prevent, treat, and cure infections of the human respiratory system by unknown pathogens.

Applicable Portions of the Anatomy and Related Maladies

Various preferred embodiments above have described methods of inhaling vapors from essential oils that may be inhaled for the prevention, mitigation, treatment and symptomatic relief of various respiratory ailments such as colds, flus, asthma, bronchitis, pneumonia, tuberculosis, and other ailments and infections of the human respiratory system which include ailments and infections of the upper respiratory tract, such as the throat, nasopharynx, the eustachian tube, the nasal passages, the sinuses, and the lower respiratory tract, such as the bronchi, bronchioles, the alveoli, and the lungs. Put another way, the invention pertains to the pulmonary anatomy, the sinus anatomy, the nasal anatomy, and the ear anatomy.

Each one of the above anatomical features has mucous and mucous membranes associated with each such anatomical feature. For example, the sinus cavities have mucous membranes and those membranes have their related mucous. The alveoli of the lungs also posses mucous and mucous membranes. For the purposes herein, the human respiratory system comprises all the above anatomical features and all the associated mucous membranes and the associated mucous within, and in contact with, those mucous membranes. So, for the purposes herein, the human respiratory system includes the pulmonary anatomy, the sinus anatomy, the nasal anatomy, the ear anatomy, and all the associated mucous membranes and the associated mucous within, and in contact with, those mucous membranes.

Many of the preferred embodiments herein provide for the inhalation of vapors from essential oils obtained from plants and trees. These essential oils are known to be generally fat soluble. Accordingly, the vapors from essential oils penetrate all features of the above defined human respiratory system including all the associated mucous membranes and the associated mucous within, and in contact with, those mucous membranes. So, the vapors from the essential oils penetrate the tissues of the pulmonary anatomy, the sinus anatomy, the nasal anatomy, major portions of the ear anatomy and all the associated mucous membranes and the associated mucous within, and in contact with, those mucous membranes.

The vapors described above are obtained from botanical essential oils, but may be also obtained from other medicinal, phytomedicinal, herbal and naturopathic oils and preparations. In fact vapors from any liquid having antibacterial and/or antiviral and/or antifungal properties are preferred embodiments of this invention. For the purposes of this section, the phrase "antiseptic fluid" shall mean that the fluid has selected antibacterial properties, selected antiviral properties, and antifungal properties.

For the purposes herein, an "infection" includes any bacterial, viral, or fungal infection of the human respiratory system that causes disease. For the purposes herein, an "inflammation" includes any response of the human body to a bacterial, viral, or fungal infection.

So, a preferred embodiment of this invention is the inhalation of vapors from any antiseptic fluid to prevent, treat, or cure any respiratory disease caused by an infection or any resulting inflammation. If any treatment simply reduces the number of pathogens with a patient causing disease, then the treatment is useful to help a patient recover from the disease.

Standard medical trials may be conducted to determine the formulation for the antisepctic fluids that are optimal. Such fluids may also include steroids in preferred embodiments that are mixed with any essential oil, mix of essential oils, or any component, or components from any essential oil.

The required effective amount of vapors to inhale from antiseptic fluids may be determined from human trials in accordance with conventional medical practice. The amount of vapor to be inhaled, the frequency of inhaling the vapor, and the duration of the treatment are all factors that may be determined from such human trials.

For the purposes herein, the term "associated" has been defined in the above section entitled "Severe Acute Respiratory Syndrome (SARS)". Because the antiseptic fluids have selected capabilities against bacteria, viruses, and fungi, the vapors from antiseptic fluids are effective at eradicating infections from many associated pathogens (bacteria, viruses, and fungi).

In view of the above, a preferred embodiment of the invention is the method to inhale an effective amount of vapors from any antiseptic fluid to prevent, treat, or cure infections from *Mycobacterium tuberculosis* causing tuberculosis and infections from any other pathogens associated with the tuberculosis, in the human respiratory system, including any related mucous membranes and any mucous related to those membranes.

In view of the above, another preferred embodiment of the invention is the method to inhale an effective amount of vapors from any antiseptic fluid to prevent, treat, or cure infections from opportunistic infections associated with cystic fibrosis in the human respiratory system, including any related mucous membranes and any mucous related to those membranes.

In view of the above, another preferred embodiment of the invention is the method to inhale an effective amount of vapors from any antiseptic fluid to prevent, treat, or cure infections from bioterrorism pathogens and infections from any other pathogens associated with such bioterrorism pathogens, in the human respiratory system, including any related mucous membranes and any mucous related to those membranes.

In view of the above, another preferred embodiment of the invention is the method to inhale an effective amount of vapors from any antiseptic fluid to prevent, treat, or cure infections from bacteria, viruses, and fungi that cause sinusitis and infections from any other pathogens associated with sinusitis, in the human respiratory system, including any related mucous membranes and any mucous related to those membranes.

In view of the above, another preferred embodiment of the invention is the method to inhale an effective amount of vapors from any antiseptic fluid to prevent, treat, or cure infections from bacteria, viruses, and fungi that cause rhinitis and infections from any other pathogens associated with rhinitis, in the human respiratory system, including any related mucous membranes and any mucous related to those membranes.

In view of the above, another preferred embodiment of the invention is the method to inhale an effective amount of vapors from any antiseptic fluid to prevent, treat, or cure infections from pathogens causing pathogenic asthma, pathogenic bronchitis, and pathogenic emphysema and infections from any other pathogens associated with these maladies, in the human respiratory system, including any related mucous membranes and any mucous related to those membranes.

In view of the above, another preferred embodiment of the invention is the method to inhale an effective amount of vapors from any antiseptic fluid to prevent, treat, or cure infections from bacteria, viruses, and fungi causing pneumonia and infections from any other pathogens associated with the pneumonia, in the human respiratory system, including any related mucous membranes and any mucous related to those membranes.

In view of the above, another preferred embodiment of the invention is the method to inhale an effective amount of vapors from any antiseptic fluid to prevent, treat, or cure infections from viruses that infect the respiratory system and infections from any other pathogens associated with those viruses, in the human respiratory system, including any related mucous membranes and any mucous related to those membranes.

In view of the above, yet another preferred embodiment of the invention is the method to inhale an effective amount of vapors from any antiseptic fluid to prevent, treat, or cure infections from the pathogen or pathogens causing Severe Acute Respiratory Syndrome (SARS) and infections from any other pathogens associated with SARS, in the human respiratory system, including any related mucous membranes and any mucous related to those membranes.

In view of the above, another preferred embodiment of the invention is the method to inhale an effective amount of vapors from any antiseptic fluid to prevent, treat, or cure infections from unknown pathogens and infections from any other pathogens associated with the unknown pathogens, in the human respiratory system, including any related mucous membranes and any mucous related to those membranes.

In the above preferred embodiments, the phrase "vapors from any antiseptic fluid" may be replaced with "any antisepctic aerosol". The phrase "aerosol" has been defined in relation to FIG. 1.

In the above preferred embodiments, the phrase "vapors from any antiseptic fluid" may be replaced with "vapors from any antiseptic substance".

Summary of Preferred Embodiments

In accordance with the above specification, a preferred embodiment of the invention is a method to reduce the risks of infection of the human respiratory system by pathogens causing Severe Acute Respiratory Syndrome (SARS) in an enclosed public area having one or more human beings within the public area comprising the following steps:

(a) within a period of time of 30 minutes before entering the public area, inhaling an effective amount of the concentrated vapors from *Eucalyptus globulus;* and (b) after entering the public area, periodically inhaling the concentrated vapors from *Eucalyptus globulus*, whereby the period of time between successive inhalations exceeds 30 minutes, and whereby the period of time between successive inhalations is less than 2 hours.

This method applies when the pathogens include at least one strain of a coronavirus. This method applies when the pathogens include at least one strain of a paramyxovirus. This method applies when the pathogens include at least one strain of a coronavirus in association with at least a selected one of a strain of paramyxovirus and a strain of *chlamydia* bacteria.

In accordance with the above specification, another preferred embodiment of the invention is a method to reduce the risks of infection of the human respiratory system by pathogens causing Severe Acute Respiratory Syndrome (SARS) in an enclosed public area having one or more human beings within the public area comprising the following steps:

(a) within a period of time of 30 minutes before entering the public area, inhaling an effective amount of the concentrated vapors from an essential oil that possesses antiseptic properties, whereby the vapors are safe for human inhalation, and whereby the antiseptic properties include selected antiviral, selected antibacterial, and selected antifungal properties; and (b) after entering the public area, periodically inhaling the concentrated vapors from the essential oil, whereby the period of time between successive inhalations exceeds 30 minutes, and whereby the period of time between successive inhalations is less than 2 hours.

This method applies when the pathogens include at least one variety of coronavirus. This method applies when the pathogens include at least one variety of paramyxovirus. This method applies when the pathogens include at least one variety of coronavirus in association with at least a selected one of a variety of paramyxovirus and variety of *chlamydia* bacteria. This method applies when the essential oil is selected to be one or more from the following list of essential oils: *Eucalyptus globulus, Melaleuca alternifolia, Eucalyptus citriodora,* and *Eucalyptus radiata.*

In view of the above specification, another preferred embodiment of the invention is a method to reduce the risks of infection of the human respiratory system by unknown respiratory pathogens in an enclosed public area having one or more human beings within the public area comprising the following steps:

(a) within a period of time of 30 minutes before entering the public area, inhaling the concentrated vapors from an essential oil that possesses antiseptic properties, whereby the vapors are safe for human inhalation, and whereby the antiseptic properties include selected antiviral, selected antibacterial, and selected antifungal properties, and whereby the concentrated vapors from the essential oil are inhaled from a hand-held inhaler apparatus; and (b) after entering the public area, periodically inhaling the concentrated vapors from the essential oil, whereby the period of time between successive inhalations exceeds 30 minutes, and whereby the period of time between successive inhalations is less than 2 hours.

This method applies when the unknown respiratory pathogens include the pathogen causing Severe Acute Respiratory Syndrome (SARS). This method applies when the unknown pathogens include a variety of an influenza virus causing a flu. This method applies when the unknown pathogens include a variety of a rhinovirus causing a cold. This method applies when the unknown pathogens include any variety of the bacterium *Staphylococcus aureus* that causes staphylococcal pneumonia. This method applies when the unknown pathogens include any variety of the bacterium *Mycobacterium tuberculosis* that causes tuberculosis. This method applies when the unknown pathogens include any variety of the fungus *Blastomyces dermatitidis* that causes a fungal pneumonia. This method applies when the essential oil is selected to be one or more from the following list of essential oils: *Eucalyptus globulus, Melaleuca alternifolia, Eucalyptus citriodora,* and *Eucalyptus radiata.*

In view of the above specification, another preferred embodiment is a method to prevent the infection of the human respiratory system by unknown pathogens that includes at least the step of inhaling the concentrated vapors from an essential oil having antiseptic properties, whereby the vapors are safe to inhale, and whereby the antiseptic properties include selected antibacterial properties, selected antiviral properties, and selected antifungal properties.

In view of the above specification, another preferred embodiment is a method to treat the infection of the human respiratory system by pathogens causing Severe Acute Respiratory Syndrome (SARS) that includes at least the step of the inhalation of an effective amount of concentrated vapors from an essential oil having antiseptic properties, whereby the vapors are safe to inhale, and whereby the antiseptic properties include selected antibacterial properties, selected antiviral properties, and selected antifungal properties.

This method applies when the essential oil is comprised of at least a selected one of *Eucalyptus globulus, Melaleuca alternifolia, Eucalyptus citriodora,* and *Eucalyptus radiata.* This method also applies when the essential oil is comprised of a mixture of one or more of *Eucalyptus globulus, Melaleuca alternifolia, Eucalyptus citriodora,* and *Eucalyptus radiata.*

Further, in view of the above specification, another preferred embodiment of the invention is a method to treat the infection of the human respiratory system by unknown pathogens that includes at least the step of inhaling concentrated vapors from an essential oil having antiseptic properties, whereby the vapors are safe to inhale, and whereby the antiseptic properties include selected antibacterial properties, selected antiviral properties, and selected antifungal properties.

And finally, in view of the above specification, another preferred embodiment of the invention is a method to treat the infection of the human respiratory system by pathogens causing Severe Acute Respiratory Syndrome (SARS) that includes at least the step of the inhalation of an effective amount of concentrated vapors from any substance having antiseptic properties, whereby the vapors are safe to inhale, and whereby the antiseptic properties include selected antibacterial properties, selected antiviral properties, and selected antifungal properties.

REFERENCES

The above recited references are defined as follows, entire copies of which are incorporated herein by reference:

Alibek, K. W., and Handelman, S., the book entitled "Biohazard: The Chilling True Story of the Largest Covert Biological Weapons Program in the World", Dell Publishing Company, 2000 ("Alibek and Handelman, 2000")

Alstat, E., the paper entitled "Lomatium Dissectum, An Herbal Virucide", in the journal called "Complementary Medicine", May/June 1987, pages 32–33 ("Alstat, 1987") [Ed Alstat]

Anderson, K. N., Anderson, L. E., and Glanze, W. D., Editors, the book entitled "Mosby's Medical Dictionary", Fourth Edition, Mosby-Year Book Inc., St. Louis, Mo., 1994 ("Anderson, et al., 1994")

Arnon, S. S., in the article entitled "Botulinum Toxin as a Biological Weapon, Medical and Pubic Health Management", Journal of the American Medical Association, Vol. 285, No. 8, Feb. 28, 2001, pages 1059–1070 ("Arnon, 2001") [Stephen S. Arnon, M.D.]

Audesirk, T., and Audesirk, G., the book entitled "Biology, Life on Earth", Fourth Edition, Prentice Hall, Upper Saddle River, New Jersey, 1996 ("Audesirk and Audesirk, 1996") [Teresa Audesirk and Gerald Audesirk]

Balch, J. F., and Balch, P. A., the book entitled "Prescription for Nutritional Healing", Second Edition, Avery Publishing Group, Garden City Park, New York, N.Y., 1997 ("Balch and Balch, 1997") [James F. Balch, M.D. and Phyllis A. Balch, C.N.C.]

Balch, J. F., and Balch, P. A., the book entitled "Prescription for Nutritional Healing", Third Edition, Avery Publishing Group, Garden City Park, New York, N.Y., 2000 ("Balch and Balch, 2000") [James F. Balch, M.D. and Phyllis A. Balch, C.N.C.] (was old Reference 7 in PPA-2)

Berkow, R., and Beers, M. H., Editors, the book entitled "The Merck Manual of Medical Information", "Home Edition", Pocket Books, a Division of Simon & Schuster, Inc., New York, N.Y., 1997 ("Berkow and Beers, 1997") [Robert Berkow, M.D. and Mark H. Beers M.D.]

Beers, M. H., and Berkow R., Editors, the Publication on the World Wide Web (http://www.merck.com/pubs/mmanual/) entitled "The Merck Manual of Diagnosis and Therapy", "Seventeenth Edition", "Centennial Edition", Merck & Co., Whitehouse Station, N.J., 1999 ("Beers, et al., 1999") [Mark H. Beers, M.D., and Robert Berkow, M.D.]

Borio, L., et al., the article entitled "Hemorrhagic Fever Viruses as Biological Weapons, Medical and Public Health Management", the Journal of the American Medical Association, Vol. 287, No. 18, May 8, 2002, pages 2391–2405 ("Borio, et al., 2002") [Luciana Borio, M.D.]

Buck, D. S., Nidorf, D. M., and Addino, J. G., the article entitled "Comparison of two topical preparations for the treatment of onychomycosis: *Melaleuca Alternifolia* (tea tree) oil and clotrimazole", in the Journal of Family Practice, Volume 38, No. 6, pages 601–605, 1994 ("Buck, et al., 1994")

Dennis, D. T., the article entitled "Tularemia as Biological Weapon, Medical and Public Health Management", Journal of the American Medical Association, Vol. 285, No. 21, Jun. 6, 2001, pages 2763–2773 ("Dennis, et al., 2001") [David T. Dennis, M.D., M.P.H.]

Editor, the book entitled "A Dictionary of Biology", Third Edition, Oxford University Press, New York, N.Y., 1996 ("Oxford, 1996")

Editor, the article entitled "Allergy, Asthma, and Sinus" on the World Wide Web (http://allergy-asthma-sinus.com/) dated Apr. 8, 2002 by the Allergy, Asthma and Sinus Resource Center, Miami, Fla. that was printed-out on Apr. 30, 2002, ("Allergy, Asthma and Sinus Resource Center, 2002")

Editor, in the document entitled "Common Infections" from the web site for the "Community Outreach Health Information Service" or "COHIS" (http://www.cohis.org) that was printed out on Apr. 30, 2002, ("COHIS, 2002")

Editor, the article entitled "Protein could beat cholesterol as indicator of heart risk" in the section entitled "Medical Digest", The Seattle Times, Mar. 24, 2000, page A7 ("The Seattle Times, 2000")

Editor, the article entitled "Sinusitis" on the World Wide Web Site entitled "drkoop.com", printed out on Apr. 30, 2002, ("DrKoop.com, 2002")

Editor, the article entitled "Sinusitis (Sinus Infection)" on the World Wide Web Site entitled "Medical College of Wisconsin Physicians & Clinics (http://www.healthlink.mcw.edu/), printed out on Apr. 30, 2002, ("Medical College of Wisconsin Physicians & Clinics, 2002")

Ellison, D. H., the book entitled "Handbook of Chemical and Biological Warfare Agents", CRC Press, 1999 ("Ellison, 1999")

Falkenrath, R. A., Newman, R. D., and Thayer, B. A., the book entitled "America's Achilles' Heel: Nuclear, Biological, and Chemical Terrorism and Covert Attack", MIT Press, 1998 ("Falkenrath, et al., 1998")

Fugh-Berman, A., the book entitled "Alternative Medicine, What Works", Williams & Wilkins, Baltimore, Md., 1997 ("Fugh-Berman, 1997") [Adriane Fugh-Berman, M.D.]

Gunther, E., the book entitled "The Essential Oils", Volumes I, II, III, and IV, Lancaster Press, Lancaster, Pa., 1948 ("Gunther, 1948")

Hedges, L. M. and Wilkens, C. L., the article entitled "Component Analysis of *Eucalyptus* Oil by Gas Chromatography-Fourier Transform-Infrared Spectrometry-Mass Spectrometry", in the publication called the Journal of Chromatographic Science, Volume 29, August, 1991 ("Hedges and Wilkens, 1991")

Henderson, D. A., in the article entitled "Smallpox as a Biological Weapon, Medical and Public Health Management", Journal of the American Medical Association, Vol. 281, No. 22, Jun. 9, 1999, pages 2177–2137 ("Henderson, 1999") [Donald A. Henderson, M.D., M.P.H.]

Horowitz, L. G., and Lindenbach, J. G., the book entitled "Death in the Air: Globalism, Terrorism and Toxic Warfare", *Tetrahedron* Publishing Group, 2001 ("Horowitz and Lindenbach, 2001")

Igram, C., the book entitled "Killed on Contact, The Tea Tree Oil Story: Nature's Finest Antiseptic", Literary Visions Publishing, Inc., Cedar Rapids, Iowa, 1992 ("Igram, 1992") [Cass Igram, D. O.]

Inglesby, T. V., et al., the article entitled "Plague as a Biological Weapon, Medical and Public Health Management", Journal of the American Medical Association", Vol. 283, No. 17, May 3, 2000, pages 2281–2290 ("Inglesby, et al. 2000") [Thomas V. Inglesby, M.D.]

Inglesby, T. V., et al., the article entitled "Anthrax as Biological Weapon, 2002, Updated Recommendations for Management", the Journal of the American Medical Association, Volume 287, No. 17, May 1, 2002, pages 2236–2252 ("Inglesby, et al., 2002") [Thomas V. Inglesby, M.D.]

Institute of Medicine, the book entitled "Chemical and Biological Terrorism: Research and Development to Improve Civilian Medical Response", National Academy Press, 1999 ("Institute of Medicine, 1999")

Inouye, S., et al., the article entitled "Antibacterial activity of essential oils and their major constituents against respiratory tract pathogens by gaseous contact", Journal of Antimicrobial Chemotherapy (The British Society for Antimicrobial Chemotherapy), Volume 47, 2001, pages 565–573, 2001, ("Inouye, et al., 2001")

Jacobs, M. R., Hornfeldt, C. S., the article entitled "Melaleuca oil poisoning", in the journal called "Clinical Toxicology", Volume 32, No. 4, pages 461–464, 1994 ("Jacobs and Hornfeldt, 1994")

Kohn, L., Corrigan, J., and Donaldson, M., Editors, the book entitled "To Err is Human, Building a Safer Health System", "Advanced Copy", Institute of Medicine, National Academy Press, Washington, D.C., 1999 ("Kohn, et al., 1999") [Linda T. Kohn, Janet M. Corrigan, and Molla S. Donaldson]

Lawless, J., the book entitled "Tea Tree Oil", Harper Collins Publishers, Hammersmith, London, U.K., 1994 ("Lawless, 1994") [Julia Lawless]

Lawless, J., the book entitled "The Illustrated Encyclopedia of Essential Oils", Barnes & Noble Books, New York, N.Y., 1999 ("Lawless, 1999") [Julia Lawless]

Luckmann, J., Editor, the book
entitled "Saunders, Manual of Nursing Care", W. B. Saunders Company, Philadelphia, Pa., 1997 ("Luckmann, 1997") [Joan Luckmann, MA, RN]

Mangold, T., and Boldberg, J., the book entitled "Plague Wars: The Terrifying Reality of Biological Warfare", Martin's Press, 2001 ("Mangold and Boldberg, 2001")

Martin, E., Ruse, M., and Holmes, E., Editors, the book entitled "A Dictionary of Biology", Third Edition, Oxford University Press, New York, N.Y., 1996 ("Martin, et al., 1996") [Elizabeth Martin MA; Michael Ruse BSc, PhD; and Elaine Holmes BSc, PhD]

Miller, J., Engelberg, S., and Broad, W. J., the book entitled "Germs: Biological Weapons and America's Secret War", Simon & Schuster, 2001 ("Miller, et al., 2001")

Miller, L., and Miller, B., the book entitled "Ayurveda & Aromatherapy, The Earth Essential Guide to Ancient Wisdom and Modern Healing", Lotus Press, Twin Lakes, Wis., 1995 ("Miller and Miller, 1995") [Dr. Light Miller, ND, and Dr. Bryan Miller, DC]

Moore, P., the book entitled "Killer Germs, Rogue Diseases of the Twenty-First Century", Carlton Books Limited, London, Great Britain, 2001 ("Moore, 2001") [Pete Morre B.Sc., Ph.D.]

Murray, M. T., the book entitled "Natural Alternatives to Over-the-Counter and Prescription Drugs", William Morrow and Company, Inc., New York, N.Y., 1994, ("Murray, 1994") [Michael T. Murray, N.D.]

Neufeldt, V., and Guralnik, D., the book entitled the Webster's New World™ Dictionary of American English, Third College Edition, Simon & Schuster, Inc., New York, N.Y., 1988 ("Neufeldt and Guralnik, 1988")

Olsen, C., the book entitled "Australian Tea Tree Oil Guide", Kali Press, Pagosa Springs, Colo., 1991, ("Olsen, 1991") [Cynthia B. Olsen]

Olsen, C., the book entitled "Australian Tea Tree Oil Guide", Third Edition, Kali Press, Pagosa Springs, Colo., 1997 ("Olsen, 1997") [Cynthia Olsen]

Osterholm, M. T., and Schwartz, J., the book entitled "Living Terror: What America Needs to Know to Survive the Coming Bioterrorist Catastrophe", Dell Publishing Company, 2001 ("Osterholm and Schwartz, 2001")

Price, S., and Price, L., the book entitled "Aromatherapy for Health Professionals", Second Edition, Churchill Livingstone, New York, N.Y., 1999 ("Price and Price, 1999") [Shirley Price and Len Price]

Regis, E., the book entitled ""The Biology of Doom: The History of America's Secret Germ Warfare Project", Henry Holt & Company, 1999 ("Regis, 1999")

Rose, J., the book entitled "375 Essential Oils and Hydrosols", Frog, Limited, Berkeley, Calif., 1999 ("Rose, 1999") [Jeanne Rose]

Schnaubelt, K., the book entitled "Advanced Aromatherapy, The Science of Essential Oil Therapy", Healing Arts Press, a division of Inner Traditions International, Rochester, Vt., 1998 ("Schnaubelt, 1998") ["Kurt Schnaubelt, Ph.D."]

Schnaubelt, K., the book entitled "Medical Aromatherapy, Healing with Essential Oils", Frog, Ltd., Berkeley, Calif., 1999 ("Schnaubelt, 1999")

Sherry, E., and Warnke, P. H. H., the paper entitled "Alternative for MRSA and Tuberculosis (TB): *Eucalyptus* and Tea-Tree Oils as New Topical Antibacterials", Poster Board Number: P376, 2002 Annual Meeting of the American Academy of Orthopaedic Surgeons, Dallas, Tex., Feb. 13–17, 2002 ("Sherry and Warnke, 2002") [Eugene Sherrry, M.D., and P. H. H. Warnke, Ph.D.]

Sullivan, J. B., Rummack, B. H., and Thomas, H., in the article entitled "Pennyroyal oil poising and hepatoxicity", in the Journal of the American Medical Association, Volume 242, No. 26, pages 2873–74, 1979 ("Sullivan, et al., 1979")

Swords, G. and Hunter, G. L. K., in the article entitled "Composition of Australian Tea Tree Oil (*Melaleuca alternifolia*)" presented in the Journal of Agricultural Food Chemistry, Volume 26, No. 3, 1978, pages 734–737 ("Swords and Hunter, 1978")

Taylor, E. R., the book entitled "Lethal Mists: An Introduction to the Natural and Military Sciences of Chemical, Biological Warfare and Terrorism", Nova Science, 1999 ("Taylor, 1999")

Tucker, J. B., in the book entitled "Toxic Terror: Assessing Terrorist Use of Chemical and Biological Weapons", MIT Press, 2000 ("Tucker, 2000")

Vallence, W. B., the article entitled "Pennyroyal poisoning: a fatal case", in the journal called "Lancet", Volume 2, pages 850–851, 1955 ("Vallence, 1955")

Webb, N. J., and Pritt, W. R., the article entitled "*Eucalyptus* oil poisoning in childhood: 41 cases in south-east Queensland", in the journal called "Journal of Paediatrics and Child Health", Volume 29, pages 368–371, 1993 ("Webb and Pritt, 1993")

Weinstein, A. M., the book entitled "Asthma, The Complete Guide to Self-Management of Asthma and Allergies for Patients and Their Families", A Fawcett Crest Book, The Ballantine Publishing Group, New York, N.Y., 1988 ("Weinstein, 1988") [Allen M. Weinstein, M.D.]

Williams, D. G., the article entitled "New Uses for An Age-Old Therapy", in the newsletter called "Alternatives For the Health Conscious Individual", Vol. 8, No. 4, October, 1999 ("Williams, 1999") [Dr. David G. Williams]

Again, entire copies of all the above cited references in this section entitled "References" are incorporated herein by reference. In addition, each above cited references refer to yet other papers, publications, books, etc., and entire copies of each and every such document is also incorporated herein by reference in their entirety. For example, Hedges and Wilkens, 1991, cite under its "References" and item "1." a book that is entitled "The Essential Oils", Vol. I, II, and IV, by the author of E. Gunther, Lancaster Press, Lancaster, Pa., 1948, and according the previous sentence, an entire copy of that reference is incorporated herein by this statement.

While the above description contains many specificities, these should not be construed as limitations on the scope of the invention, but rather as exemplification of preferred embodiments thereto. As have been briefly described, there are many possible variations. Accordingly, the scope of the invention should be determined not only by the embodiments illustrated, but by the appended claims and their legal equivalents.

What is claimed is:

1. A method to reduce risks of infection of the human respiratory system by respiratory pathogens in an enclosed public area having one or more human beings within said public area, comprising the following steps:
    (a) within a period of time of 30 minutes before entering said public area, inhaling concentrated vapors from an essential oil that possess anti-pathogenic properties, whereby said vapors are non-toxic when inhaled, and whereby said anti-pathogenic properties include selected ativiral, selected antibacterial, and selected antifungal properties, and whereby the concentrated vapors from said essential oil are inhaled from a hand-held inhaler apparatus; and
    (b) after entering said public area, periodically inhaling a concentrated vapors from said essential oil, whereby the period of time between successive inhalations exceeds 30 minutes, and whereby the period of time between successive inhalations is less than 2 hours; and
    whereby said pathogens are selected from the group consisting of an influenza virus causing influenza and a rhinovirus causing a cold, and
    whereby the essential oil is selected to be one or more from the following list of essential oils: *Eucalyptus globulus, Melaleuca alternifolia, Eucalyptus citriodora,* and *Eucalyptus radiata.*

2. The method of claim 1 whereby the essential oil is selected to be one or more from the following list of essential oils: *Eucalyptus globulus,* and *Melaleuca alternifolia.*

3. The method of claim 1 whereby the essential oil is comprised of 50% *Eucalyptus globulus,* and 50% *Melaleuca alternifolia.*

4. A method to reduce risks of infection of the human respiratory system by respiratory pathogens in an enclosed public area having one or more human beings within said enclosed area comprising the following steps:
    (a) within a period of time of 30 minutes before entering said public area, inhaling concentrated vapors from an essential oil mixture comprising 50% *Eucalyptus globulus* and 50% *Melaleuca alternifolia,*
    whereby the concentrated vapors from said essential oil mixture are inhaled from a hand-held inhaler apparatus; and
    (b) after entering said public area, periodically inhaling a concentrated vapors, whereby the period of time between successive inhalations exceed 30 minutes, and whereby the period of time between successive inhalations is less than 2 hours; and
    whereby said respiratory pathogens are selected from the group consisting of any respiratory pathogens causing Severe Acute Respiratory Syndrome (SARS).

5. A method to reduce risks of infection of the human respiratory system by respiratory pathogens in an enclosed public area having one or more human beings within said public area, comprising the following steps:
    (a) within a period of time of 30 minutes before entering said public area, inhaling concentrated vapors from an essential oil that possess anti-pathogenic properties, whereby said vapors are non-toxic when inhaled, and whereby said anti-pathogenic properties include selected antiviral, selected antibacterial, and selected antifungal properties, and
    whereby the concentrated vapors from said essential oil are inhaled from a hand-held inhaler apparatus; and
    (b) after entering said public area, periodically inhaling the concentrated vapors from said essential oil, whereby a period of time between successive inhalations exceeds 30 minutes, and whereby the period of time between successive inhalations is less than 2 hours; and
    whereby said pathogens are selected from the group consisting of an influenza virus causing influenza, and a rhinovirus causing a cold, and a coronavirus causing a cold, and a coronavirus causing Severe Acute Respiratory Syndrome (SARS), and
    whereby the essential oil is seleceted to be one or more from the following list of essential oils: *Eucalyptus globulus, Melaleuca alternifolia, Eucalyptus citriodora,* and *Eucalyptus radiata.*

6. The method in claim 5 whereby the essential oil is selected to be one or more from the following list of essential oils: *Eucalyptus globulus,* and *Melaleuca alternifolia.*

7. The method in claim 5 whereby the essential oil is comprised of 50% *Eucalyptus globulus,* and 50% *Melaleuca alternifolia.*

* * * * *